United States Patent
Rourke et al.

(10) Patent No.: US 7,125,420 B2
(45) Date of Patent: Oct. 24, 2006

(54) METHOD AND APPARATUS FOR IMPROVING MITRAL VALVE FUNCTION

(75) Inventors: Jonathan Rourke, Belmont, MA (US); John R. Liddicoat, Boston, MA (US); Daniel C. Taylor, Brighton, MA (US); William E. Cohn, Chestnut Hill, MA (US)

(73) Assignee: Viacor, Inc., Wilmington, DE (US)

( * ) Notice: Subject to any disclaimer, the term of this patent is extended or adjusted under 35 U.S.C. 154(b) by 0 days.

(21) Appl. No.: 10/446,470

(22) Filed: May 27, 2003

(65) Prior Publication Data

US 2004/0073302 A1 Apr. 15, 2004

Related U.S. Application Data

(63) Continuation-in-part of application No. 10/342,034, filed on Jan. 14, 2003, and a continuation-in-part of application No. 10/280,401, filed on Oct. 25, 2002, now Pat. No. 7,052,487, and a continuation-in-part of application No. 10/218,649, filed on Aug. 14, 2002, and a continuation-in-part of application No. 10/112,354, filed on Mar. 29, 2002, and a continuation-in-part of application No. 10/068,264, filed on Feb. 5, 2002, now Pat. No. 6,656,221.

(60) Provisional application No. 60/391,790, filed on Jun. 26, 2002.

(51) Int. Cl.
*A61F 2/24* (2006.01)
*A61F 2/06* (2006.01)

(52) U.S. Cl. ................ 623/2.36; 623/904

(58) Field of Classification Search ............. 623/1.16, 623/1.3, 2.36, 2.37, 903, 904; 604/525
See application file for complete search history.

(56) References Cited

U.S. PATENT DOCUMENTS

| | | | |
|---|---|---|---|
| 4,535,757 A | 8/1985 | Webster |
| 4,669,473 A | 6/1987 | Richards et al. |
| 4,917,698 A | 4/1990 | Carpentier et al. |
| 4,944,745 A | 7/1990 | Sogard et al. |
| 5,061,277 A | 10/1991 | Carpentier et al. |
| 5,092,889 A | 3/1992 | Campbell, Jr. |
| 5,133,732 A | 7/1992 | Wiktor |
| 5,269,809 A | 12/1993 | Hayhurst et al. |
| 5,332,402 A | 7/1994 | Teitelbaum |
| 5,383,892 A | 1/1995 | Cardon et al. |
| 5,389,091 A | 2/1995 | Moorehead |
| 5,443,481 A | 8/1995 | Lee |
| 5,462,530 A | 10/1995 | Jang |

(Continued)

FOREIGN PATENT DOCUMENTS

EP 0756853 A1 2/1997

(Continued)

OTHER PUBLICATIONS

Buchanan, James W., Circumferential Suture of the Mitral Annulus for Correction of Mitral Regurgitation in Dogs, Veterinary Surgery, 1998, pp. 182-193.

(Continued)

*Primary Examiner*—Brian E. Pellegrino
(74) *Attorney, Agent, or Firm*—Pandiscio & Pandiscio

(57) ABSTRACT

A method and apparatus for reducing mitral regurgitation. The apparatus is inserted into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation and reduce mitral regurgitation.

28 Claims, 49 Drawing Sheets

U.S. PATENT DOCUMENTS

| | | | |
|---|---|---|---|
| 5,476,506 | A | 12/1995 | Lunn |
| 5,545,209 | A | 8/1996 | Roberts et al. |
| 5,569,201 | A | 10/1996 | Burns |
| 5,575,799 | A | 11/1996 | Bolanos et al. |
| 5,720,726 | A | 2/1998 | Marcadis et al. |
| 5,755,778 | A | 5/1998 | Kleshinski |
| 5,755,781 | A | 5/1998 | Jayaraman |
| 5,800,495 | A | 9/1998 | Machek et al. |
| 5,800,526 | A | 9/1998 | Anderson et al. |
| 5,855,565 | A | 1/1999 | Bar-Cohen et al. |
| 5,911,732 | A | 6/1999 | Hojeibane |
| 5,911,752 | A * | 6/1999 | Dustrude et al. ........... 606/192 |
| 5,957,949 | A | 9/1999 | Leonhardt et al. |
| 5,980,570 | A | 11/1999 | Simpson |
| 5,984,917 | A | 11/1999 | Fleischman et al. |
| 6,033,436 | A | 3/2000 | Steinke et al. |
| 6,051,020 | A | 4/2000 | Goicoechea et al. |
| 6,071,263 | A | 6/2000 | Kirkman |
| 6,086,599 | A | 7/2000 | Lee et al. |
| 6,090,136 | A | 7/2000 | McDonald et al. |
| 6,119,037 | A | 9/2000 | Kellogg et al. |
| 6,162,245 | A | 12/2000 | Jayaraman |
| 6,165,194 | A | 12/2000 | Denardo |
| 6,187,040 | B1 | 2/2001 | Wright |
| 6,210,432 | B1 | 4/2001 | Solem et al. |
| 6,241,746 | B1 | 6/2001 | Bosma et al. |
| 6,258,117 | B1 | 7/2001 | Camrud et al. |
| 6,277,107 | B1 | 8/2001 | Lurie et al. |
| 6,287,336 | B1 * | 9/2001 | Globerman et al. ......... 623/1.3 |
| 6,328,765 | B1 | 12/2001 | Hardwick et al. |
| 6,332,896 | B1 | 12/2001 | Hubbard et al. |
| 6,402,781 | B1 | 6/2002 | Langberg et al. |
| 6,419,696 | B1 | 7/2002 | Ortiz et al. |
| 6,537,314 | B1 | 3/2003 | Langberg et al. |
| 6,569,198 | B1 | 5/2003 | Wilson et al. |
| 6,585,716 | B1 | 7/2003 | Altman |
| 6,602,288 | B1 | 8/2003 | Cosgrove et al. |
| 6,648,874 | B1 | 11/2003 | Parisi et al. |
| 6,656,221 | B1 | 12/2003 | Taylor et al. |
| 2001/0018611 | A1 | 8/2001 | Solem et al. |
| 2001/0044568 | A1 | 11/2001 | Langberg et al. |
| 2001/0052345 | A1 | 12/2001 | Niazi |
| 2002/0016628 | A1 | 2/2002 | Langberg et al. |
| 2002/0087173 | A1 | 7/2002 | Alferness et al. |
| 2002/0103532 | A1 | 8/2002 | Langberg et al. |
| 2002/0103533 | A1 | 8/2002 | Langberg et al. |
| 2002/0151961 | A1 | 10/2002 | Lashinshi et al. |
| 2002/0169502 | A1 | 11/2002 | Mathis |
| 2002/0169504 | A1 | 11/2002 | Alfreness et al. |
| 2003/0069636 | A1 | 4/2003 | Solem et al. |
| 2003/0083538 | A1 | 5/2003 | Adams et al. |
| 2003/0093148 | A1 | 5/2003 | Bolling et al. |
| 2003/0105520 | A1 | 6/2003 | Alfreness et al. |
| 2005/0222678 | A1 | 10/2005 | Lashinksi et al. |

FOREIGN PATENT DOCUMENTS

| | | |
|---|---|---|
| JP | 409322936 A | 12/1997 |
| WO | WO 0062708 | 10/2000 |
| WO | WO 01/00111 A1 | 1/2001 |
| WO | WO 01/54618 A1 | 8/2001 |
| WO | WO 02/053206 A2 | 7/2002 |
| WO | WO 02/060352 A1 | 8/2002 |
| WO | WO 02/062270 A1 | 8/2002 |
| WO | WO 02/091908 A1 | 11/2002 |
| WO | WO 02/100240 A2 | 12/2002 |
| WO | WO 03/037171 A2 | 5/2003 |

OTHER PUBLICATIONS

Kerstetter, Kyle K. et al., Short-Term Hemodynamic Evaluation of Circumferential Mitral Annuloplasty for Correction of Mitral Valve Regurgitation in Dogs, Veterinary Surgery, 1998, pp. 216-223.

Beardow, Andrew W. et al., Chronic Mitral Valve Disease in Cavalier King Charles Spaniels: 95 Cases (1987-1991), Javma, vol. 203, No. 7, Oct. 1, 1993, pp. 1023-1029.

Davila, Julio C. et al., Circumferential Suture of The Mitral Ring, 18 pages.

Glover, Robert P. et al., The Treatment of Mitral Valve Insufficiency By The Purse-String Technique, The Journal of Thoracic Surgery, Jan. 1957, 14 pages.

Davila, Julio C. et al., Circumferential Suture of The Mitral Valve for the Correction of Regurgiation, The American Journal of Cardiology, Inc., Sep. 1958, 6 pages.

Buchanan, James W., Causes and Prevalence of Cardiovascular Disease, Current Veterinary Therapy XI, WB Saunders Co., 1992, 2 pages.

\* cited by examiner

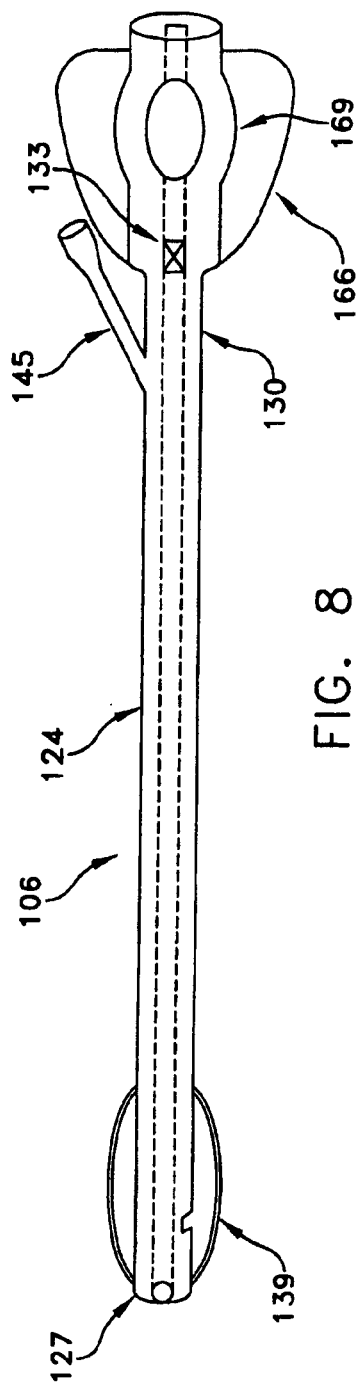
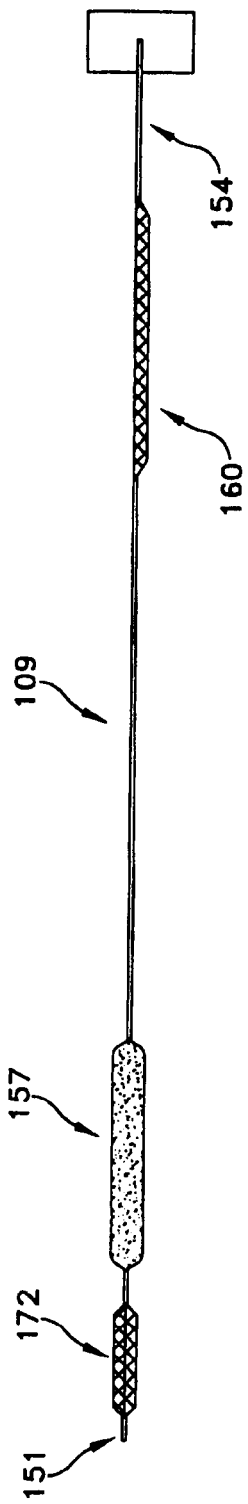
FIG. 8
FIG. 9

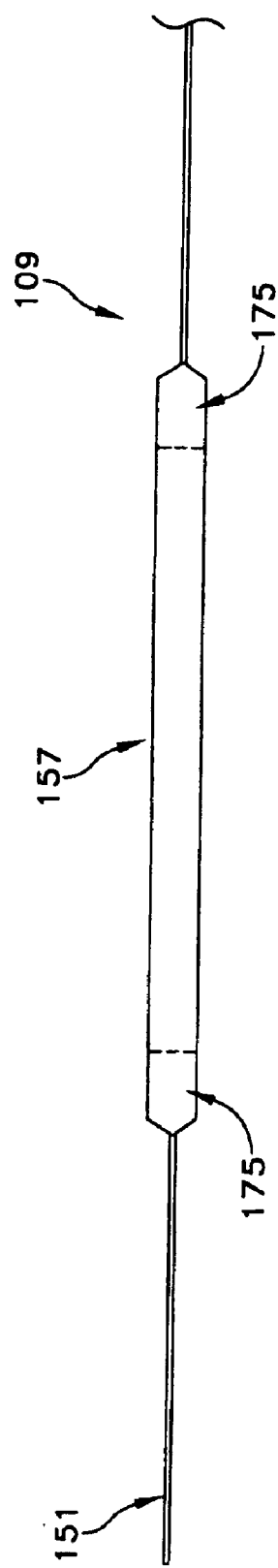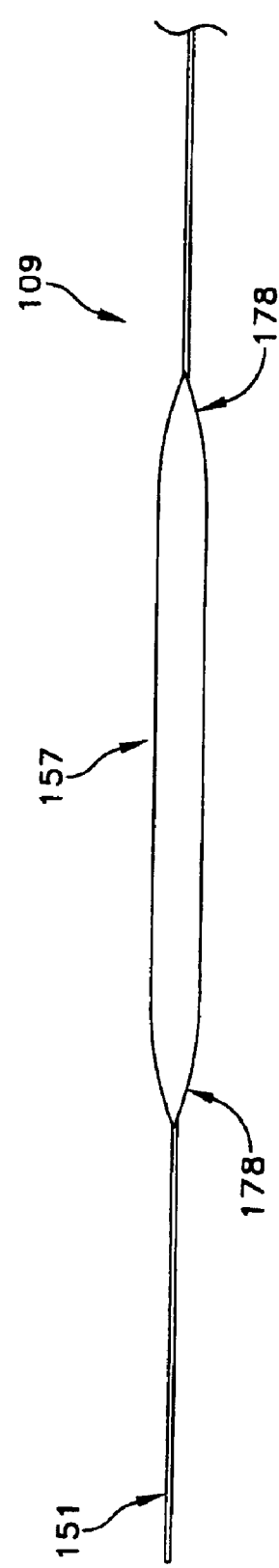

METHOD AND APPARATUS FOR IMPROVING MITRAL VALVE FUNCTION

REFERENCE TO PENDING PRIOR PATENT APPLICATIONS

This patent application:

(1) is a continuation-in-part of prior U.S. patent application Ser. No. 10/068,264, filed Feb. 5, 2002 now U.S. Pat. No. 6,656,221 by Daniel C. Taylor et al. for METHOD AND APPARATUS FOR IMPROVING MITRAL VALVE FUNCTION;

(2) is a continuation-in-part of pending prior U.S. patent application Ser. No. 10/112,354, filed Mar. 29, 2002 by John Liddicoat et al. for METHOD AND APPARATUS FOR IMPROVING MITRAL VALVE FUNCTION;

(3) is a continuation-in-part of pending prior U.S. patent application Ser. No. 10/218,649, filed Aug. 14, 2002 by Daniel C. Taylor et al. for METHOD AND APPARATUS FOR IMPROVING MITRAL VALVE FUNCTION;

(4) is a continuation-in-part of prior U.S. patent application Ser. No. 10/280,401, filed Oct. 25, 2002 now U.S. Pat. No. 7,052,487 by William E. Cohn et al. for METHOD AND APPARATUS FOR IMPROVING MITRAL VALVE FUNCTION;

(5) is a continuation-in-part of pending prior U.S. patent application Ser. No. 10/342,034, filed Jan. 14, 2003 by Daniel C. Taylor et al. for METHOD AND APPARATUS FOR REDUCING MITRAL REGURGITATION; and (6) claims benefit of pending prior U.S. Provisional Patent Application Ser. No. 60/391,790, filed Jun. 26, 2002 by William E. Cohn et al. for METHOD AND APPARATUS FOR IMPROVING MITRAL VALVE FUNCTION.

The six (6) aforementioned patent applications are hereby incorporated herein by reference.

FIELD OF THE INVENTION

This invention relates to surgical methods and apparatus in general, and more particularly to surgical methods and apparatus for improving mitral valve function.

BACKGROUND OF THE INVENTION

Mitral valve repair is the procedure of choice to correct mitral regurgitation of all etiologies. With the use of current surgical techniques, between 70% and 95% of regurgitant mitral valves can be repaired. The advantages of mitral valve repair over mitral valve replacement are well documented. These include better preservation of cardiac function and reduced risk of anticoagulant-related hemorrhage, thromboembolism and endocarditis.

In current practice, mitral valve surgery requires an extremely invasive approach that includes a chest wall incision, cardiopulmonary bypass, cardiac and pulmonary arrest, and an incision on the heart itself to gain access to the mitral valve. Such a procedure is associated with high morbidity and mortality. Due to the risks associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction.

Mitral regurgitation is a common occurrence in patients with heart failure and a source of important morbidity and mortality in these patients. Mitral regurgitation in patients with heart failure is caused by changes in the geometric configurations of the left ventricle, papillary muscles and mitral annulus. These geometric alterations result in incomplete coaptation of the mitral leaflets at systole. In this situation, mitral regurgitation is corrected by plicating the mitral valve annulus, either by sutures alone or by sutures in combination with a support ring, so as to reduce the circumference of the distended annulus and restore the original geometry of the mitral valve annulus.

More particularly, current surgical practice for mitral valve repair generally requires that the mitral valve annulus be reduced in radius by surgically opening the left atrium and then fixing sutures, or more commonly sutures in combination with a support ring, to the internal surface of the annulus; this structure is used to cinch the annulus, in a pursestring-like fashion, to a smaller radius, thereby reducing mitral regurgitation by improving leaflet coaptation.

This method of mitral valve repair, generally termed "annuloplasty", effectively reduces mitral regurgitation in heart failure patients. This, in turn, reduces symptoms of heart failure, improves quality of life and increases longetivity. Unfortunately, however, the invasive nature of mitral valve surgery and the attendant risks render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for medical, interventional or surgical therapy.

SUMMARY OF THE INVENTION

As a result, one object of the present invention is to provide an improved method and apparatus for reducing mitral regurgitation.

Another object of the present invention is to provide a method and apparatus for reducing mitral regurgitation which is minimally invasive.

Another object of the present invention is to provide a method and apparatus for reducing mitral regurgitation which can be deployed either permanently (e.g., for patients suffering from heart failure) or temporarily (e.g., for patients suffering from mitral regurgitation with acute myocardial infarction).

These and other objects are addressed by the present invention, which comprises an improved method and apparatus for reducing mitral regurgitation.

In one form of the invention, there is provided a method for reducing mitral regurgitation comprising:

inserting apparatus into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to move at least a portion of the coronary sinus in the vicinity of the posterior leaflet of the mitral valve anteriorly, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to reduce the degree of natural curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to increase the natural radius of curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus having a distal end, a proximal end and an intermediate portion, the apparatus being configured so that when the apparatus is positioned in the coronary sinus in the vicinity of the posterior leaflet of the mitral valve, the distal and proximal ends will apply a posteriorly-directed force to the walls of the coronary sinus and the intermediate portion will apply an anteriorly-directed force to the walls of the coronary sinus, whereby to move the posterior annulus anteriorly and thereby improve leaflet coaptation.

In another form of the invention, there is provided a method for reducing mitral regurgitation comprising:

inserting a substantially straight elongated body into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation.

In another form of the invention, there is provided a method for reducing mitral regurgitation comprising:

inserting a substantially rigid elongated body into the coronary sinus of a patient in the vicinity of the posterior leaflet of the mitral valve, the substantially rigid elongated body being configured relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation.

In another form of the invention, there is provided a method for reducing mitral regurgitation comprising:

inserting a substantially straight, substantially rigid elongated body into the coronary sinus of a patient in the vicinity of the posterior leaflet of the mitral valve, the length of the substantially straight, substantially rigid elongated body being sized relative to the natural curvature of the coronary sinus in the vicinity of the posterior leaflet of the mitral valve so that when the substantially straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation.

In another form of the invention, there is provided an apparatus for reducing mitral regurgitation comprising:

a body having a distal end, a proximal end and an intermediate portion, the body being configured so that when the body is positioned in the coronary sinus in the vicinity of the posterior leaflet of the mitral valve, the distal and proximal ends will apply a posteriorly-directed force to the walls of the coronary sinus, and the intermediate portion will apply an anteriorly-directed force to the walls of the coronary sinus, whereby to move the posterior annulus of the mitral valve anteriorly and thereby improve leaflet coaptation.

In another form of the invention, there is provided an apparatus for reducing mitral regurgitation comprising:

a substantially straight elongated body adapted to be inserted into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

In another form of the invention, there is provided an apparatus for reducing mitral regurgitation comprising:

a substantially rigid elongated body adapted to be inserted into the coronary sinus of a patient in the vicinity of the posterior leaflet of the mitral valve, the substantially rigid elongated body being configured relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation.

In another form of the invention, there is provided an apparatus for reducing mitral regurgitation comprising:

a substantially straight, substantially rigid elongated body adapted to be inserted into the coronary sinus of a patient in the vicinity of the posterior leaflet of the mitral valve, the length of the substantially straight, substantially rigid elongated body being sized relative to the natural curvature of the coronary sinus in the vicinity of the posterior leaflet of the mitral valve so that when the substantially straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation;

the apparatus comprising an elongated body having a degree of curvature, in an unstressed state, which is less than the degree of curvature of the coronary sinus prior to insertion of the elongated body into the coronary sinus, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to move at least a portion of the coronary sinus in the vicinity of the posterior leaflet of the mitral valve anteriorly, whereby to move the posterior annulus anteriorly and thereby improve leaflet coaptation;

the apparatus comprising an elongated body having a straighter configuration, in an unstressed condition, than the coronary sinus prior to insertion of the elongated body into the coronary sinus, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to reduce the degree of natural curvature of at least a portion of the coronary sinus in the vicinity of the posterior leaflet of the mitral valve, whereby to move the posterior annulus anteriorly and thereby improve leaflet coaptation; the apparatus comprising an elongated body having a relatively straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to increase the natural radius of curvature of at least a portion of the coronary sinus in the vicinity of the posterior leaflet of the mitral valve, whereby to move the posterior annulus anteriorly and thereby improve leaflet coaptation;

the apparatus comprising an elongated body having a relatively straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus having a distal end, a proximal end and an intermediate portion, the apparatus being configured so that when the apparatus is positioned in the coronary sinus in the vicinity of the posterior leaflet of the mitral valve, the distal and proximal ends will apply a posteriorly-directed force to the walls of the coronary sinus and the intermediate portion will apply an anteriorly-directed force to the walls of the coronary sinus, whereby to move the posterior annulus anteriorly and thereby improve leaflet coaptation;

the apparatus comprising an elongated body having a relatively straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting a substantially straight elongated body into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation;

the substantially straight elongated body comprising a bar having a substantially straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting a substantially rigid elongated body into the coronary sinus of a patient in the vicinity of the posterior leaflet of the mitral valve, the substantially rigid elongated body being configured relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation;

the substantially rigid elongated body comprising a bar having a relatively straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting a substantially straight, substantially rigid elongated body into the coronary sinus of a patient in the vicinity of the posterior leaflet of the mitral valve, the length of the substantially straight, substantially rigid elongated body being sized relative to the natural curvature of the coronary sinus in the vicinity of the posterior leaflet of the mitral valve so that when the substantially straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation;

the substantially straight, substantially rigid elongated body comprising a bar having a substantially straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided an apparatus for reducing mitral regurgitation comprising:

a body having a distal end, a proximal end and an intermediate portion, the body being configured so that when the body is positioned in the coronary sinus in the vicinity of the posterior leaflet of the mitral valve, the distal and proximal ends will apply a posteriorly-directed force to the walls of the coronary sinus, and the intermediate portion will apply an anteriorly-directed force to the walls of the coronary sinus, whereby to move the posterior annulus of the mitral valve anteriorly and thereby improve leaflet coaptation;

the body comprising a bar having a relatively straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided an apparatus for reducing mitral regurgitation comprising:

a substantially straight elongated body adapted to be inserted into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation;

the body comprising a bar having a substantially straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided an apparatus for reducing mitral regurgitation comprising:

a substantially rigid elongated body adapted to be inserted into the coronary sinus of a patient in the vicinity of the posterior leaflet of the mitral valve, the substantially rigid elongated body being configured relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation;

the body comprising a bar having a substantially straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided an apparatus for reducing mitral regurgitation comprising:

a substantially straight, substantially rigid elongated body adapted to be inserted into the coronary sinus of a patient in the vicinity of the posterior leaflet of the mitral valve, the length of the substantially straight, substantially rigid elongated body being sized relative to the natural curvature of the coronary sinus in the vicinity of the posterior leaflet of the mitral valve so that when the substantially straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation;

the body comprising a bar having a substantially straight configuration in an unstressed condition, and the apparatus being more rigid than the anatomical tissue disposed between the apparatus and the mitral valve, whereby disposition of the apparatus in the coronary sinus will move the posterior annulus anteriorly and improve leaflet coaptation.

In another form of the invention, there is provided a method for reducing mitral regurgitation comprising:

inserting apparatus into the coronary sinus of a patient in the vicinity of the posterior leaflet of the mitral valve, the apparatus being adapted to invert the natural curvature of at least a portion of the coronary sinus in the vicinity of the posterior leaflet of the mitral valve, whereby to move the posterior annulus anteriorly and thereby improve leaflet coaptation, wherein said apparatus comprises a bar and a stabilizing scaffold connected to said bar.

In another form of the invention, there is provided an apparatus for reducing mitral regurgitation comprising:

an elongated body adapted to be inserted into the coronary sinus of a patient in the vicinity of the posterior leaflet of the mitral valve, the apparatus being adapted to invert the natural curvature of at least a portion of the coronary sinus in the vicinity of the posterior leaflet of the mitral valve, whereby to move the posterior annulus anteriorly and thereby improve leaflet coaptation, wherein said apparatus comprises a bar and a stabilizing scaffold connected to said bar.

Significantly, the present invention may be practiced in a minimally invasive manner, either permanently or temporarily, so as to reduce mitral regurgitation.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 8 shows an alternative form of delivery catheter;

FIG. 9 shows an alternative form of flexible push rod;

FIGS. 12–14 show alternative constructions for the elongated body which comprises one form of the present invention;

DETAILED DESCRIPTION OF THE PREFERRED EMBODIMENTS

The coronary sinus is the largest vein in the human heart. During a large portion of its course in the atrioventricular groove, the coronary sinus typically extends adjacent to the left atrium of the heart for a distance of approximately 5 to 10 centimeters. Significantly, for a portion of its length, e.g., typically approximately 7–9 cm, the coronary sinus extends substantially adjacent to the posterior perimeter of the mitral annulus. The present invention takes advantage of this fact. More particularly, by deploying novel apparatus in the coronary sinus, adjacent to the posterior leaflet of the mitral valve, the natural curvature of the coronary sinus may be modified in the vicinity of the posterior leaflet of the mitral valve, whereby to move the posterior annulus anteriorly so as to improve leaflet coaptation and, as a result, reduce mitral regurgitation.

In one preferred embodiment of the present invention, the novel apparatus comprises an elongated body having a substantially straight configuration, the length of the elongated body being sized so that when the elongated body is positioned in the coronary sinus in the vicinity of the posterior leaflet of the mitral valve, the elongated body will cause at least a portion of the coronary sinus to assume a straighter configuration adjacent to the posterior leaflet of the mitral valve, whereby to move the posterior annulus anteriorly and thereby improve leaflet coaptation.

And in one preferred embodiment of the present invention, access to the coronary sinus is gained percutaneously, e.g., the elongated body is introduced into the patient's vascular system via the jugular vein or via the left subclavian vein, passed down the superior vena cava, passed through the right atrium and then passed into the coronary sinus, where it is deployed. Alternatively, the elongated body may be introduced into the coronary sinus through a small incision in the heart, or through some other incision into the patient's vascular system.

And in one preferred embodiment of the present invention, the elongated body is guided into position in the coronary sinus by (i) passing it through a pre-positioned catheter, and/or (ii) passing it over a pre-positioned guidewire, and/or (iii) passing it guide-free (e.g., on the end of a steerable delivery tool) to the surgical site.

Once deployed, the novel apparatus may be left in position permanently (e.g., in the case of patients suffering from mitral regurgitation associated with heart failure) or the novel apparatus may be left in position only temporarily (e.g., in the case of patients suffering from mitral regurgitation associated with acute myocardial infarction).

Visualization of the procedure may be obtained by fluoroscopy, echocardiography, intravascular ultrasound, angioscopy, real-time magnetic resonance imaging, etc. The efficacy of the procedure may be determined through echocardiography, although other imaging modalities may also be suitable.

Figure 1:
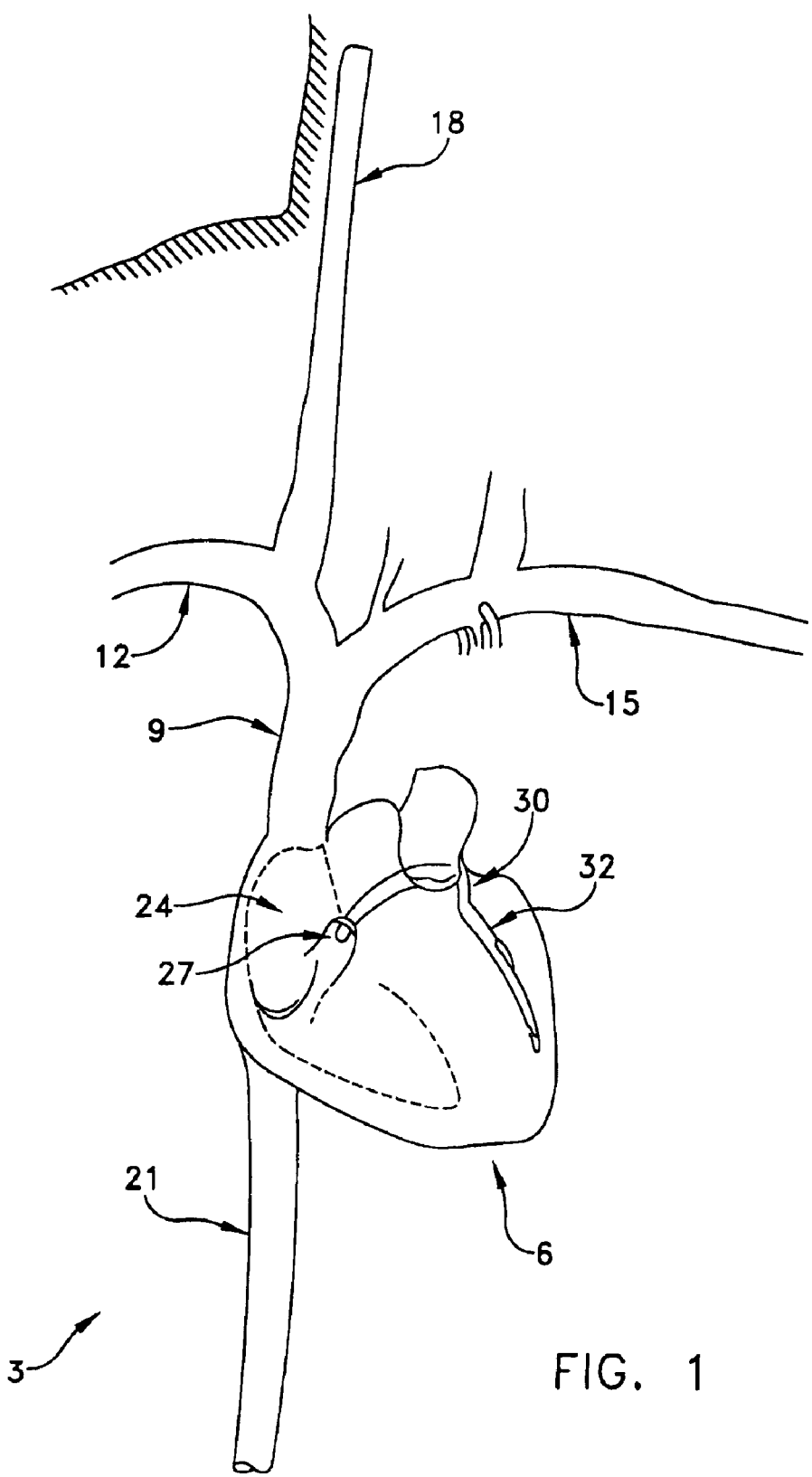
FIG. 1 is a schematic view of portions of the human vascular system.

Looking now at FIG. 1, there are shown aspects of the cardiovascular system 3 of a patient. More particularly, cardiovascular system 3 generally comprises the heart 6, the superior vena cava 9, the right subclavian vein 12, the left subclavian vein 15, the jugular vein 18, and the inferior vena cava 21. Superior vena cava 9 and inferior vena cava 21 communicate with the heart's right atrium 24. The coronary ostium 27 leads to coronary sinus 30. At the far end 31 (FIG. 2) of coronary sinus 30, the vascular structure leads to the vertically-descending anterior interventricular vein ("AIV") 32 (see FIGS. 1 and 2). For the purposes of the present invention, it can generally be convenient to consider the term "coronary sinus" to mean the vascular structure extending between coronary ostium 27 and AIV 32.

Figure 2:
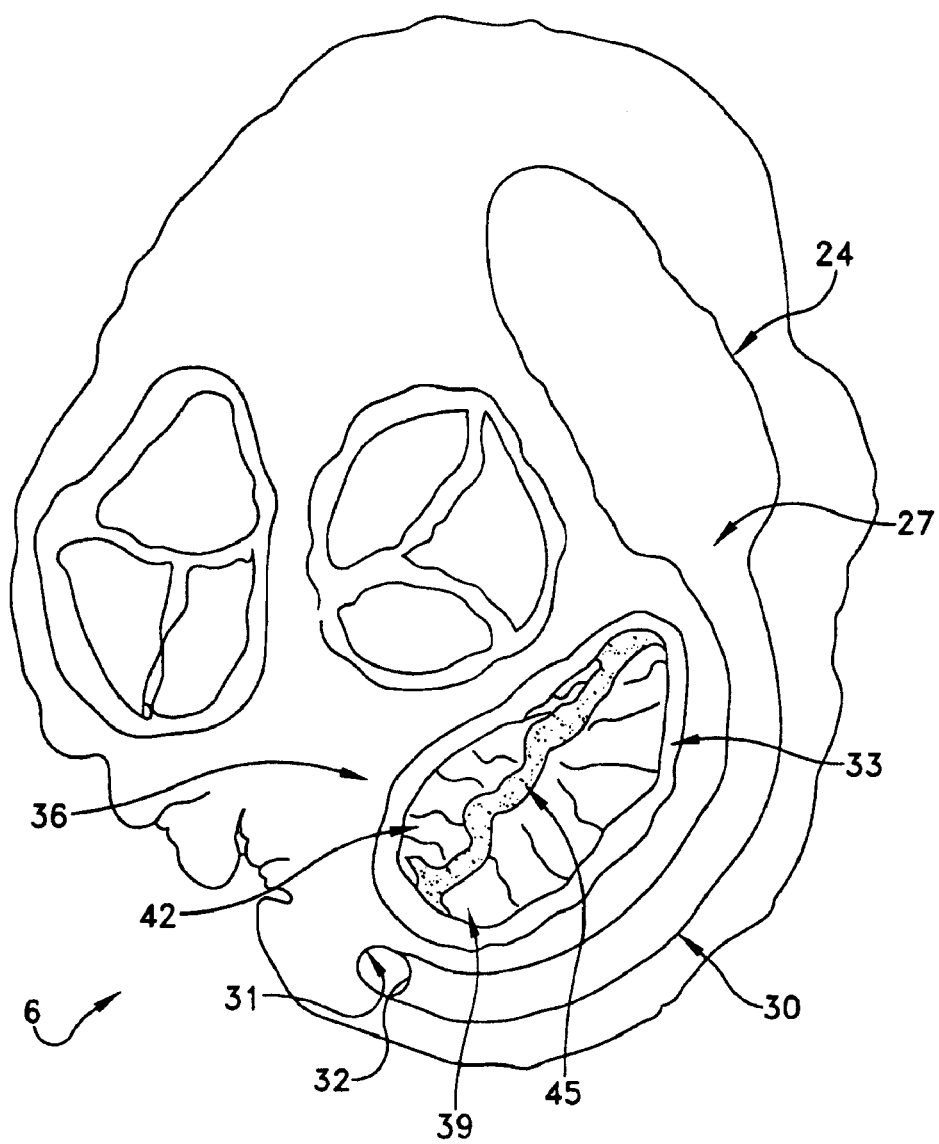
FIG. 2 is a schematic view of portions of the human heart.

As seen in FIG. 2, between coronary ostium 27 and AIV 32, coronary sinus 30 generally extends substantially adjacent to the posterior perimeter of the annulus 33 of the mitral valve 36. Mitral valve 36 comprises a posterior leaflet 39 and an anterior leaflet 42. In the case of a regurgitant mitral valve, posterior leaflet 39 and anterior leaflet 42 will generally fail to properly coapt at systole, thereby leaving an intervening gap 45 which can permit the undesired regurgitation to occur.

Figure 3:
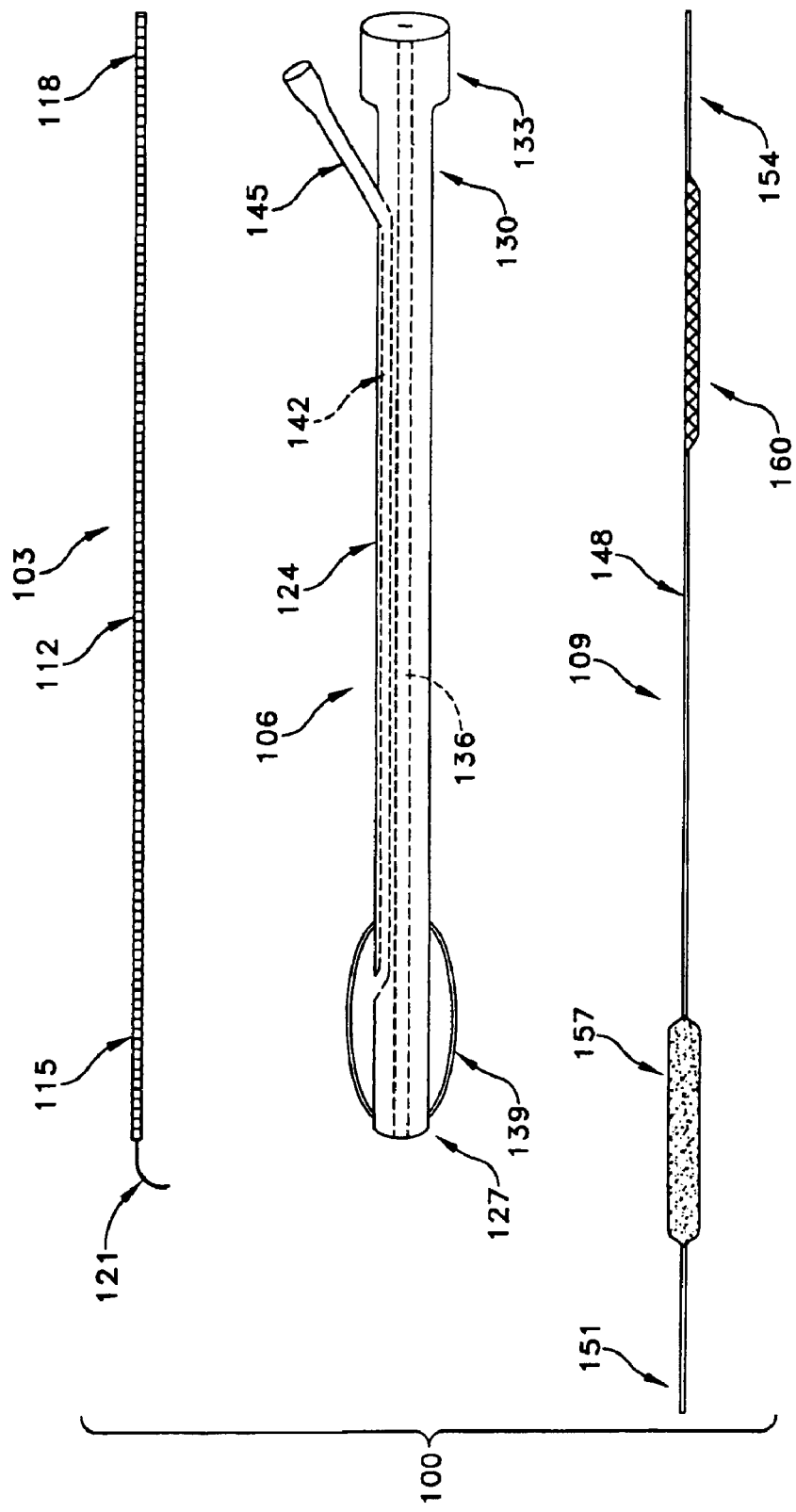
FIG. 3 is a schematic view of a preferred system formed in accordance with the present invention.

Looking next at FIG. 3, there is shown a system 100 which comprises one preferred embodiment of the present invention. More particularly, system 100 generally comprises a guidewire 103, a delivery catheter 106 and a push rod 109.

Guidewire 103 comprises a flexible body 112 having a distal end 115 and a proximal end 118. The distal end 115 of guidewire 103 preferably includes a spring tip 121 for allowing the distal end of guidewire 103 to atraumatically traverse vascular structures, i.e., while the guidewire 103 is being passed through the vascular system of a patient.

Delivery catheter 106 comprises a flexible body 124 having a distal end 127 and a proximal end 130, preferably with an adjustable valve 133 attached. A central lumen 136 extends from distal end 127 to proximal end 130. In some circumstances it may be desirable to provide a securing mechanism for securing the distal end 127 of the delivery catheter 106 within a vascular structure. By way of example but not limitation, an inflatable balloon 139 may be positioned about the exterior of flexible body 124, just proximal to distal end 127, with an inflation lumen 142 extending between balloon 139 and an inflation fitting 145.

Push rod 109 comprises a flexible body 148 having a distal end 151 and a proximal end 154. A substantially straight, substantially rigid elongated body 157, which may have a variety of different lengths, is formed on flexible body 148, proximal to distal end 151. A removable proximal stiffener (or handle) 160 may be placed between elongated body 157 and proximal end 154 so as to facilitate the manual gripping of flexible body 148, e.g., for advancement or retraction purposes.

System 100 may be used as follows to reduce mitral regurgitation.

Figure 4:
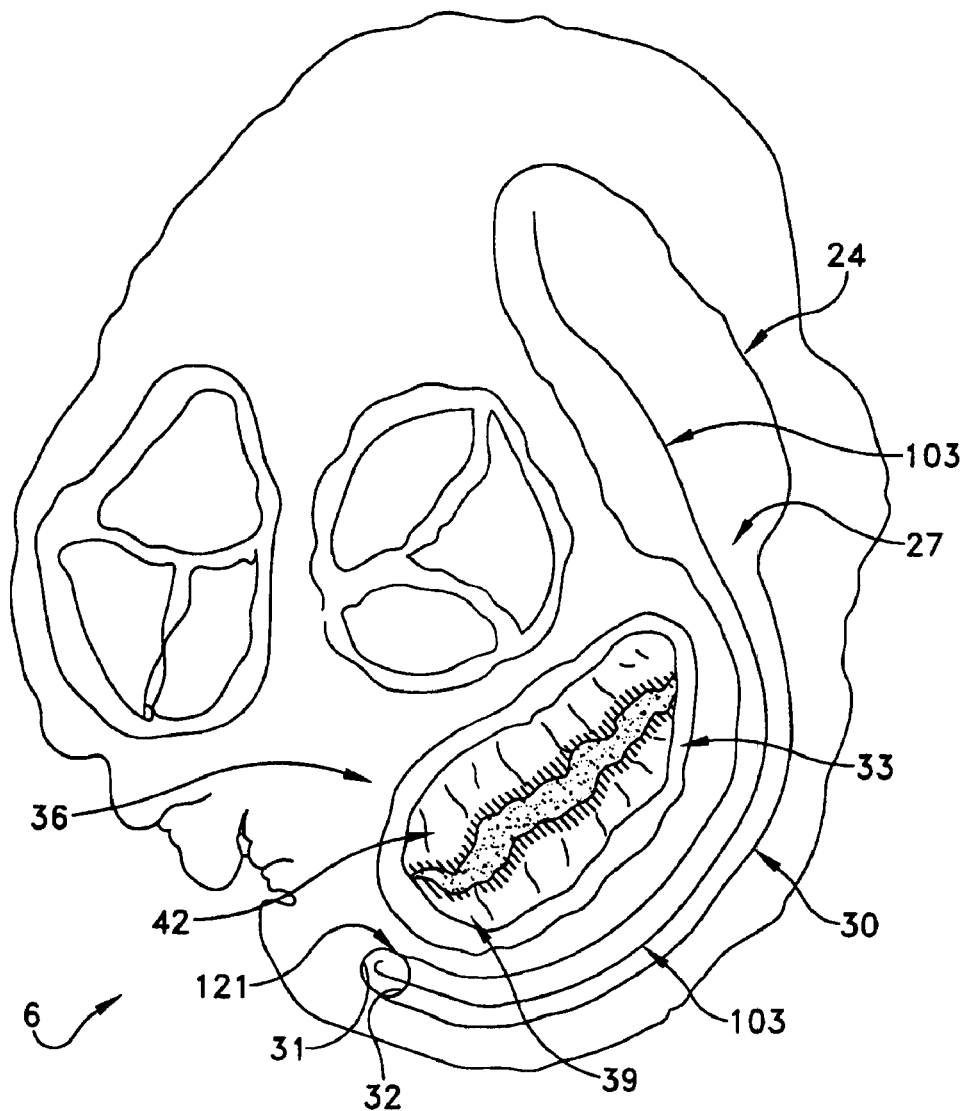
FIGS. 4–7 are a series of views illustrating use of the system of FIG. 3 to reduce mitral regurgitation.

First, distal end 115 of guidewire 103 is passed down the jugular vein 18 (or the left subclavian vein 15) of a patient, down superior vena cava 9, through right atrium 24 of the heart, and then along coronary sinus 30. See FIG. 4. It will be appreciated that as flexible guidewire 103 is passed down coronary sinus 30, the guidewire will tend to assume the natural curved shape of the coronary sinus, due to the flexible nature of the guidewire. The guidewire's atraumatic spring tip 121 will help ensure minimal damage to vascular structures as guidewire 103 is maneuvered into position.

Figure 5:
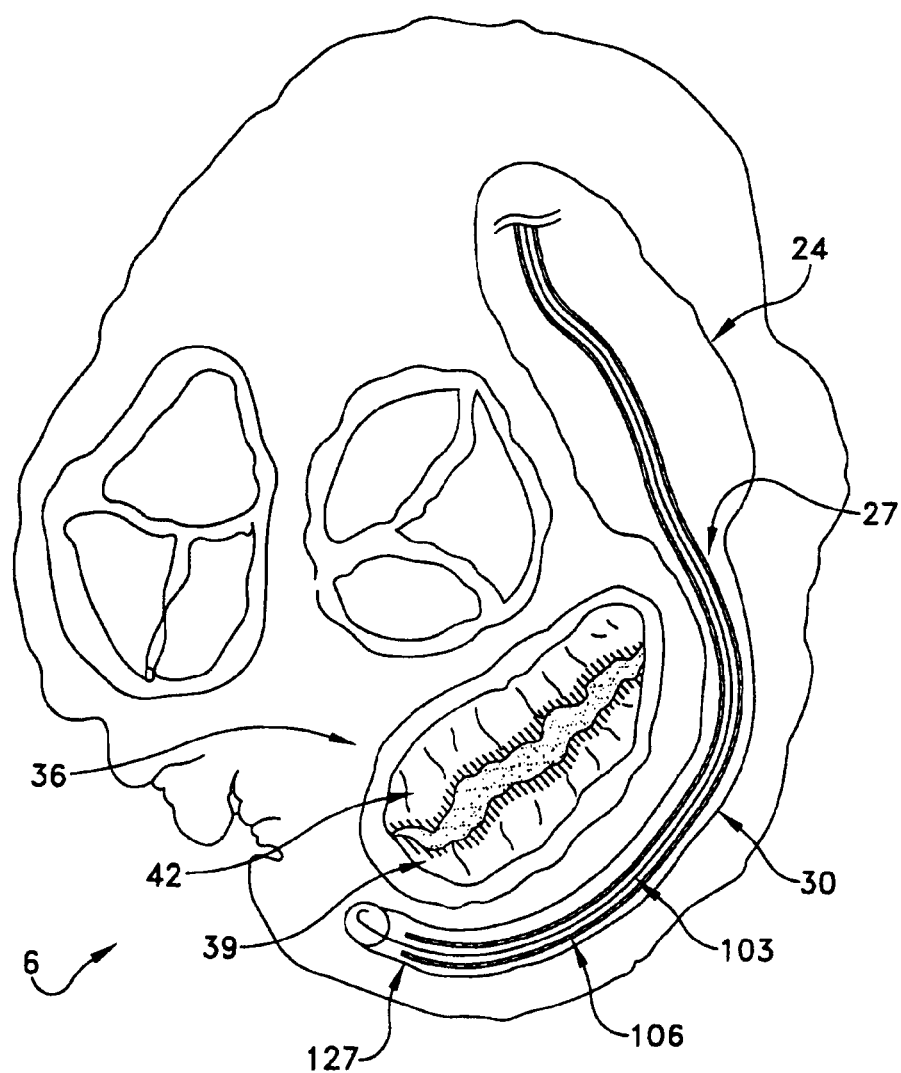

Next, distal end 127 of delivery catheter 106 is placed over proximal end 118 of guidewire 103 and passed down the guidewire until the distal end 127 of the delivery catheter 106 is positioned in coronary sinus 30. See FIG. 5. Again, it will be appreciated that as the flexible delivery catheter 106 passes down the coronary sinus, the delivery catheter will tend to assume the natural curved shape of the coronary sinus, due to the flexible nature of the delivery catheter.

Figure 6:
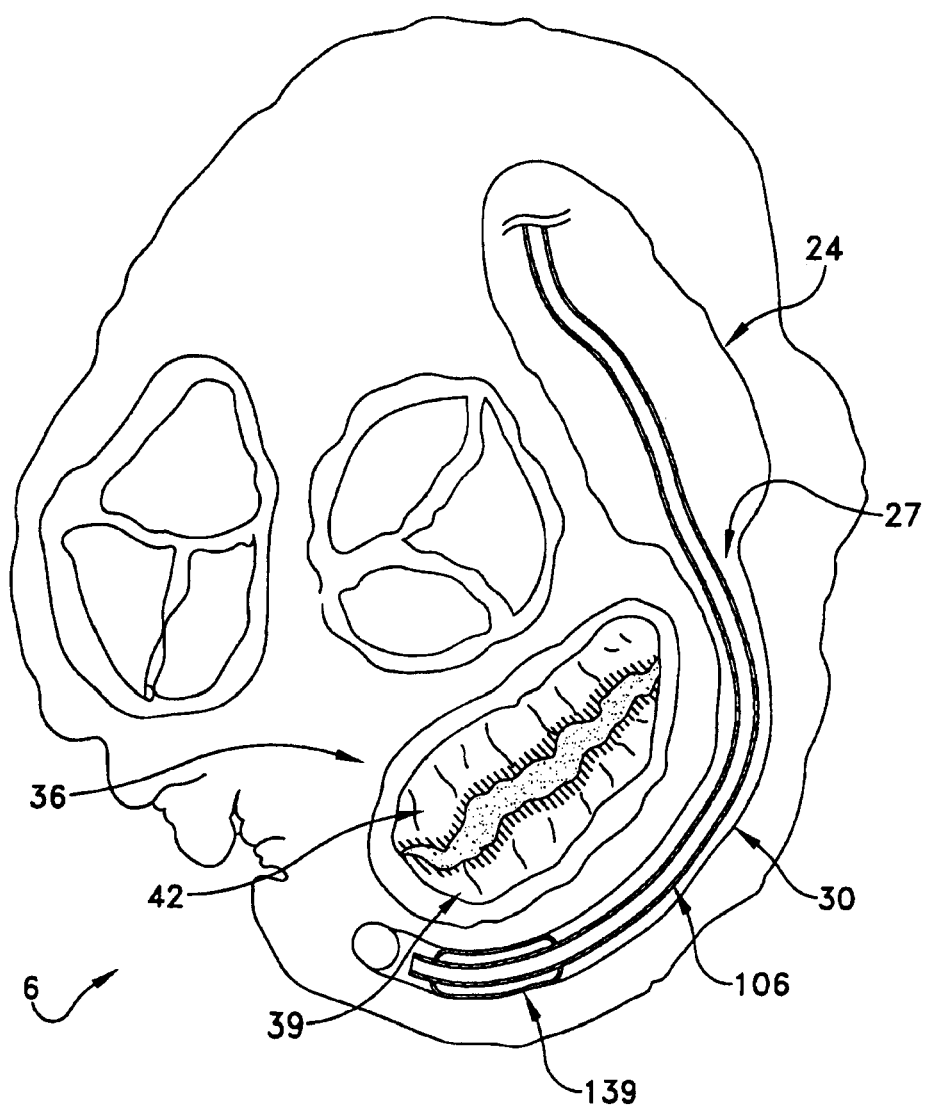

Once delivery catheter 106 has been positioned within the coronary sinus, guidewire 103 is removed. See FIG. 6. Either before or after guidewire 103 is removed, balloon 139 may be inflated so as to secure the distal end 127 of delivery catheter 106 in position within coronary sinus 30.

Figure 7:
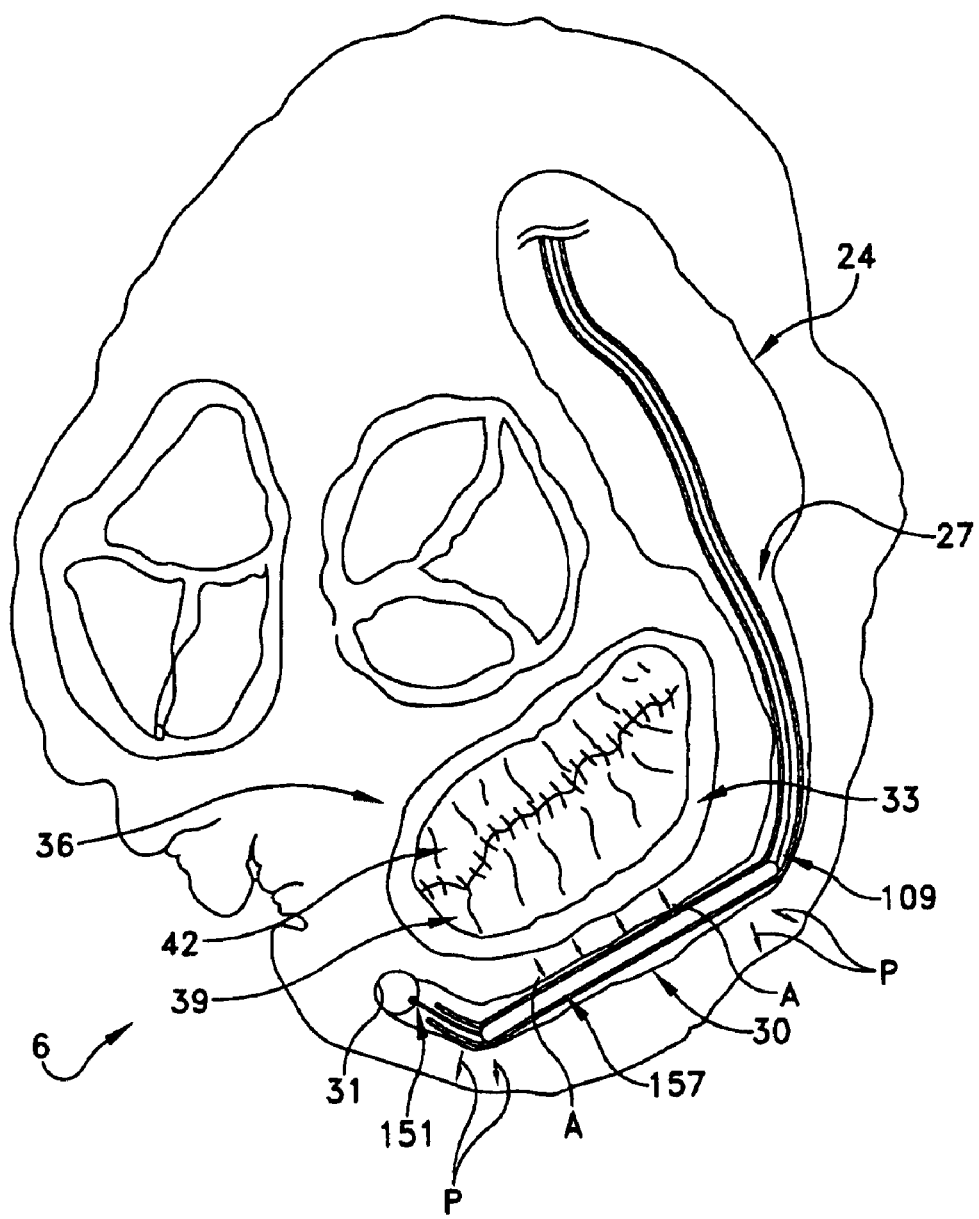

Next, push rod 109 is passed down the central lumen 136 of delivery catheter 106. As the push rod's substantially straight, substantially rigid elongated body 157 is passed down central lumen 136 of delivery catheter 106, the substantially straight, substantially rigid elongated body 157 will force the delivery catheter 106 to assume a substantially straight configuration at the point where the substantially straight, substantially rigid elongated body 157 currently resides (FIG. 7). As push rod 109 is pushed down delivery catheter 106, balloon 139 will act to hold the distal end 127 of the delivery catheter 106 in position within coronary sinus 30.

Push rod 109 is pushed down delivery catheter 106, utilizing proximal handle 160 (FIG. 3) as needed, until the substantially straight, substantially rigid elongated body 157 is located adjacent to the posterior annulus 33 of mitral valve 36. See FIG. 7. As this occurs, the presence of the substantially straight, substantially rigid elongated body 157 within delivery catheter 106 will cause at least a portion of coronary sinus 30 to assume a substantially straight configuration at this point, so that the posterior annulus 33 of mitral valve 36 is forced anteriorly. This will cause the mitral valve's posterior leaflet 39 to also move anteriorly so as to improve mitral valve leaflet coaptation and thereby reduce (or completely eliminate) mitral valve regurgitation. In this respect it should be appreciated that the posterior annulus may be shifted anteriorly so as to achieve, or to attempt to achieve to the extent anatomically possible, leaflet-to-leaflet engagement or leaflet-to-annulus engagement (e.g., where a leaflet may be tethered due to left ventricular distortion). Both of these types of engagement, or targeted engagement, are intended to be encompassed by the terms "improved leaflet coaptation" and/or "increased leaflet coaptation" and the like. Using standard visualization means (e.g. echocardiography and/or fluoroscopy), the exact position of the substantially straight, substantially rigid elongated body 157 is adjusted so as to reduce (or completely eliminate) regurgitation in mitral valve 36.

In this respect it should be appreciated that the substantially straight, substantially rigid elongated body 157 is preferably sized so as to be somewhat less than the length of the coronary sinus between coronary ostium 27 and AIV 32. However, in some circumstances it may be desirable to size the substantially straight, substantially rigid elongated body 157 so that it will extend out of the coronary sinus 30 and into the right atrium 24.

Furthermore, it should also be appreciated that the system provides a degree of tactile feedback to the user during deployment. More particularly, substantial resistance will typically be encountered as the substantially straight, substantially rigid elongated body 157 is pushed out of right atrium 24 and into coronary sinus 30; then resistance will typically drop as body 157 is moved through the coronary sinus; and then resistance will typically increase significantly again as the distal end 151 (FIG. 3) of push rod 109, and/or the leading distal tip of body 157, comes to the far end 31 of the coronary sinus. Thus, there is something of a tactile "sweet spot" when the substantially straight, substantially rigid elongated body 157 is located in the coronary sinus between coronary ostium 27 and AIV 32, and this tactile "sweet spot" can be helpful to the user in properly positioning the substantially straight, substantially rigid elongated body 157 in coronary sinus 30.

At this point in the procedure, the substantially straight, substantially rigid elongated body 157 is locked in position, e.g., by closing the delivery catheter's adjustable valve 133 (FIG. 3), and balloon 139 may be deflated.

System 100 (less guidewire 103, which was previously removed) is left in this position until it is no longer needed. In some cases (e.g., in the case of patient suffering from mitral regurgitation associated with acute myocardial infarction), this may mean that system 100 is left in position for a period of hours, days or weeks. In other cases (e.g., in the case of patient suffering from mitral regurgitation associated with heart failure), system 100 may be substantially permanent. If and when system 100 is to be removed, push rod 109 is removed from delivery catheter 106, and then delivery catheter 106 is removed from the patient.

Thus it will be seen that with the present invention, the substantially straight, substantially rigid elongated body 157 is essentially force-fit into the normally curved portion of the coronary sinus adjacent to the mitral valve's posterior leaflet. By properly sizing the length of the substantially straight, substantially rigid elongated body 157 relative to the natural curvature of the patient's anatomy, and by properly positioning the substantially straight, substantially rigid elongated body 157 in the patient's coronary sinus, the substantially straight, substantially rigid elongated body will cause at least a portion of the coronary sinus to assume a substantially straight configuration adjacent to the posterior leaflet 39 of the mitral valve 36. This action will in turn drive the posterior annulus of the mitral valve anteriorly, so as to improve leaflet coaptation and thereby reduce mitral regurgitation. Thus, by inserting the substantially straight, substantially rigid elongated body 157 into the coronary sinus 30 adjacent to the posterior leaflet 39 of the mitral valve 36, the annulus 33 of the mitral valve is effectively manipulated so that it will assume an increased radius of curvature.

As noted above, by properly sizing the length of the substantially straight, substantially rigid elongated body 157 relative to the natural curvature of the patient's anatomy, and by properly positioning the substantially straight, substantially rigid elongated body 157 in the patient's coronary sinus, the substantially straight, substantially rigid elongated body 157 will cause at least a portion of the coronary sinus to assume a substantially straight configuration adjacent to the posterior leaflet 39 of the mitral valve 36, whereby to drive the posterior annulus of the mitral valve anteriorly, so as to improve leaflet coaptation and thereby reduce mitral regurgitation. To this end, push rod 109 is preferably provided as part of a kit having a plurality of different push rods 109, each with a differently-sized elongated body 157, whereby a physician may select and deploy the appropriately-sized elongated body 157 for a specific patient's anatomy. Furthermore, if upon deployment it should be discovered (e.g., under echocardiography and/or fluoroscopy) that a different size of elongated body 157 is needed, the first push rod 109 may be replaced by a second push rod 109 having the desired size of elongated body 157.

In one preferred form of the invention, a diagnostic push rod 109 may first be inserted into the coronary sinus of the patient for the purpose of initially determining the appropriate length of elongated body 157 for that particular patient's anatomy; again, a series of differently-sized diagnostic push rods 109 may be sequentially inserted into the patient's coronary sinus so as to determine the preferred size for the elongated body 157. Thereafter, an appropriately-sized therapeutic push rod 109 may be inserted into the coronary sinus so as to improve leaflet coaptation and thereby reduce mitral regurgitation.

Furthermore, prior to inserting a diagnostic push rod 109 into the coronary sinus of the patient, the doctor may make a preliminary assessment of the size of the coronary sinus for the purpose of determining an initial estimated length for the elongated body 157 of diagnostic push rod 109. This may be done under fluoroscopy using a guidewire 103 having radioopaque markers thereon, or by using a delivery catheter 106 having radioopaque markers thereon, or by inserting another device (e.g., a flexible element) into the coronary sinus, where that device has radioopaque markers thereon, or in other ways which will be apparent to those skilled in the art. Using the radioopaque markers, the doctor makes a preliminary assessment of the size of the coronary sinus, whereby to determine an initial estimated length for the elongated body 157 of diagnostic push rod 109; the diagnostic push rod 109 is then switched out as needed until the proper length of elongated body 157 is determined, whereupon the appropriately-sized diagnostic push rod is replaced by the therapeutic push rod 109.

It has also been found that by inserting the substantially straight, substantially rigid elongated body 157 into the coronary sinus adjacent to the posterior leaflet of the mitral valve, the patient's left ventricle may also be remodeled so as to help alleviate congestive heart failure.

It is significant to note that with the present invention, the distal and proximal ends of the substantially straight, substantially rigid elongated body 157 apply a posteriorly-directed force on the walls of coronary sinus 30 (e.g., as shown with arrows P in FIG. 7), while the intermediate portion of the substantially straight, substantially rigid elongated body 157 applies an anteriorly-directed force on the walls of coronary sinus 30 (e.g., as shown with arrows A in FIG. 7).

In some cases the proximal end 130 (FIG. 3) of delivery catheter 106 may be fixed to the patient's outer skin using standard patient care methods such as adhesive tape, purse-string sutures, skin staples, etc. In other cases proximal end 130 of delivery catheter 106 may include a sewing cuff whereby the delivery catheter may be secured to the patient's tissue by suturing. See, for example, FIG. 8, where a sewing cuff 166 is shown attached to the proximal end 130 of delivery catheter 106. If desired, an element 169 may be provided proximal to adjustable valve 133, whereby flexible push rod 109 may be made fast to delivery catheter 106 without using adjustable valve 133 (FIG. 3). By way of example, element 169 may comprise a crimpable element to secure flexible push rod 109 to delivery catheter 106, which is in turn secured to the patient, e.g., with sewing cuff 166. If desired, the proximal end of the assembly may be embedded under the skin of the patient, e.g., in the case of a permanent implant.

As noted above, it can be helpful to anchor the distal end of delivery catheter 106 in position within the coronary sinus prior to pushing push rod 109 into the delivery catheter. Such an arrangement will keep the delivery catheter in place as the substantially straight, substantially rigid elongated body 157 makes the turn within the right atrium and enters the coronary sinus. In the absence of such anchoring, the push rod may drive the delivery catheter down the inferior vena cava 21. More particularly, by securing the distal end of delivery catheter 106 to the walls of coronary sinus 30, the delivery catheter can be stabilized against diversion down the inferior vena cava 21 when the substantially straight, substantially rigid elongated body 157 encounters initial resistance to making the turn into the coronary sinus. The balloon 139 is one way of accomplishing such anchoring. However, it is also possible to utilize other types of securing mechanisms to anchor the distal end 127 of delivery catheter 106 in position within coronary sinus 30, e.g., spring clips, ribs, etc.

If desired, the distal end 151 of push rod 109 may itself be provided with a distal anchor, e.g., such as the distal anchor 172 shown in FIG. 9. Such a distal anchor on push rod 109 can help hold the substantially straight, substantially rigid elongated body 157 in proper position within coronary sinus 30.

Figure 10:
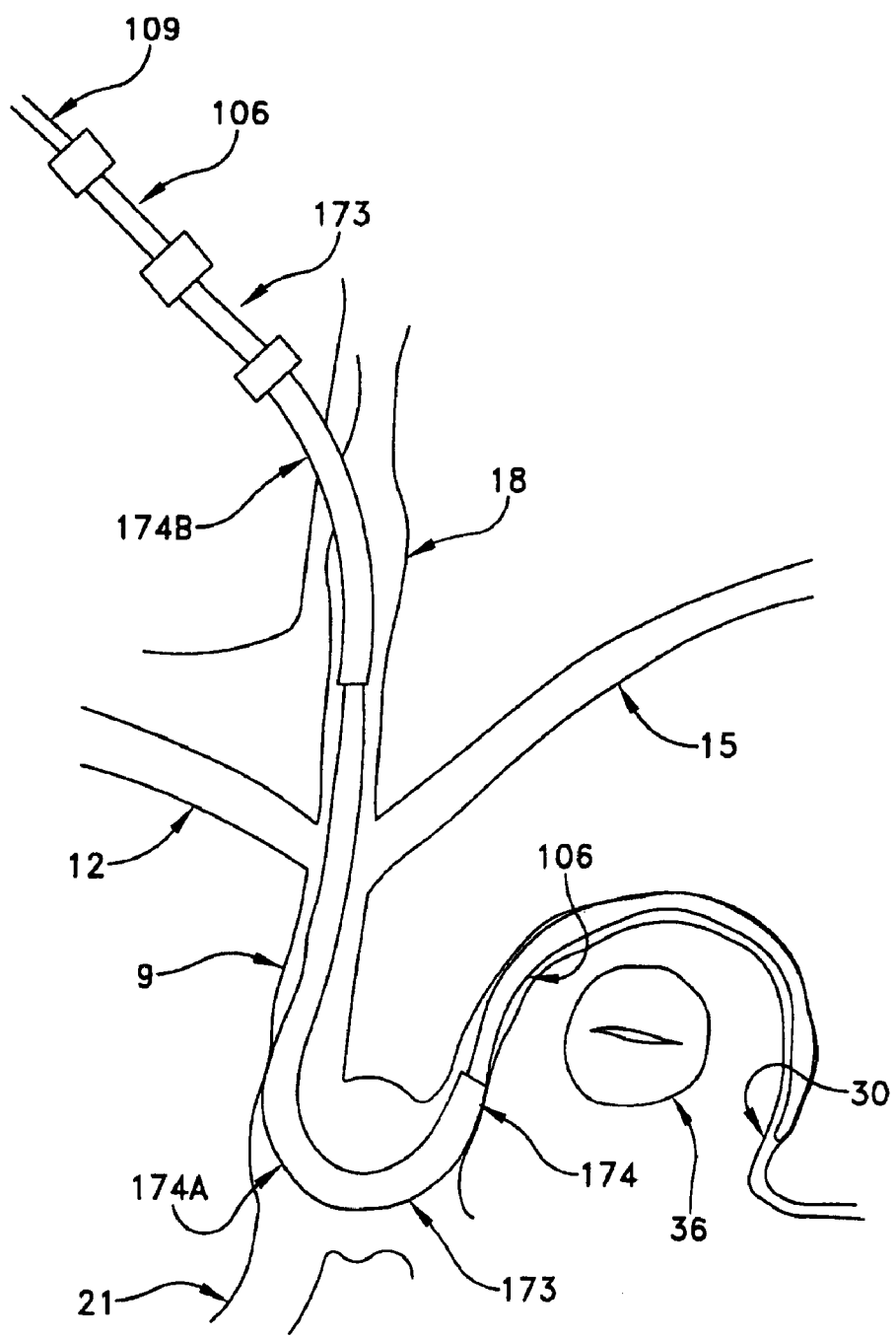
FIG. 10 shows another alternative form of the present invention.

It is also possible to prevent diversion of delivery catheter 106 down inferior vena cava 21 without anchoring the distal end of delivery catheter 106 to the walls of the coronary sinus. More particularly, and looking now at FIG. 10, there is shown a support catheter 173 which is formed out of a more rigid material than the flexible body 124 of delivery catheter 106. Support catheter 173 is constructed so that its distal end 174 can be positioned in coronary ostium 27 and then its sidewall 174A can support delivery catheter 106 adjacent to inferior vena cava 21 when push rod 109 is passed down delivery catheter 106, whereby to prevent delivery catheter 106 from diverting down inferior vena cava 106. FIG. 10 also shows an introducer catheter 174B at the entrance to jugular vein 18.

Figure 11:
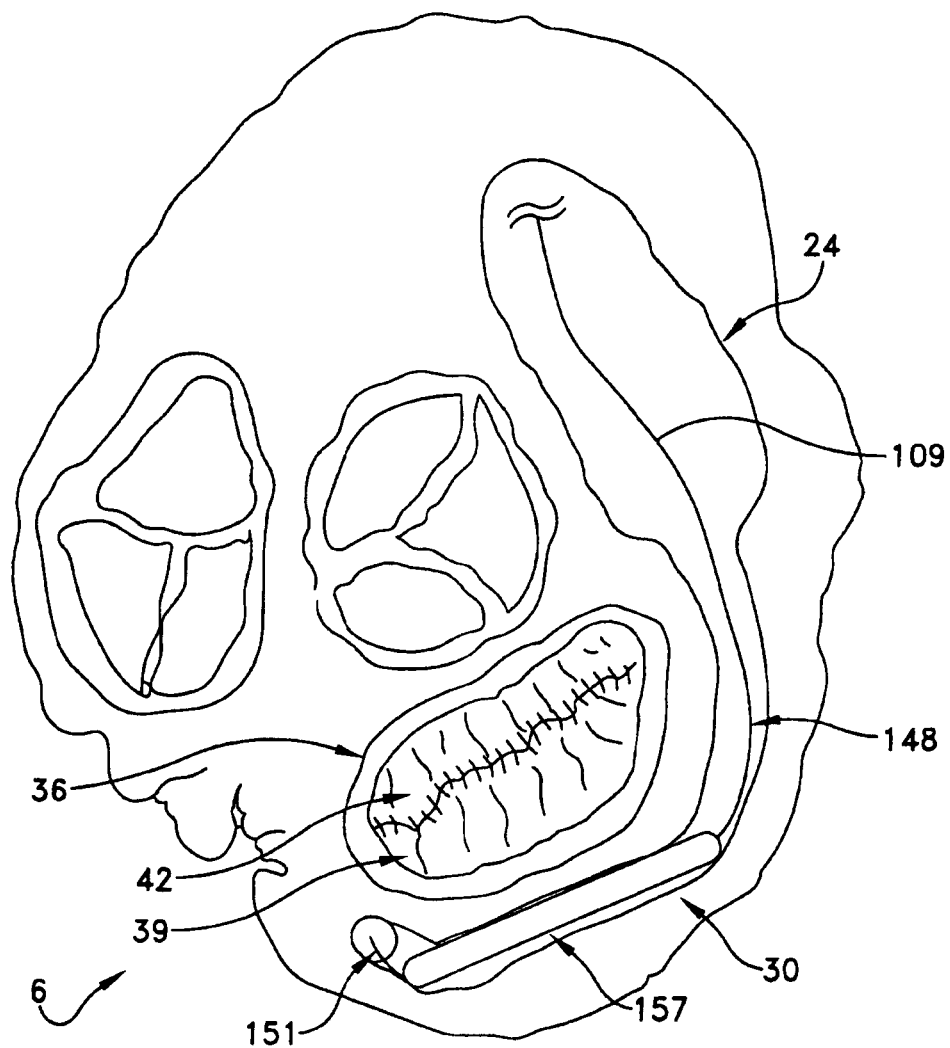
FIG. 11 shows another alternative form of the present invention.

In the preceding discussion of system 100, push rod 109 is described as being advanced to the surgical site through the delivery catheter 106 and remaining within delivery catheter 106 while at the surgical site and, when push rod 109 is to be removed, removing push rod 109 and then delivery catheter 106. However, if desired, once push rod 109 has been deployed at the surgical site, delivery catheter 106 may then be removed, leaving just push rod 109 at the surgical site. See, for example, FIG. 11.

It is also possible to advance push rod 109 directly to the surgical site without passing it through a delivery catheter; in this case, push rod 109 would be advanced on its own through the intervening vascular structure until it is deployed in coronary sinus 30.

As noted above, as push rod 109 is advanced to the region adjacent to the posterior annulus of the mitral valve, the substantially straight, substantially rigid elongated body 157 will distort the natural configuration of the coronary sinus so that it will assume a substantially straight configuration. While this action induces the desired valve remodeling, it can also induce a significant stress on the walls of the coronary sinus, particularly at the distal and proximal ends of the substantially straight, substantially rigid elongated body 157, where stress will be concentrated (see the arrows P in FIG. 7). To this end, the construction of the substantially straight, substantially rigid elongated body 157 may be modified somewhat so as to better distribute this stress.

More particularly, and looking next at FIG. 12, the distal and proximal ends of substantially straight, substantially rigid elongated body 157 may include relatively flexible portions 175 to help better distribute the stress exerted on the walls of the coronary sinus. Additionally, and/or alternatively, any taper applied to the distal and proximal ends of substantially straight, substantially rigid elongated body 157 may be elongated, e.g., such as shown at 178 in FIG. 13, so as to better distribute the stress imposed on the walls of the coronary sinus. In one preferred form of the invention, and looking now at FIG. 14, the substantially straight, substantially rigid elongated body 157 may have relatively long relatively flexible portions 175 with relatively elongated tapers 178. If desired, each of the relatively long, relatively flexible portions 175 with relatively elongated tapers 178 may be as long as, or longer than, the substantially straight, substantially rigid intermediate portion of elongated body 157.

Figure 15:
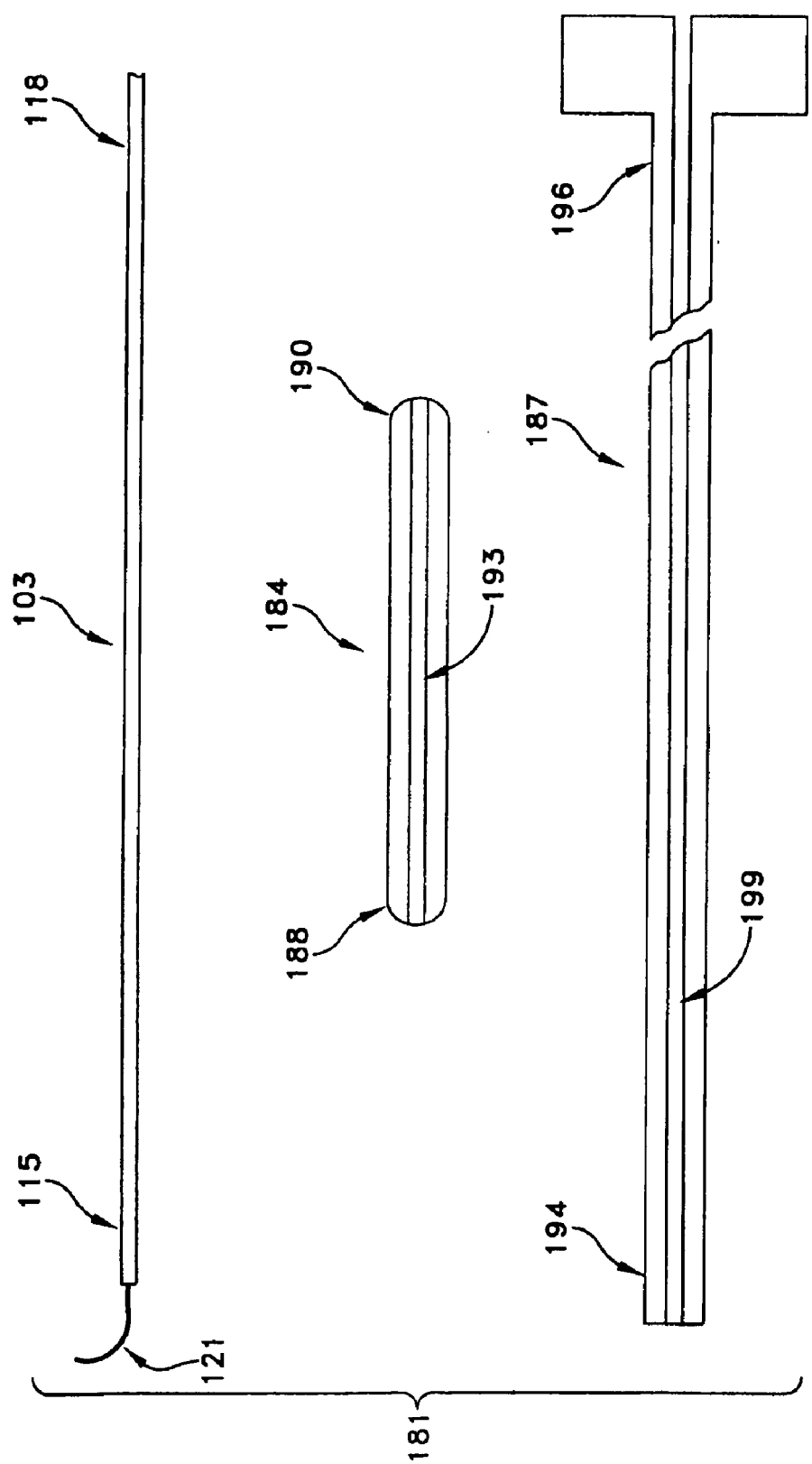
FIG. 15 shows an alternative system formed in accordance with the present invention.

Looking next at FIG. 15, there is shown a system 181 which comprises another preferred embodiment of the present invention. More particularly, system 181 generally comprises the guidewire 103, a substantially straight, substantially rigid elongated body 184 and a push cannula 187.

Guidewire 103 is as previously described.

Substantially straight, substantially rigid elongated body 184, which is provided in a variety of different lengths, comprises a distal end 188 and a proximal end 190. A central lumen 193 extends between distal end 188 and proximal end 190. Central lumen 193 accommodates guidewire 103.

Push cannula 187 comprises a distal end 194 and a proximal end 196. A central lumen 199 extends between distal end 194 and proximal end 196. Central lumen 199 accommodates guidewire 103.

System 181 may be used as follows to reduce mitral regurgitation.

First, distal end 115 of guidewire 103 is passed down jugular vein 18 (or the left subclavian vein 15) of a patient, down superior vena cava 9, through right atrium 24 of the heart, and along coronary sinus 30. It will be appreciated that as flexible guidewire 103 is passed down coronary sinus 30, the guidewire will tend to assume the natural curved shape of the coronary sinus, due to the flexible nature of the guidewire. The guidewire's atraumatic spring tip 121 will help minimize damage to vascular structures as the guidewire is advanced into position.

Figure 16:
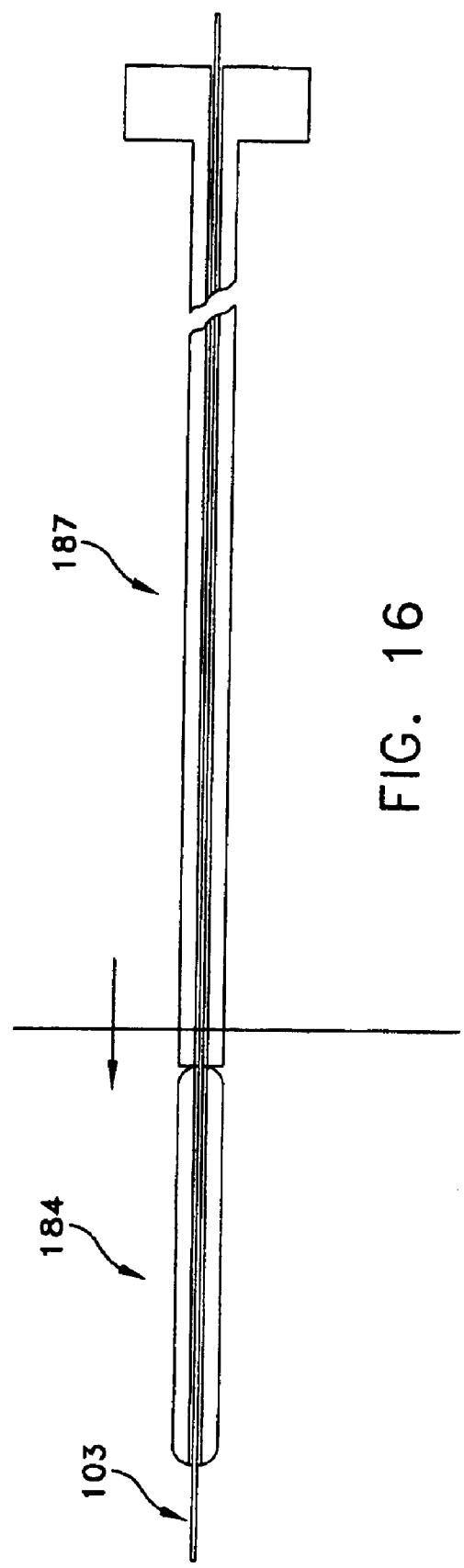
FIG. 16 shows how the system of FIG. 15 is configured during deployment of the system's elongated body.

Next, distal end 188 of substantially straight, substantially rigid elongated body 184 is placed over proximal end 118 of guidewire 103 and passed a short distance down the guidewire. Then the distal end 194 of push cannula 187 is placed over proximal end 118 of guidewire 103, and then push cannula 187 is advanced down the guidewire. As push cannula 187 is advanced down the guidewire, its distal end 194 pushes the substantially straight, substantially rigid elongated body 184 ahead of it. See FIG. 16.

As the substantially straight, substantially rigid elongated body 184 is passed down the coronary sinus, it will force the coronary sinus to assume a substantially straight configuration at the point where the substantially straight, substantially rigid elongated body 184 currently resides. Push cannula 187 is pushed down guidewire as needed, until the substantially straight, substantially rigid elongated body 184 is located adjacent to the posterior annulus of the mitral valve. As this occurs, the presence of the substantially straight, substantially rigid elongated body 184 in the coronary sinus will cause the coronary sinus to assume a substantially straight configuration at this point, so that the posterior annulus of the mitral valve is forced anteriorly. This will cause the posterior mitral valve leaflet to also move anteriorly so as to improve leaflet coaptation and thereby reduce (or completely eliminate) mitral valve regurgitation. Using standard visualization means (e.g. echocardiography and/or fluoroscopy), the exact position of the substantially straight, substantially rigid elongated body may be adjusted so as to reduce (or completely eliminate) regurgitation in the mitral valve.

If desired, the push cannula 187 may be provided with a releasably attachable interface (e.g., a grasper) so that it may releasably secure the proximal end 190 of the substantially straight, substantially rigid elongated body 184. Such a feature will permit the substantially straight, substantially rigid elongated body to be pulled backward within the coronary sinus, either for positioning or removal purposes.

Thus it will be seen that with the present invention, the substantially straight, substantially rigid elongated body 184 is essentially force-fit into the normally curved portion of the coronary sinus adjacent to the mitral valve's posterior leaflet. By properly sizing the length of the substantially straight, substantially rigid elongated body 184 relative to the natural curvature of the patient's anatomy, and by properly positioning the substantially straight, substantially rigid elongated body 184 in the patient's coronary sinus, the substantially straight, substantially rigid elongated body 184 will cause at least a portion of the coronary sinus to assume a substantially straight configuration adjacent to the posterior leaflet 39 of the mitral valve 36. This action will in turn drive the posterior annulus of the mitral valve anteriorly, so as to improve leaflet coaptation and thereby reduce mitral regurgitation. Thus, by inserting the substantially straight, substantially rigid elongated body 184 into the coronary sinus 30 adjacent to the posterior leaflet 39 of the mitral valve 36, the annulus 33 of the mitral valve is effectively manipulated so that it will assume an increased radius of curvature.

As noted above, by properly sizing the length of the substantially straight, substantially rigid elongated body 184 relative to the natural curvature of the patient's anatomy, and by properly positioning the substantially straight, substantially rigid elongated body 184 in the patient's coronary sinus, the substantially straight, substantially rigid elongated body 184 will cause at least a portion of the coronary sinus to assume a substantially straight configuration adjacent to the posterior leaflet 39 of the mitral valve 36, whereby to drive the posterior annulus of the mitral valve anteriorly, so as to improve leaflet coaptation and thereby reduce mitral regurgitation. To this end, the substantially straight, substantially rigid elongated body 184 is preferably provided as part of a kit having a plurality of different substantially straight, substantially rigid elongated bodies 184, each with a differently-sized elongated body 184, whereby a physician may select and deploy the appropriately-sized elongated body 184 for a specific patient's anatomy. Furthermore, if upon deployment it should be discovered (e.g., under echocardiography and/or fluoroscopy) that a different size of elongated body 184 is needed, the first elongated body 184 may be replaced by a second elongated body 184 having the size needed to achieve the desired therapeutic result.

In one preferred form of the invention, a diagnostic elongated body 184 may first be inserted into the coronary sinus of the patient for the purpose of initially determining the appropriate length of elongated body 184 for that particular patient's anatomy; again, a series of differently-sized diagnostic elongated bodies may be sequentially inserted into the patient's coronary sinus so as to determine the preferred size of the therapeutic elongated body 184. Thereafter, an appropriately-sized therapeutic elongated body 184 may be inserted into the coronary sinus so as to improve leaflet coaptation and thereby reduce mitral regurgitation.

Furthermore, prior to inserting a diagnostic elongated body 184 into the coronary sinus of the patient, the doctor may make a preliminary assessment of the size of the coronary sinus for the purpose of determining an initial estimated length for the diagnostic elongated body 184. This may be done under fluoroscopy using a guidewire 103 having radioopaque markers thereon, or by inserting another device (e.g., a flexible element) into the coronary sinus, where that device has radioopaque markers thereon, or in other ways which will be apparent to those skilled in the art. Using the radioopaque markers, the doctor makes a preliminary assessment of the size of the coronary sinus, whereby to determine an initial estimated length for the diagnostic elongated body 184; the diagnostic elongated body 184 is then switched out as needed until the proper length of diagnostic elongated body 184 is determined, whereupon the appropriately-sized diagnostic elongated body 184 is replaced by the therapeutic elongated body 184.

As also noted above, as the substantially straight, substantially rigid elongated body 184 is advanced to the region adjacent to the posterior annulus of the mitral valve, the substantially straight, substantially rigid elongated body 184 will distort the natural configuration of the coronary sinus so that it will assume a substantially straight configuration. While this action induces the desired valve remodeling, it can also induce a significant stress on the walls of the coronary sinus, particularly at the distal and proximal ends of the substantially straight, substantially rigid elongated body 184, where stress will be concentrated (see, for example, the arrows P in FIG. 7). To this end, the construction of the substantially straight, substantially rigid elongated body 184 may be modified somewhat so as to better distribute this stress.

Figure 17:
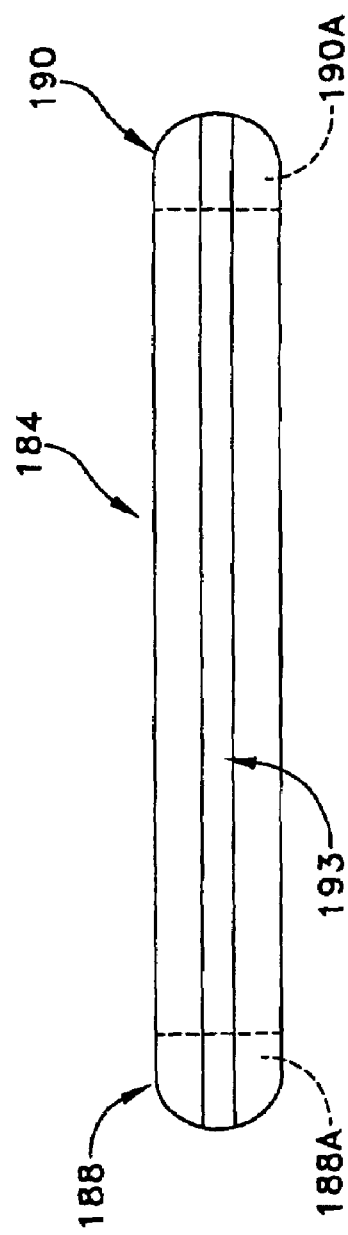
FIGS. 17–19 are side elevational views of further alternative embodiments of the elongated body.
Figure 18:
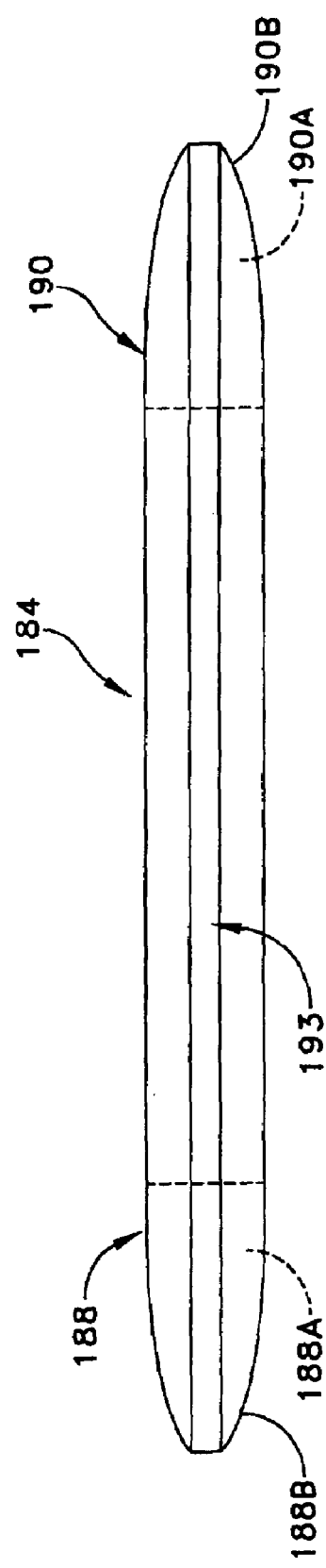

More particularly, and looking next at FIG. 17, the distal and proximal ends of substantially straight, substantially rigid elongated body 184 may include relatively flexible portions 188A, 190A to help better distribute the stress exerted on the walls of the coronary sinus. Additionally, and/or alternatively, any taper applied to the distal and proximal ends of substantially straight, substantially rigid elongated body 184 may be elongated, e.g., such as shown at 188B, 190B in FIG. 18, so as to better distribute the stress imposed on the walls of the coronary sinus. In one preferred form of the invention, and looking now at FIG. 19, the substantially straight, substantially rigid elongated body 184 may have relatively long relatively flexible portions 188A, 190A with relatively elongated tapers 188B, 190B. If desired, each of the relatively long, relatively flexible portions 188A, 190A with relatively elongated tapers 188B, 190B may be as long as, or longer than, the substantially straight, substantially rigid intermediate portion of elongated body 184.

Figure 19:
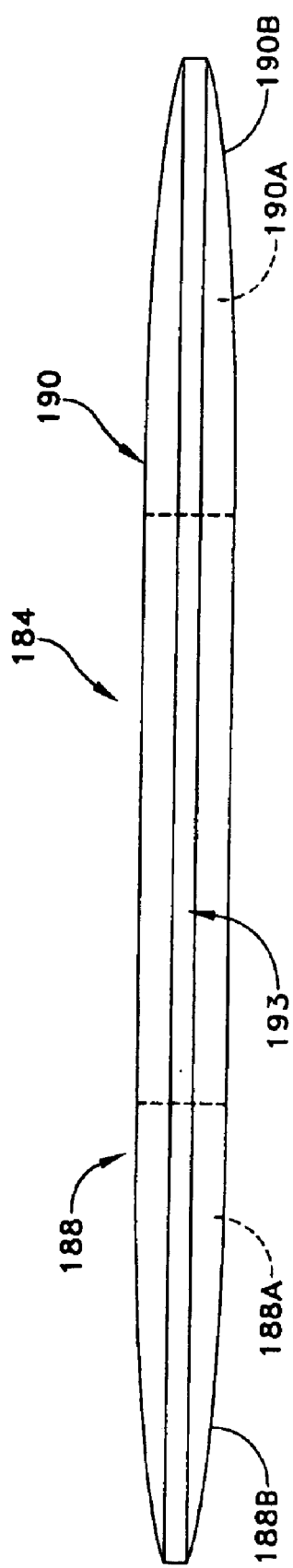

In the preceding discussion, elongated body 157 (or 184) is generally described as being substantially straight and substantially rigid, with or without relatively flexible portions 175 (FIG. 12) (or 188A, 190A, FIG. 17) and/or tapers 178 (FIG. 13) (or 188B, 190B, FIG. 18) and/or elongated relatively flexible tapered portions 175, 178 (FIG. 14) (188A, 188B, 190A, 190B, FIG. 19). However, it should be appreciated that the terms "substantially straight", "substantially rigid", "relatively flexible" and the like are meant to be interpreted in the context of the anatomical tissue involved and should not be interpreted in an absolute sense.

Figure 20:
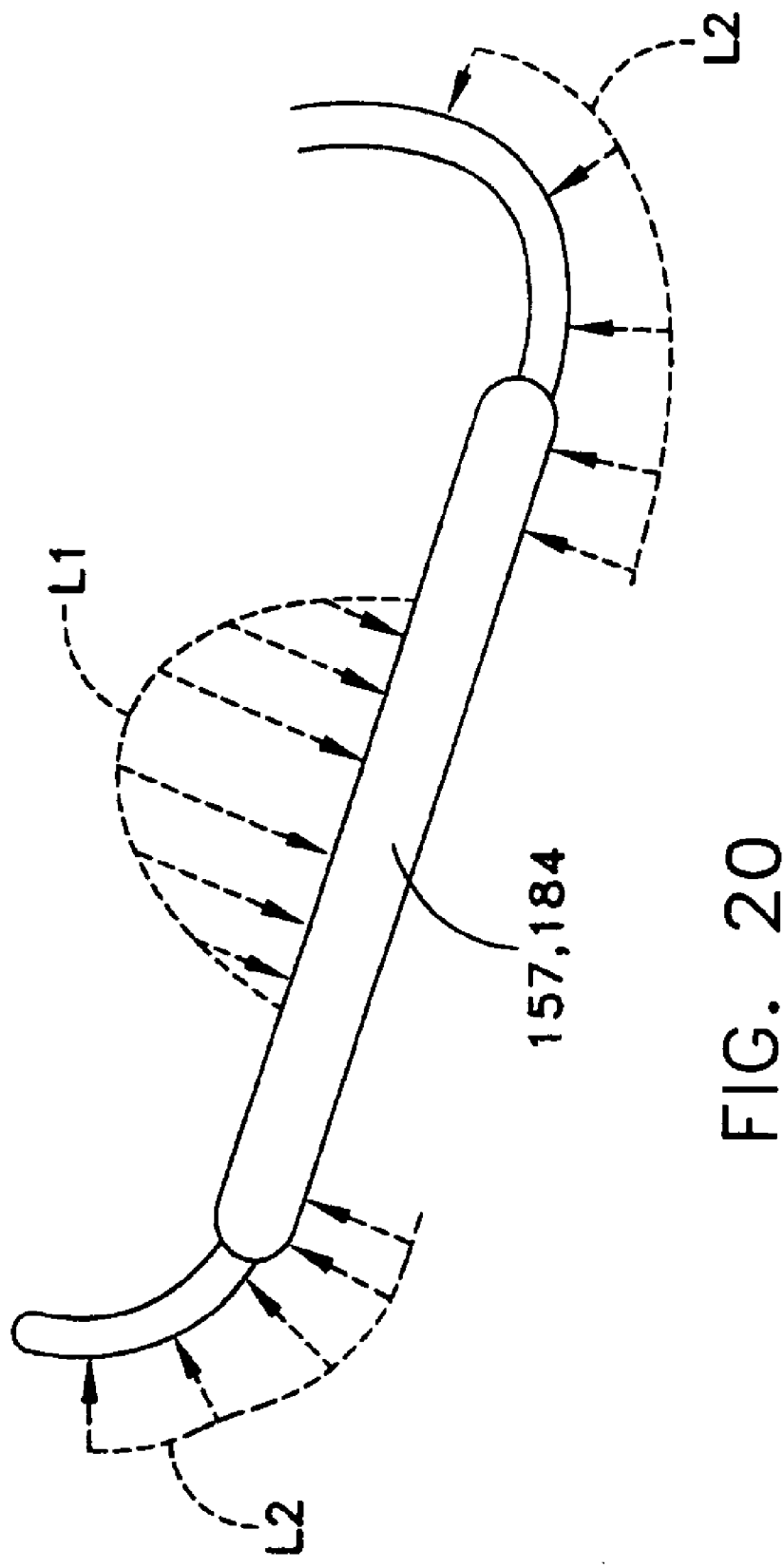
FIG. 20 is a diagrammatic illustration of forces engaging upon an operative portion of the inventive assemblies.

Fundamentally, elongated body 157 (or 184) is constructed so that (1) its intermediate portion imparts an anteriorly-directed force on the walls of the coronary sinus (e.g., as shown by the arrows A in FIG. 7), and (2) its distal and proximal ends impart a posteriorly-directed force on the walls of the coronary sinus (e.g., as shown by the arrows P in FIG. 7). Conversely, a high center load L1 (FIG. 20) is imparted to the intermediate portion of elongated body 157 (or 184) by the mitral annulus, and smaller end loads L2 (FIG. 20) are directed to the distal and proximal ends of elongated body 157 (or 184) by the posterior portions of the coronary sinus.

Among other things, such an effect can be created by using an elongated body 157 (or 184) which is (1) straighter (but not necessarily perfectly straight) than the natural curvature of the portion of the coronary sinus adjacent to the posterior leaflet of the mitral annulus, and (2) more rigid (but not necessarily perfectly rigid) than the anatomical tissue which is to be displaced by the deployed elongated body 157 (or 184).

As noted above, in order to better distribute the loads on the proximal portions of the coronary sinus, the distal and proximal ends of elongated body 157 (or 184) may have relatively flexible portions 175 (FIG. 12) (or 188A, 190A, FIG. 17) and/or tapers 178 (FIG. 13) (or 188B, 190B, FIG. 18) and/or elongated relatively flexible tapered portions 175, 178 (FIG. 14) (188A, 188B, 190A, 190B, FIG. 19). Furthermore, the flexibility of these portions 175 (188A, 190A), 178 (188B, 190B) and/or 175, 178 (188A, 188B, 190A, 190B) can vary along their length; thus, the elongated relatively flexible tapered portions 175, 178 (FIG. 14) (188A, 188B, 190A, 190B, FIG. 19) can become more flexible as they extend toward their outer ends.

Indeed, there is nothing in the present invention which requires that the intermediate portion of elongated body 157 (or 184) be absolutely rigid; in fact, it will function satisfactorily so long as it is substantially resistive to the high center load L1 (FIG. 20) imposed by the mitral annulus. The design is further enhanced by having the distal and proximal ends of elongated body 157 (or 184) be somewhat less resistive to the smaller end loads L2 (FIG. 20) directed by the posterior walls of the coronary sinus. Thus, a satisfactory design may be implemented with a device which has a rigidity gradient along its length, with a highest rigidity at or near the center and lower rigidity at or near its two ends (or, conversely, a flexibility gradient along its length, with a lowest flexibility at or near the center and a higher flexibility at or near its two ends). This may be accomplished by tapering the elongated body; and/or by varying its composition and/or material properties; and/or by other techniques which will be apparent to a person skilled in the art in view of the present disclosure. Or a satisfactory design may be implemented with a device which has some degree of flexibility along its entire length; and this flexibility may vary with length or it may be substantially constant along the entire length of the elongated body 157 (or 184).

Thus, as noted above, a satisfactory design may be implemented with an elongated body 157 (or 184) which is straighter (but not necessarily perfectly straight) than the natural curvature of the portion of the coronary sinus adjacent to the posterior leaflet of the mitral annulus, and (2) more rigid (but not necessarily perfectly rigid) than the anatomical tissue which is to be displaced by the deployed elongated body 157 (or 184).

Figure 21:
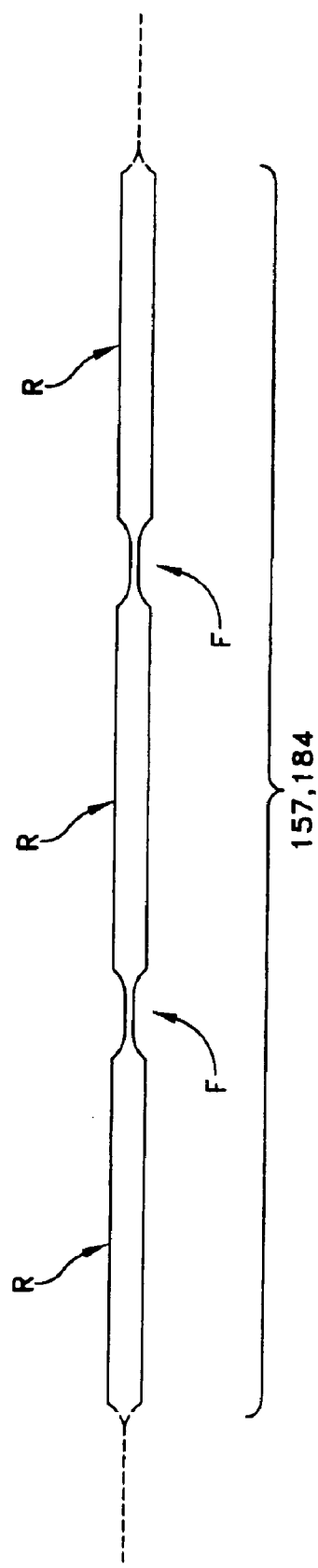
FIG. 21 is a schematic view of another alternative form of the present invention.
Figure 22:
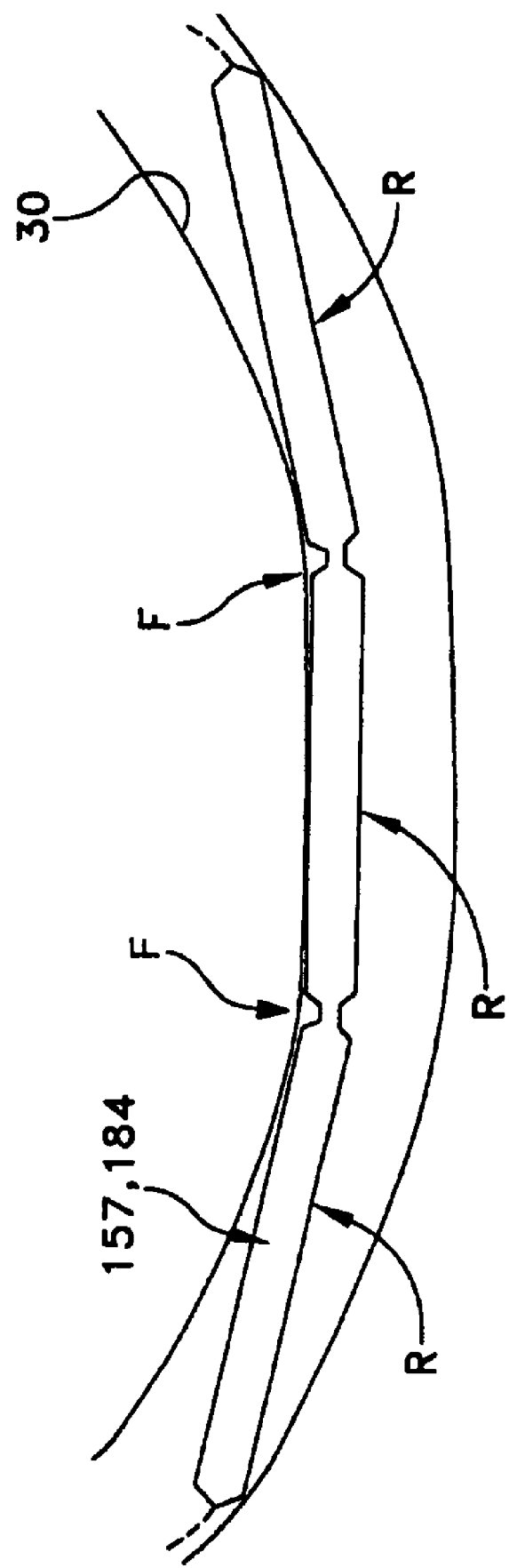
FIG. 22 is a schematic view showing the construction of FIG. 21 deployed in a coronary sinus.

In other alternative embodiments, the elongated body 157, 184 may be formed by two or more substantially straight, substantially rigid segments R connected together by one or more flexible segments F. See, for example, FIGS. 21 and 22, which shows such a construction. By varying the relative lengths of segments R and F, and by varying the relative rigidity of substantially rigid segments R and by varying the relative flexibility of flexible segments F, superior annulus displacement may be effected, whereby to better reduce mitral regurgitation.

Figure 23:
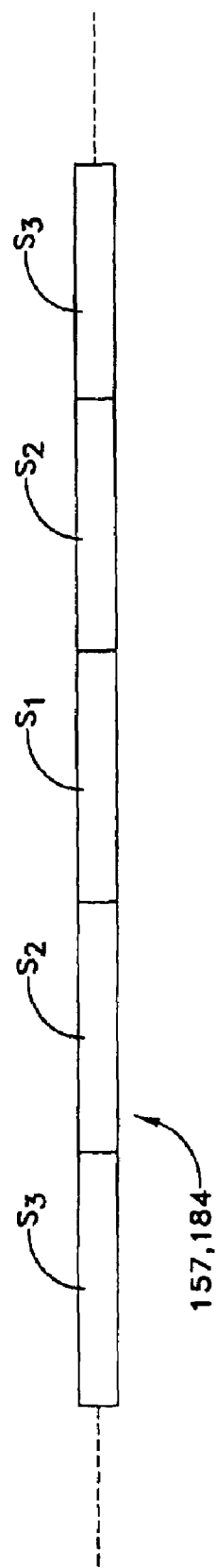
FIG. 23 is a schematic view of another alternative form of the present invention.
Figure 24:
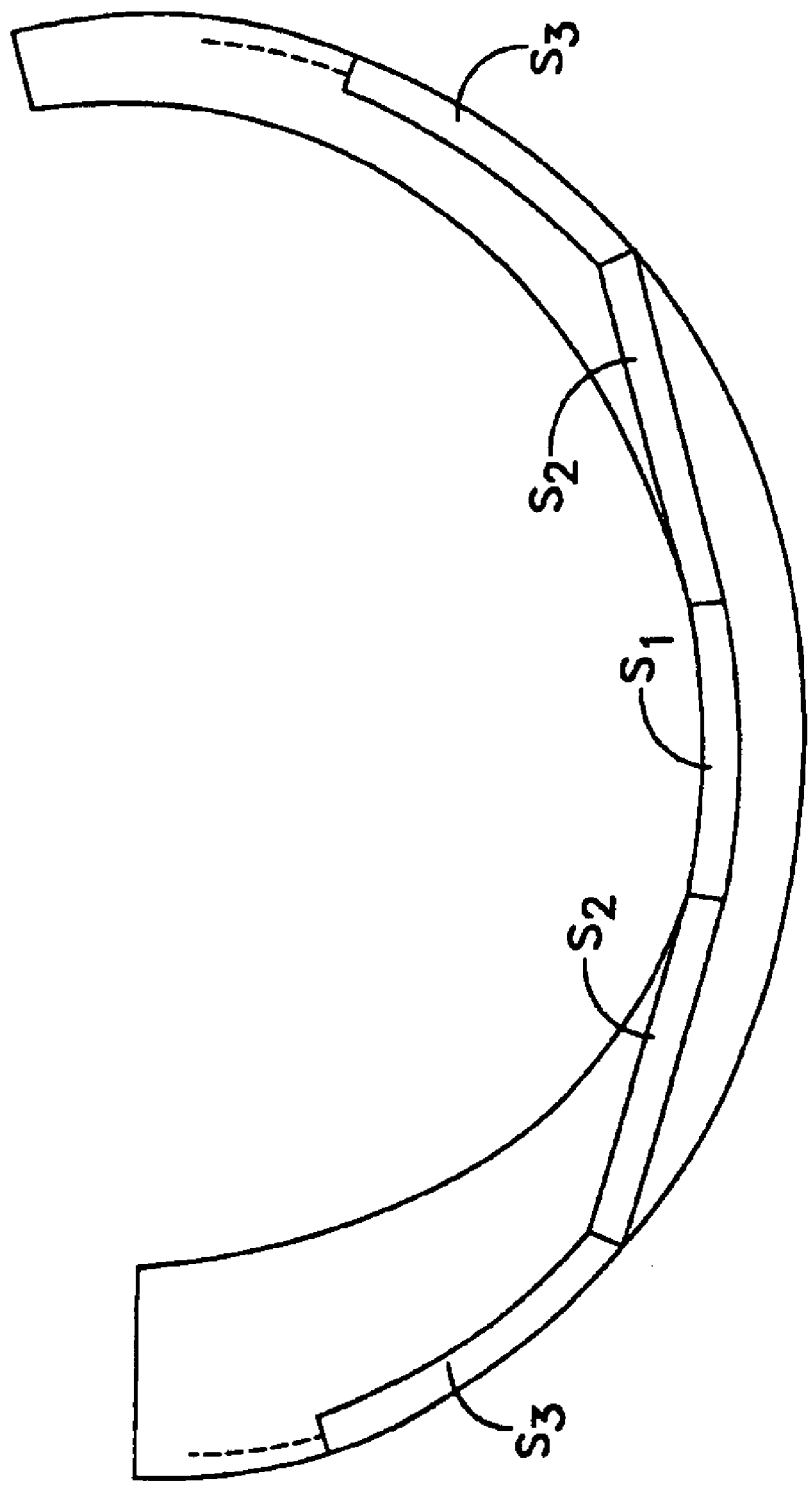
FIG. 24 is a schematic view showing the construction of FIG. 23 deployed in a coronary sinus.

FIGS. 23 and 24 show another preferred construction, where substantially straight, substantially rigid elongated body 157, 184 comprises a plurality of segments $S_1$, $S_2$ and $S_3$, where segment $S_1$ is configured to have a selected degree of flexibility, segments $S_2$ are configured to have a lower degree of flexibility than segment $S_1$, and segments $S_3$ are configured to have a higher degree of flexibility than segment $S_1$. Segments $S_1$, $S_2$ and $S_3$ may be formed integral with one another or they may be connected together by joints. As a result of this construction, segment $S_1$ will carry the load of reconfiguring the mitral annulus, segments $S_2$ will transfer that load far outboard to segments $S_3$, and segments $S_3$ will dissipate that load outboard to the side walls of the coronary sinus. In one preferred form of the invention, segment $S_1$ is constructed so as to have a degree of flexibility which will support the remodeling of the mitral annulus yet permit the segment $S_1$ to roughly conform to the arc of curvature of the mitral annulus at the point of engagement; the segment $S_2$ is constructed so as to have a degree of flexibility sufficiently low so that substantially all of the load generated by the remodeling of the mitral annulus will be transferred to the segments $S_3$; and the segments $S_2$ have a length sufficiently long that posteriorly-directed forces on the walls of the coronary sinus (e.g., as shown by the arrows P in FIG. 7) will be applied substantially proximal and distal of the valve commissures. In this fashion, a purely straightening effect applies outward pressure that tensions the fibrous continuity of the base of the heart, rather than between the commissures, where such forces might tend to induce regurgitation. Among other things, such a construction has been formed to center itself naturally in the region around the posterior leaflet and conforms naturally to the curvature of the posterior leaflet. If desired, such a "5-zone" elongated body can be formed out of a single material, with different diameters being used to create the different body zones.

Thus it will be seen that in various alternative embodiments, the elongated body 157 and/or 184 may be flexible along at least a portion of its length. Regional flexibility and regional stiffness may allow for straightening of select locations of the coronary sinus and corresponding locations of the posterior mitral annulus. This can cause regions of the mitral annulus to move anteriorly, thus causing regional improvements in leaflet coaptation. In addition, the elongated body may be formed by two end segments connected together by a filament: by anchoring the two end segments relative to the anatomy and pulling the filament taught, the naturally curved wall of the coronary sinus can be straightened, whereby to move the posterior mitral annulus anteriorly and thereby reduce mitral regurgitation.

Figure 14:
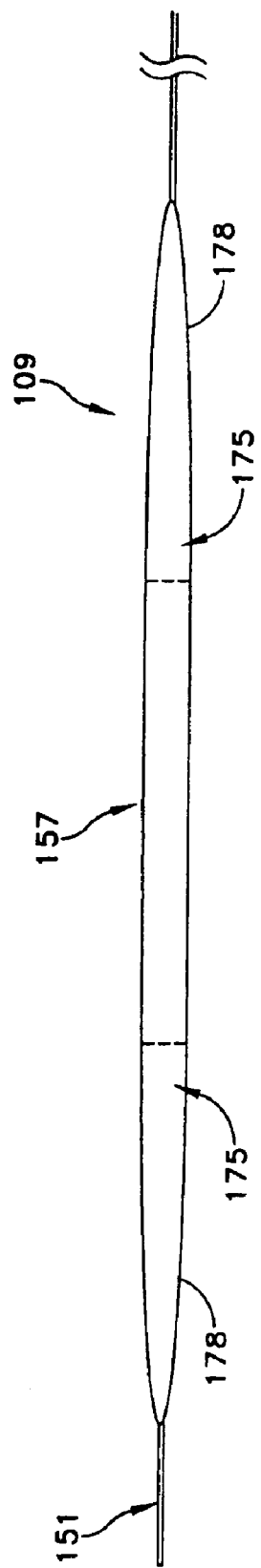
Figure 25:
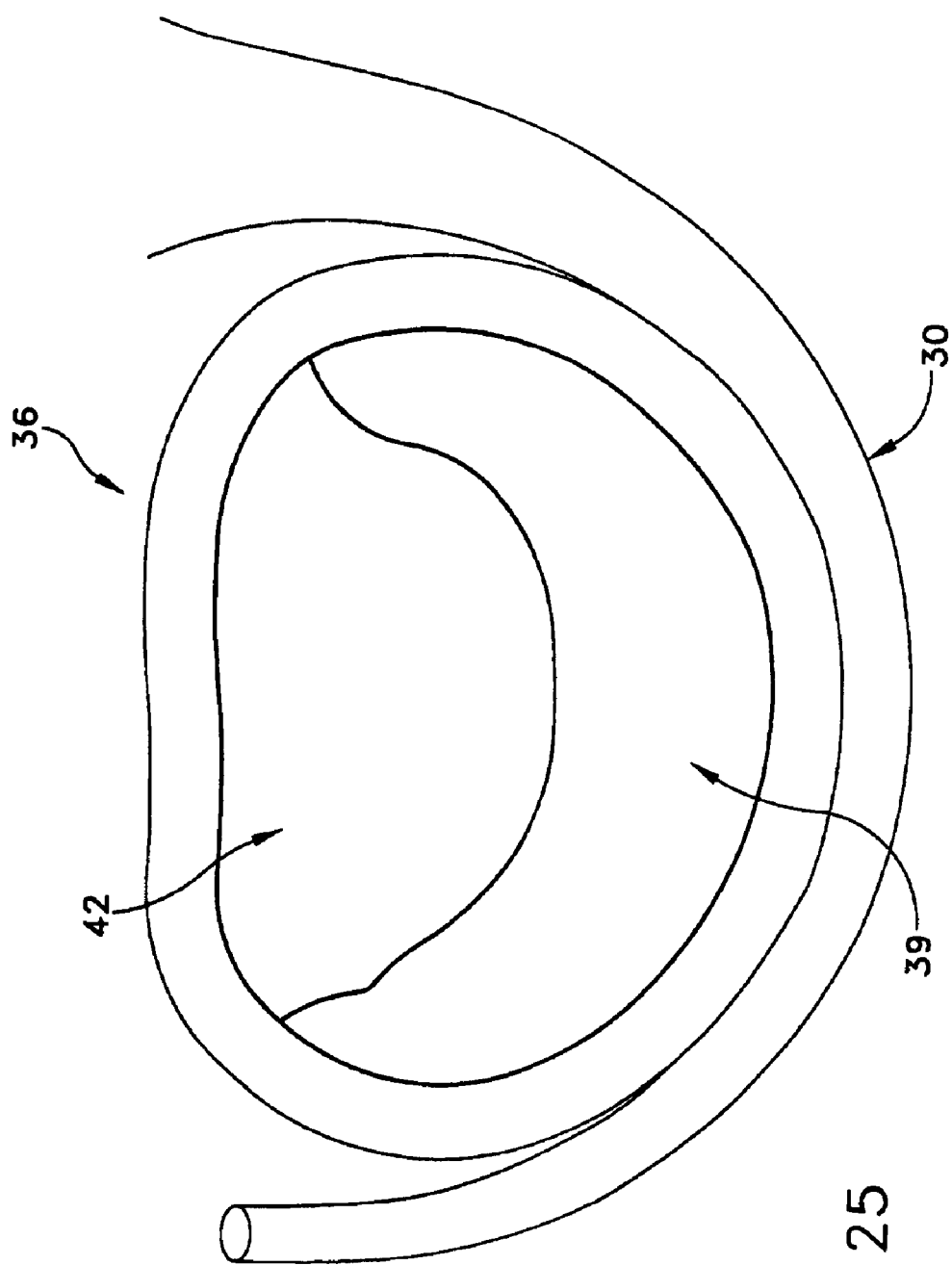
FIG. 25 is a schematic illustration of a normal mitral valve.
Figure 26:
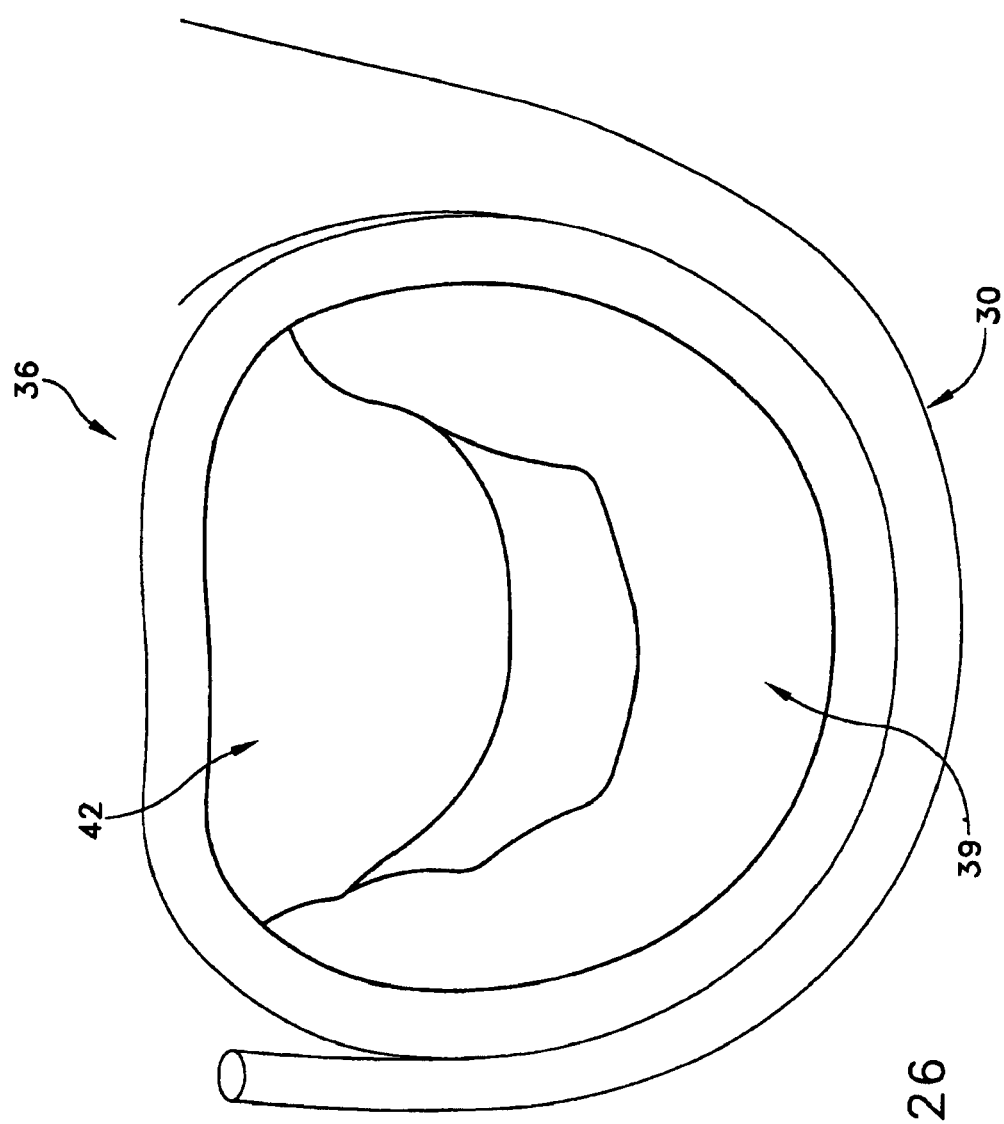
FIG. 26 is a schematic illustration of a regurgitant mitral valve.
Figure 27:
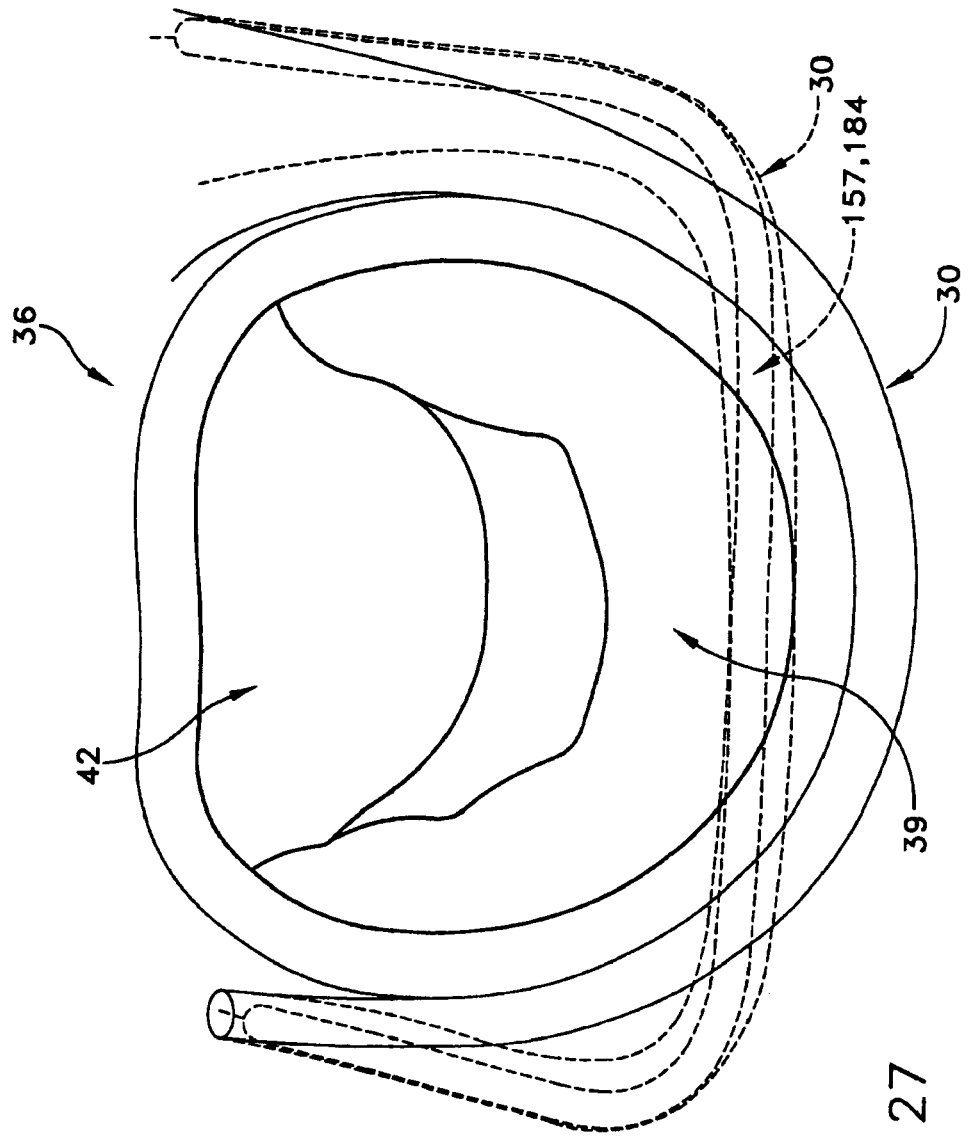
FIGS. 27 and 28 are schematic illustrations showing an elongated body inserted into the coronary sinus, wherein the elongated body comprises a central portion which is substantially straight and substantially rigid.
Figure 28:
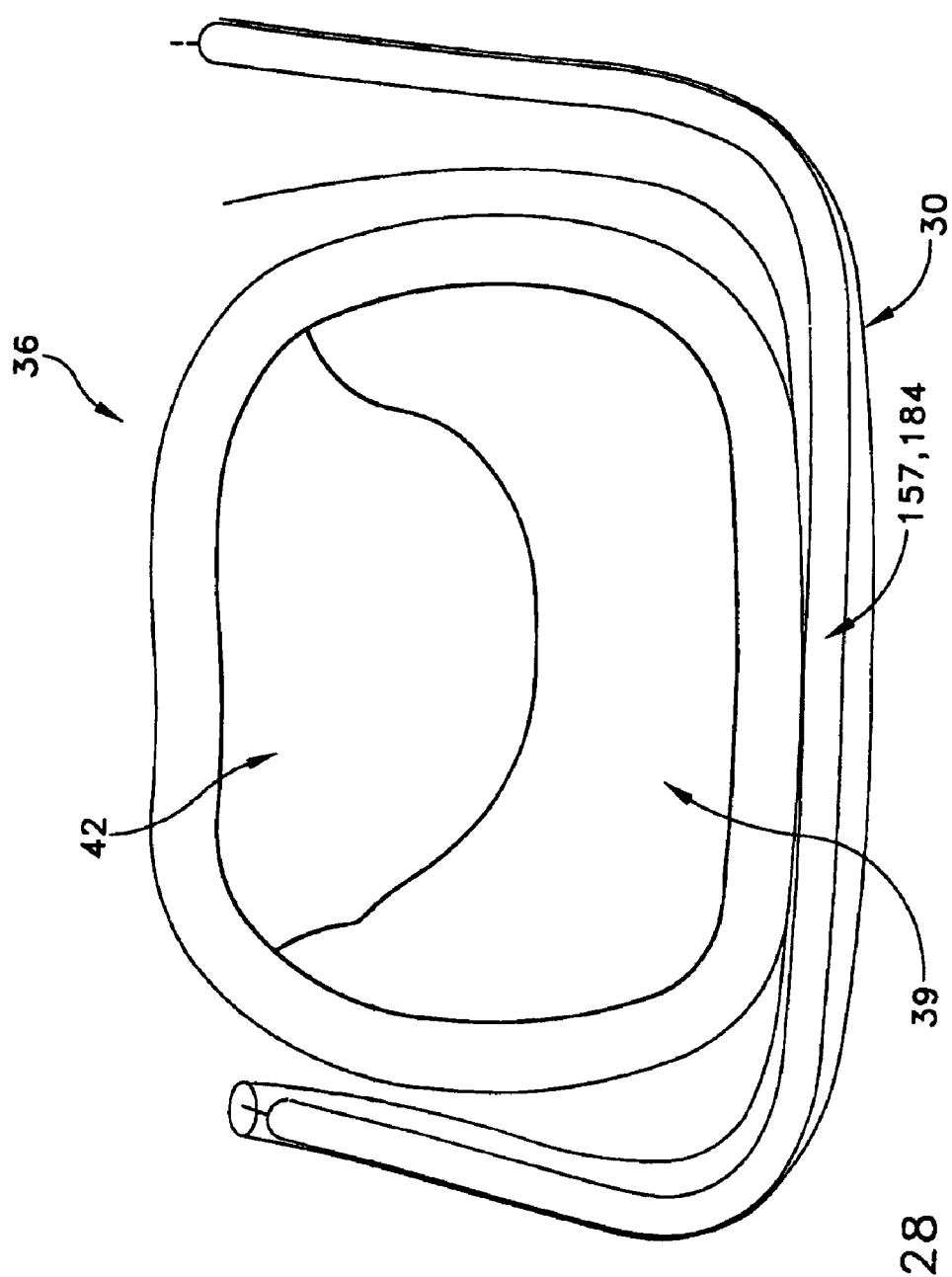
Figure 29:
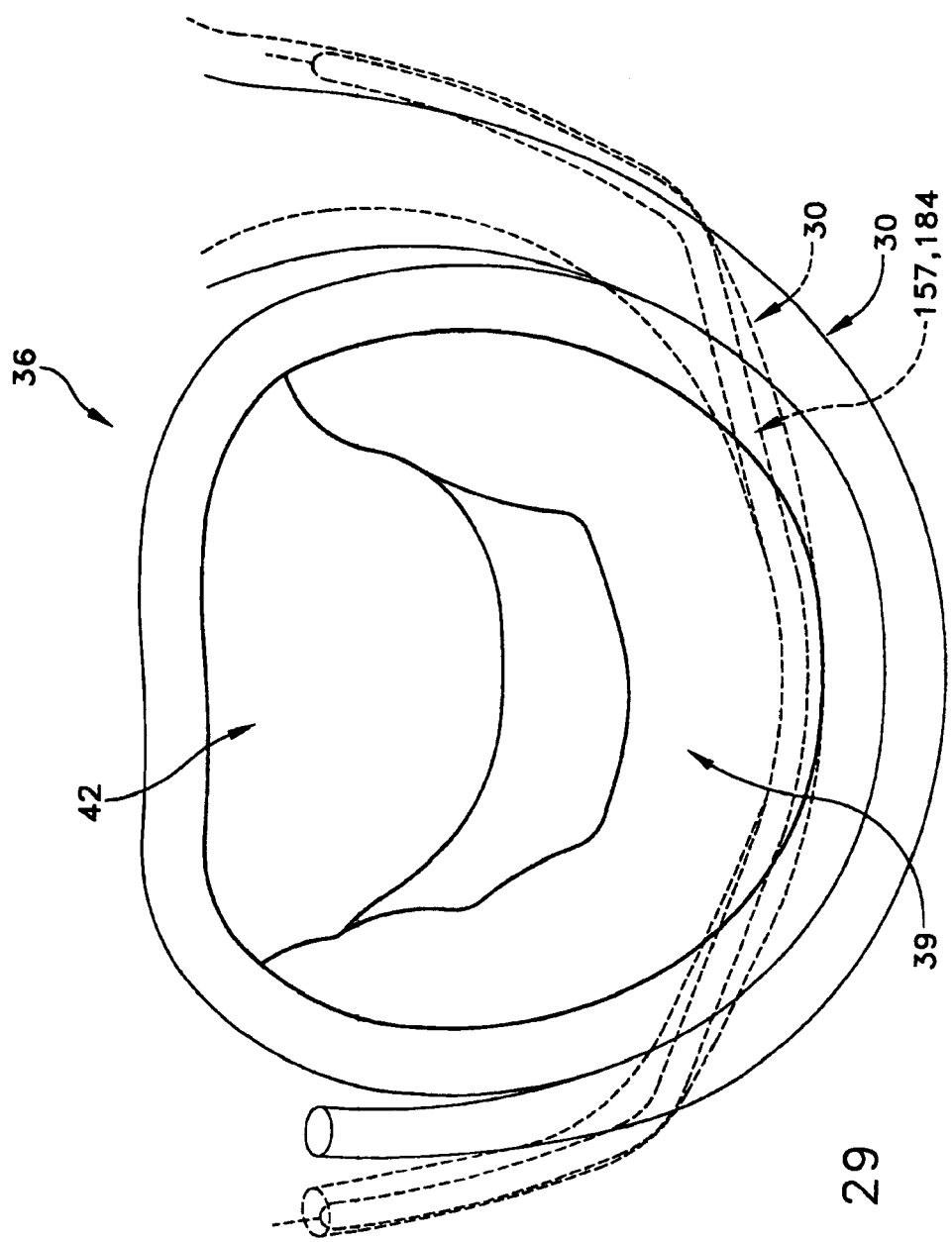
FIGS. 29 and 30 are schematic illustrations showing another elongated body inserted into the coronary sinus, wherein the elongated body comprises elastic central and end portions.
Figure 30:
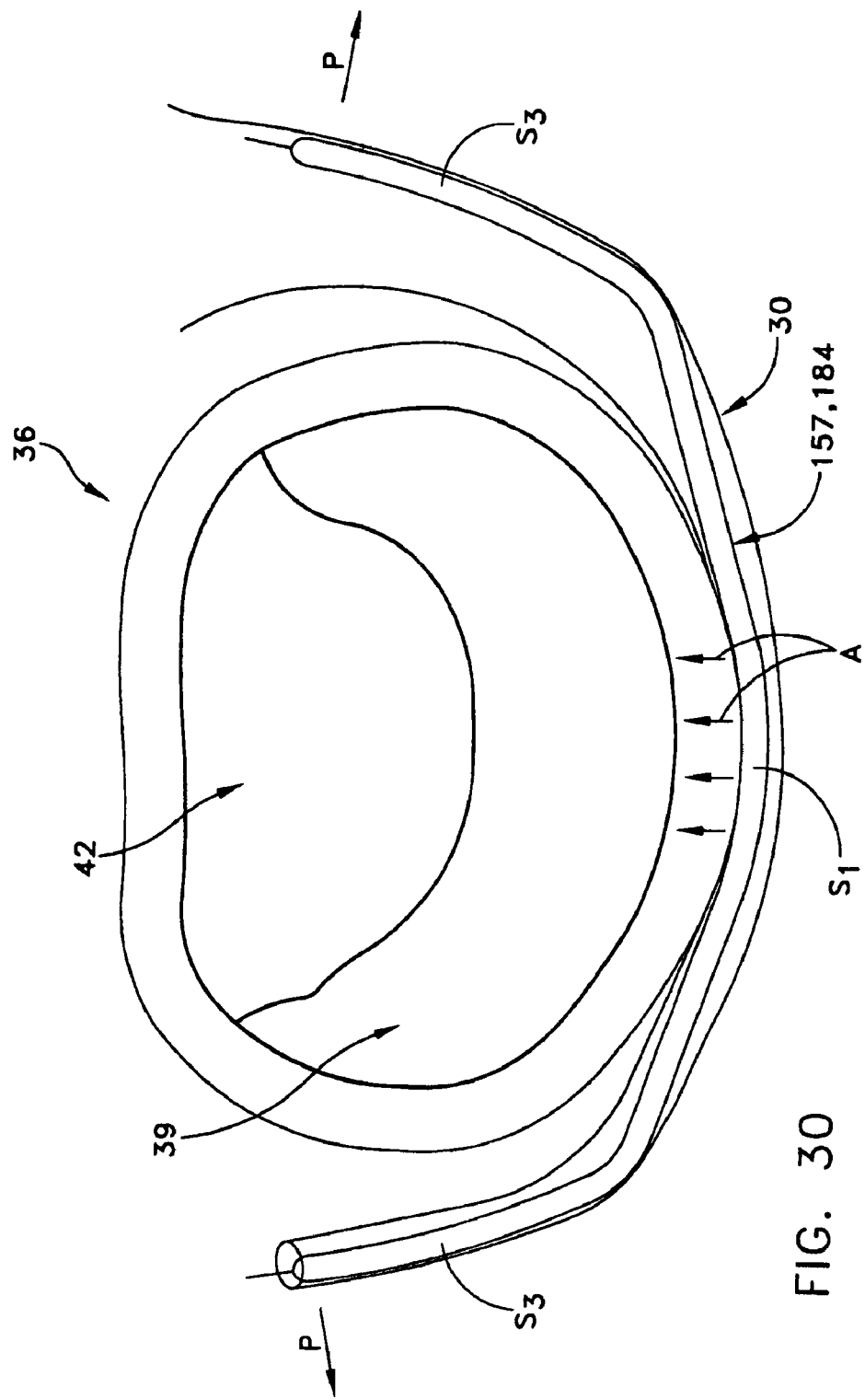
Figure 31:
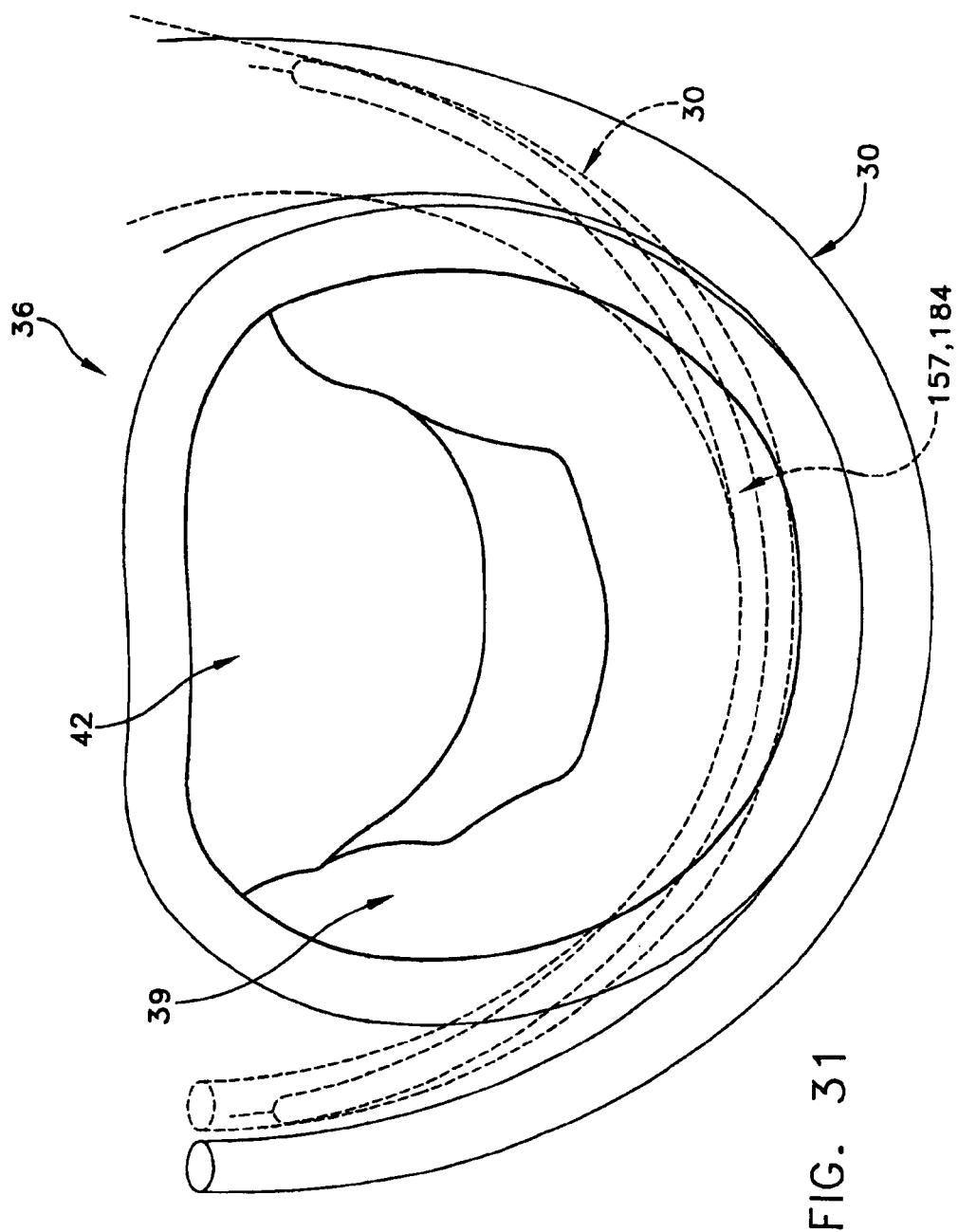
FIGS. 31 and 32 are schematic illustrations showing another elongated body inserted into the coronary sinus, wherein the elongated body has a variable elasticity along its length.
Figure 32:
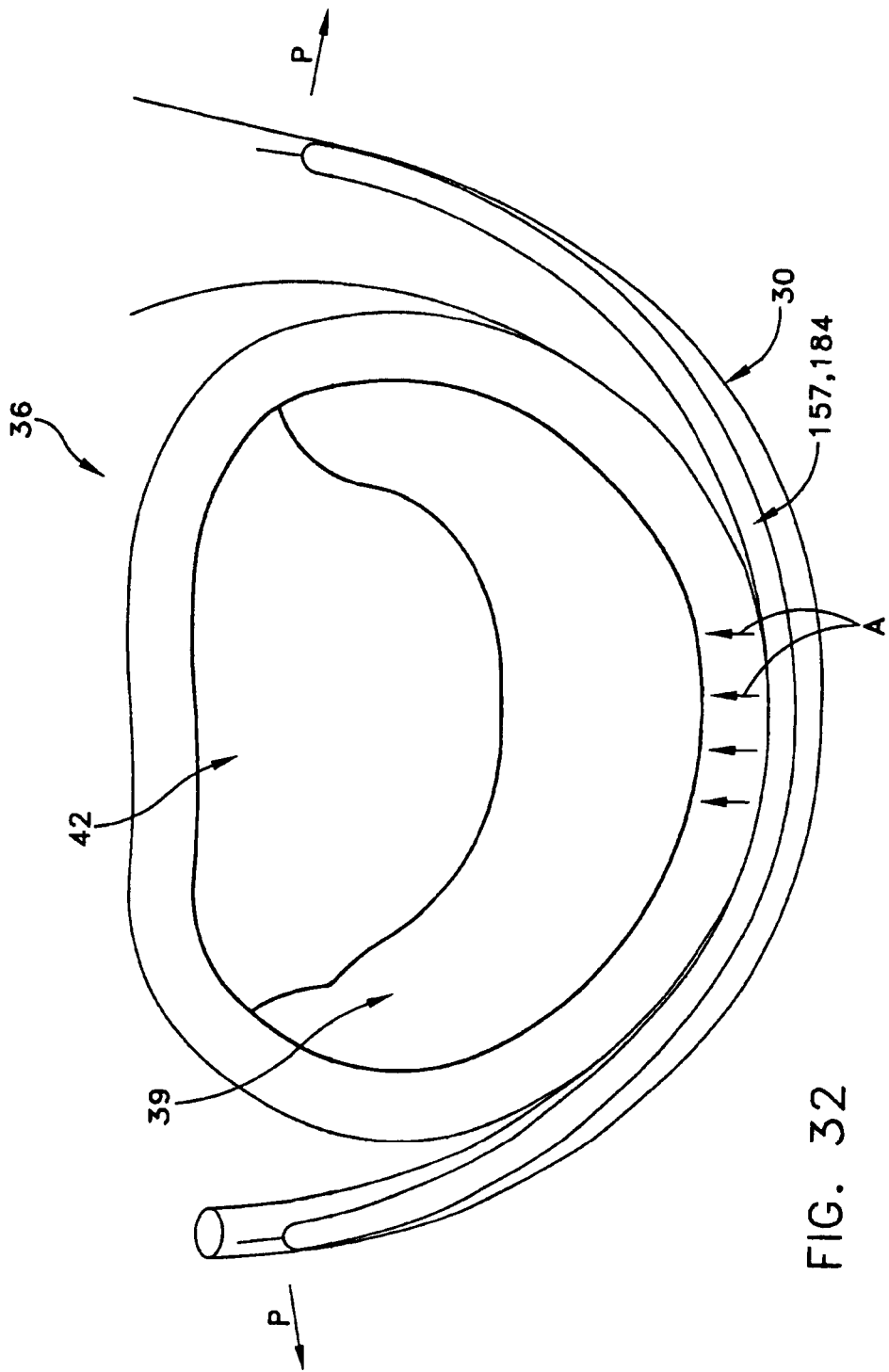

By varying the rigidity of elongated body 157, 184, it is possible to effect a range of anatomical changes to the mitral valve. More particularly, FIG. 25 shows a normal mitral valve 36 where the leaflets 39, 42 adequately coapt, and FIG. 26 shows a regurgitant mitral valve 36 where the leaflet 39, 42 do not adequately coapt.

Where the central portion of elongated body 157, 184 is large and substantially absolutely rigid relative to the anatomy, and the two ends of elongated body 157, 184 terminate in relatively flexible sections (e.g., a construction such as is shown in FIGS. 14 and 19), anatomical displacement can be substantially as that shown in FIGS. 27 and 28.

Where elongated body 157, 184 has a bar with some flexibility at both its center $S_1$ and its two ends $S_3$, and relative inflexibility in the connecting portions $S_2$ (e.g., a construction such as is shown in FIGS. 23 and 24) it can be made to provide a flexible sling for supporting the annulus and making a gentle engagement with the walls of the coronary sinus, such as that shown in FIGS. 29 and 30. In one preferred form of the invention, elongated body 157, 184 has its flexibility tailored along its length so that it closely conforms to the geometry of the natural annulus, whereby to move the posterior annulus (and hence the posterior leaflet) towards the anterior leaflet while supporting the posterior annulus in its natural curvature, such as that shown in FIGS. 31 and 32.

In one preferred construction, the elongated body 157, 184 has its geometry and flexibility tailored so that the posteriorly directed forces on the walls of the coronary sinus (e.g., as shown by the arrows P in FIG. 7) will be applied in locations primarily proximal and distal of the anterior and posterior commissures respectively. See, for example, FIGS. 30 and 32, which show how the illustrated constructions impart their forces on the patient's anatomy, i.e., the intermediate portions imparting the anteriorly-directed force on the walls of the coronary sinus (as shown by the arrows A) and the distal and proximal ends imparting the posteriorly-directed force on the walls of the coronary sinus (as shown by the arrows P). By applying the posteriorly-directed forces P in the area of the valve commissures, side-jetting in the region of the commissures is minimized and superior leaflet coaptation attained.

In addition to the foregoing, it will be appreciated that the amount of force applied to the mitral annulus will be a function of the size and geometry of elongated body 157, 184 and its flexibility. In one preferred form of the invention, it is preferred that the size, geometry and resiliency of the elongated body 157, 184 be such that a relatively high force (e.g., approximately 2–5 pounds of force) will be applied to the central section of the mitral annulus, whereby substantially complete remodeling will typically be achieved immediately upon insertion of the elongated body 157, 184 into the coronary sinus. In another preferred form of the invention, it is preferred that the size, geometry and resiliency of the elongated body 157, 184 be such that a significantly lesser force (e.g., approximately 1–3 pounds of pressure) will be applied to the mitral annulus, whereby only partial remodeling will typically be achieved immediately upon insertion of the elongated body 157, 184 into the coronary sinus; however, by forming elongated body 157, 184 out of a sufficiently resilient or preferably superelastic material such as Nitinol, the elongated body will thereafter continue to apply a remodeling force to the mitral annulus, even in the case where the anatomy begins to move in response to the applied load, thus gradually effecting the complete remodeling desired.

Figure 33:
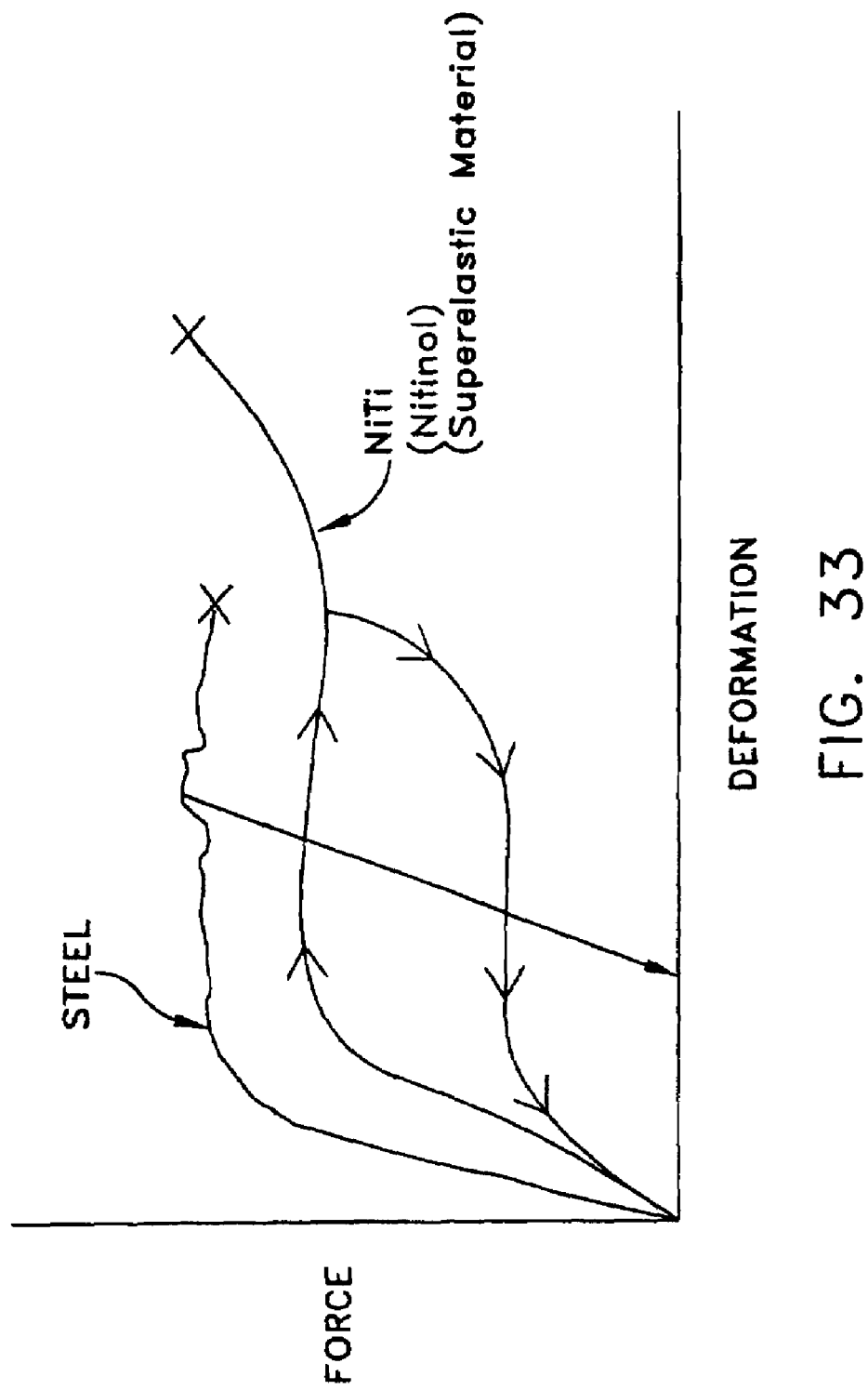
FIG. 33 is a schematic illustration showing the force deformation curve for the two materials Nitinol and stainless steel.

In this latter situation, where elongated body 157, 184 is formed out of a resilient material and the desired valve remodeling is to be gradually effected over time, it is frequently desirable that the force applied by elongated body 157, 184 remain relatively constant over time. To this end, certain materials may be more desirable than other materials. More particularly, and looking next at FIG. 33, there is shown a schematic illustration showing the force deformation curve for two materials, Nitinol and stainless steel. As seen in FIG. 33, as Nitinol is deformed during initial implantation and then relaxed during subsequent tissue remodeling, it applies a relatively constant force to the tissue; however, as stainless steel is deformed and then relaxed, it applies a widely changing force to the tissue. Thus, it is generally desired that elongated body 157, 184 be formed at least in part out of Nitinol or other superelastic material.

In addition to the foregoing, elongated body 157 and/or 184 may have any of a variety of non-straight shapes along its length. For example, the elongated body may be wavy, spiraled, or curved along all or a portion of its length. By way of example, elongated body 157 and/or 184 may have a curved configuration so as to invert the natural curvature of the coronary sinus, i.e., so that it is bowed towards the anterior annulus. Or the elongated body may have a compound shape along its length, e.g., it may have a sort of "w" shape, with the center of the "w" being directed towards the anterior annulus. Any of these or other alternate shapes may effect the anterior displacement of the posterior annulus that results in reduction of the mitral valve regurgitation.

Figure 34:
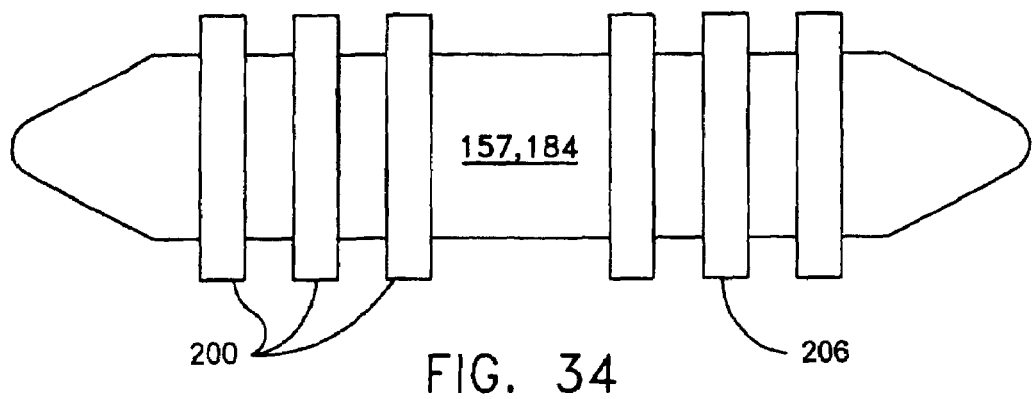
FIGS. 34 and 35 are side elevational views of further alternative embodiments of the elongated body.
Figure 35:
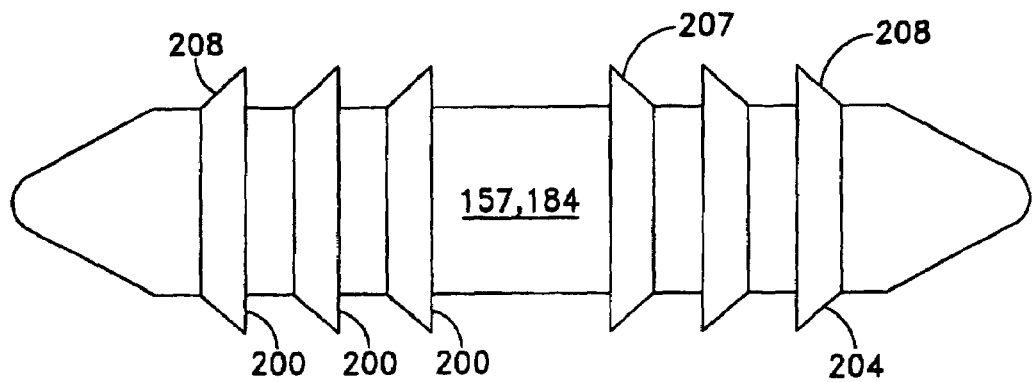
Figure 36:
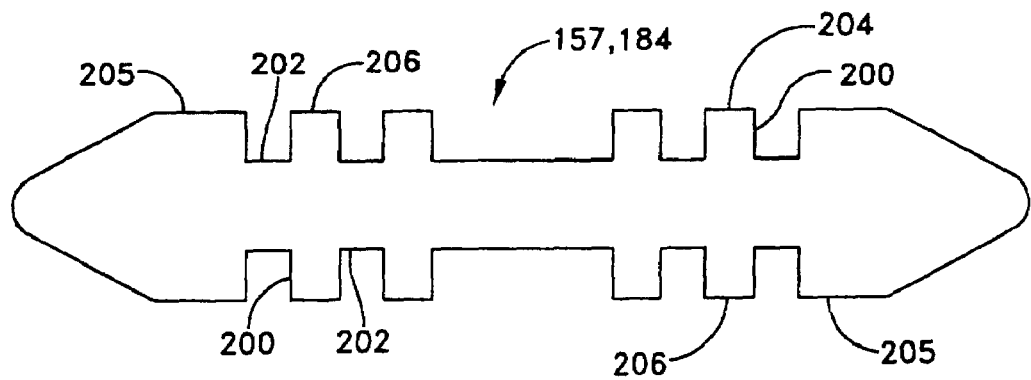
FIG. 36 is a schematic view of a still further alternative embodiment of the elongated body.

Referring next to FIGS. 34–36, it will be seen that the elongated body 157 and/or 184 may be provided with annular ribs 200 extending radially outwardly (FIGS. 34 and 35) from the body 157, 184. The ribs 200 engage the walls of delivery catheter 106 or, where delivery catheter 106 is not used or where delivery catheter 106 has been previously removed, the walls of the coronary sinus 30, so as to mitigate against migration of the body 157, 184 over time. The ribs 200 may also be defined by annular grooves 202 (FIG. 36) in the body 157, 184, in which case circumferential surfaces 204 of the ribs 200 are coincident with the body circumferential surface 205. The ribs 200 may be provided with substantially flat circumferential edges 206 (FIGS. 34 and 36) or with circumferential edges 207 of a generally frustoconical configuration (FIG. 35). In the latter case, it is preferred that the slopes 208 of the edges 207 of some of the ribs 200 be facing a proximal direction, while the slopes 208 of the remaining ribs face a distal direction (FIG. 35). In the case where elongated body 157, 184 includes flexible portions 175 (FIG. 12) (or 188A, 190A, FIG. 17) and/or tapers 178 (FIG. 13) or (188B, 190B, FIG. 18), and or elongated relatively flexible tapered portions 175, 178 (FIG. 14) (or 188A, 188B, 190A, 190B, FIG. 19), ribs 200 may be formed on these structures as well.

Figure 37:
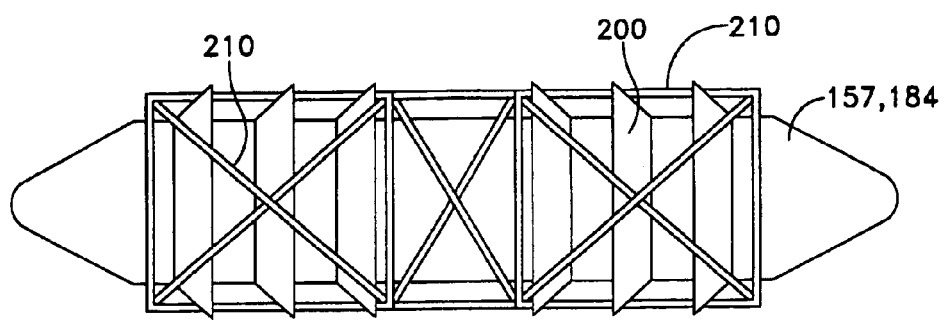
FIG. 37 is a diagrammatic side elevational view showing the elongated body of FIG. 35 in cooperative engagement with a stabilizing scaffold.

In FIG. 37, there is shown an alternative embodiment in which a stabilizing scaffold 210 is used in combination with the elongated body 157, 184 shown in FIG. 34. In this embodiment, the stabilizing scaffold 210 comprises a generally cylindrical spar frame which is placed in the coronary sinus where it engages, and is securely anchored to, the walls of the coronary sinus, and thereafter, the elongated body 157, 184 (with the ribs 200 thereon) is placed in the stabilizing scaffold 210. The ribs 200 of the elongated body 157, 184 engage portions of the stabilizing scaffold 210 such that the elongated body is securely anchored in place in the coronary sinus 30. For example, where stabilizing scaffold 210 comprises openings between the spars of its frame, ribs 200 can interact with the spars and openings to help lock the elongated body 157, 184 to stabilizing scaffold 210.

More particularly, with this form of the invention, stabilizing scaffold 210 is securely anchored to the walls of the coronary sinus (e.g., by outward expansion, and/or by tissue penetration into scaffold openings, and/or by barbs carried by the scaffold, etc.), and the elongated body 157, 184 (with the ribs 200 thereon) is securely anchored to stabilizing scaffold 210 (e.g., by rib-to-scaffold engagement), whereby to (1) help secure the elongated body 157, 184 against longitudinal migration, whereby to provide maintainable reductions in mitral regurgitation, and/or (2) help support the coronary sinus 30 at the point where the greatest load L1 (FIG. 20) is imposed on the coronary sinus, and/or (3) help distribute the concentrated end loads L2 (FIG. 20) of the elongated body 157, 184 to a larger region of the coronary sinus, whereby to minimize trauma to the host blood vessel, and/or (4) help limit conformational changes to the cross-section of the blood vessel in response to the loads applied to the inside of the blood vessel, whereby to ensure reliable blood flow and minimize vascular trauma. In this respect it should be appreciated that the coronary sinus generally has differing characteristics (e.g., diameter, wall firmness, etc.) along its length, and the stabilizing scaffold 210 can be correspondingly engineered to exhibit differing characteristics along its own length. By way of example but not limitation, stabilizing scaffold 210 can have a smaller diameter at its distal end and a larger diameter at its proximal end, in order to correspond to the typical geometry of the coronary sinus. By way of further example but not limitation, stabilizing scaffold 210 might be engineered to provide greater support at the proximal end of the coronary sinus (where the vein is frequently relatively soft) and lesser support at the distal end of the coronary sinus (where the vein is frequently relatively firm).

In one form of the invention, where elongated body 157 is to be placed inside the stabilizing scaffold 210 in the coronary sinus 30, the guidewire 103 in first advanced into the coronary sinus, as described hereinabove. A scaffold-deploying catheter 212 having the stabilizing scaffold 210 therein (FIG. 38) is advanced along the guidewire 103 into the coronary sinus. When the stabilizing scaffold 210 is in the desired location in the coronary sinus, a bumper 214, riding on the guidewire 103, is engaged with the stabilizing scaffold, and the scaffold-deploying catheter 212 is pulled back sufficiently to deploy the stabilizing scaffold 210, and then is withdrawn, along with the bumper 214, leaving the stabilizing scaffold 210 and the guidewire 103 in place within coronary sinus 30. The delivery catheter 106 is then passed along the guidewire 103 until the distal end of the delivery catheter is positioned in the coronary sinus and within the stabilizing scaffold. Once the delivery catheter 106 has been positioned within the coronary sinus and within the stabilizing scaffold, the guidewire 103 is removed. The push rod 109 is then passed through the central lumen 136 of the delivery catheter 106 until the elongated body 157 is located adjacent to the posterior annulus of the mitral valve 36 and within stabilizing scaffold 210. The delivery catheter 106 is then withdrawn, whereupon the body ribs 200 engage the stabilizing scaffold, as described above, leaving the push rod 109 in place, with the elongated body 157 locked in the stabilizing scaffold 210.

In another form of the present invention, where elongated body 184 is to be placed inside the stabilizing scaffold 210 in the coronary sinus, the guidewire 103 is advanced into the coronary sinus, as described hereinabove. The scaffold-deploying catheter 212, with the stabilizing scaffold 210 therein, is mounted on the guidewire 103 and is advanced into the coronary sinus 30. Then, with the bumper 214 holding the stabilizing scaffold 210 in place, the scaffold-deploying catheter 212 is pulled back sufficiently to deploy the stabilizing scaffold 210, and then is withdrawn, along with the bumper 214, leaving the guidewire 103 and the stabilizing scaffold 210 in place. The body 184 and the push cannula 187 are then advanced over the guidewire 103 until the elongated body 184 is disposed in the stabilizing scaffold 210. The push cannula 187 and guidewire 103 are then withdrawn, leaving the elongated body 184 and stabilizing scaffold 210 in place, with the elongated body 184 locked in the stabilizing scaffold.

Figure 39:
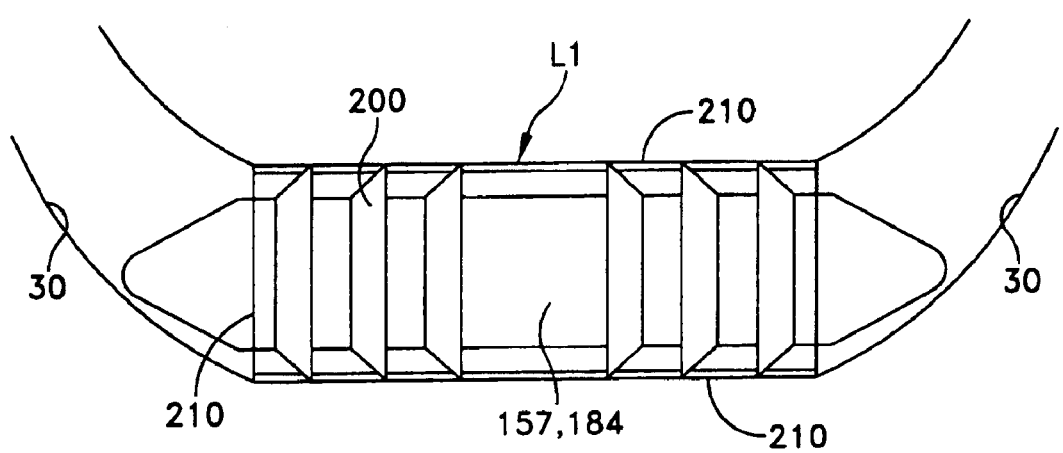
FIG. 39 is a diagrammatic illustration of the elongated body and stabilizing scaffold of FIG. 37 shown in place in a coronary sinus.

Referring to FIG. 39, it will be seen that the greatest load (L1) on the elongated body 157, 184 and the stabilizing scaffold 210 is at the mid-portion thereof, mitigating against migration of the stabilizing scaffold, and therefore the body 157, 184, either distally or proximally.

Figure 40:
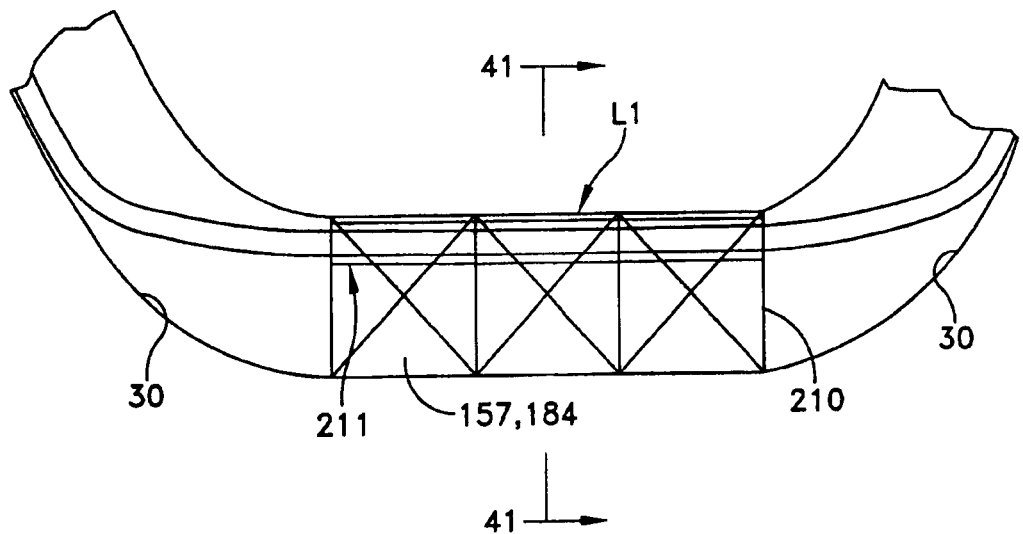
FIG. 40 is a schematic view of another form of the present invention.
Figure 41:
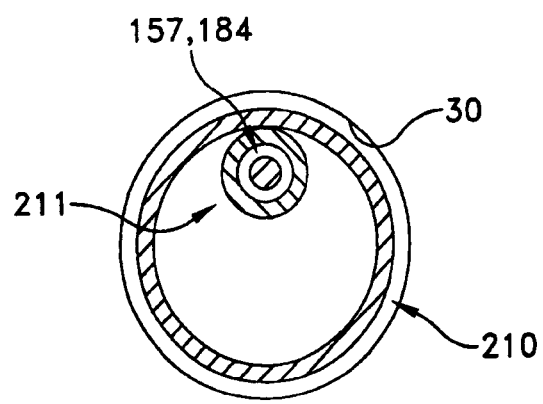
FIG. 41 is a sectional view taken along line 41—41 of FIG. 40.
Figure 42:
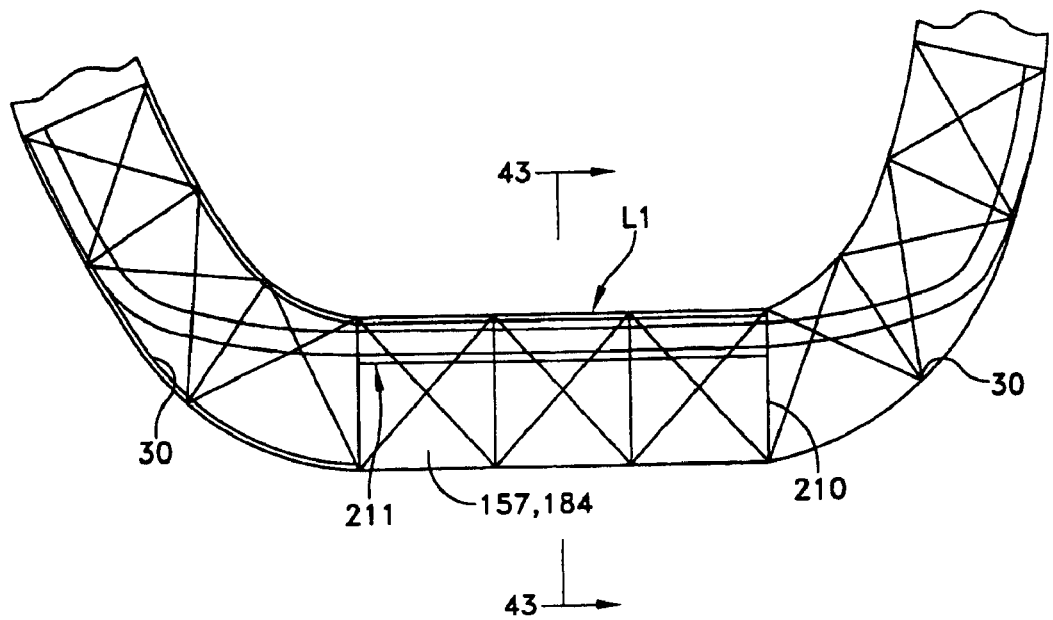
FIG. 42 is a schematic view of another form of the present invention.
Figure 43:
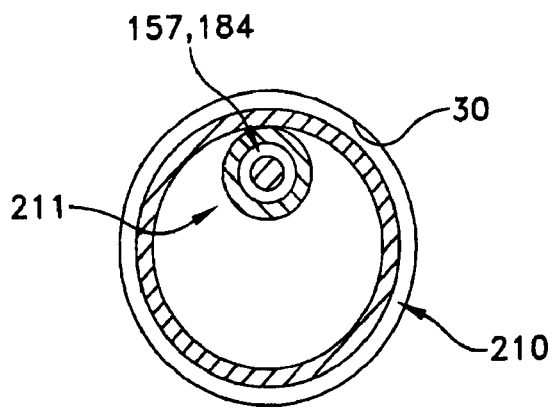
FIG. 43 is a sectional view taken along line 43—43 of FIG. 42.
Figure 44:
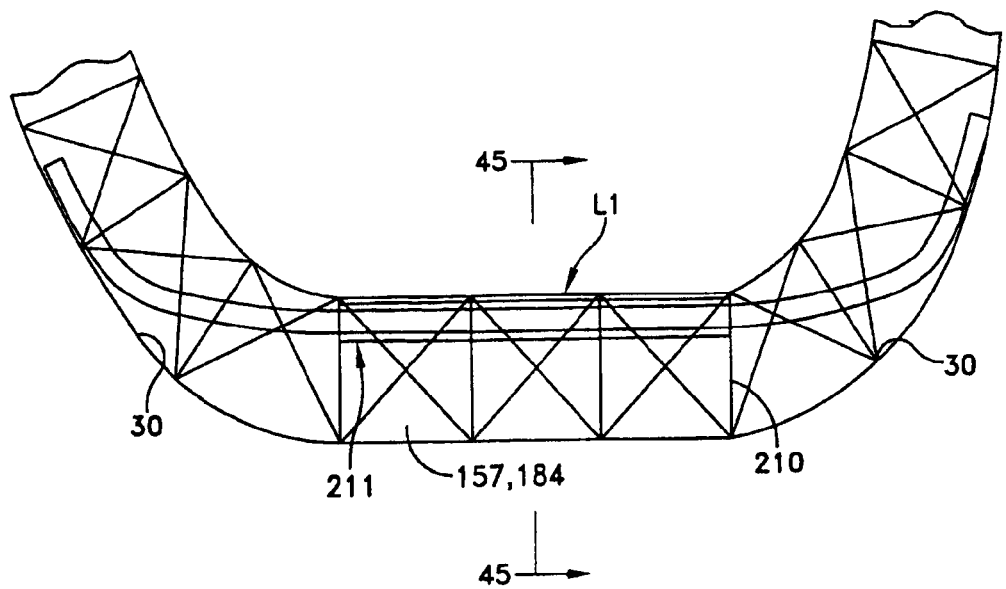
FIG. 44 is a schematic view of another form of the present invention.
Figure 45:
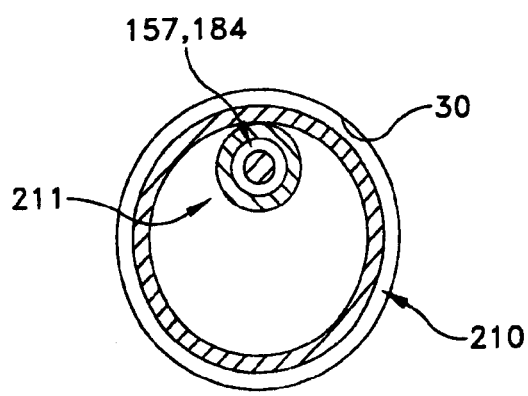
FIG. 45 is a sectional view taken along line 44—44 of FIG. 44.

Looking next at FIGS. 40 and 41, it will also be seen that the elongated body 157, 184 can have a diameter substantially less than the diameter of stabilizing scaffold 210. In this case, stabilizing scaffold 210 can be provided with a guide 211 for receiving the elongated body 157, 184. By way of example, guide 211 may comprise a hollow tube formed on the inside wall of stabilizing scaffold 210, with guide 211 being sized to receive the elongated body 157, 184 and secure it relative to stabilizing scaffold 210. If desired, stabilizing scaffold 210 may terminate short of the ends of elongated body 157, 184, e.g., such as is shown in FIGS. 40, 41. Alternatively, stabilizing scaffold 210 may co-terminate with the ends of elongated body 157, 184, e.g., in the manner shown in FIGS. 42 and 43, or stabilizing scaffold 210 may extend beyond the ends of elongated body 157, 184, e.g., in the manner shown in FIGS. 44 and 45.

Figure 38:
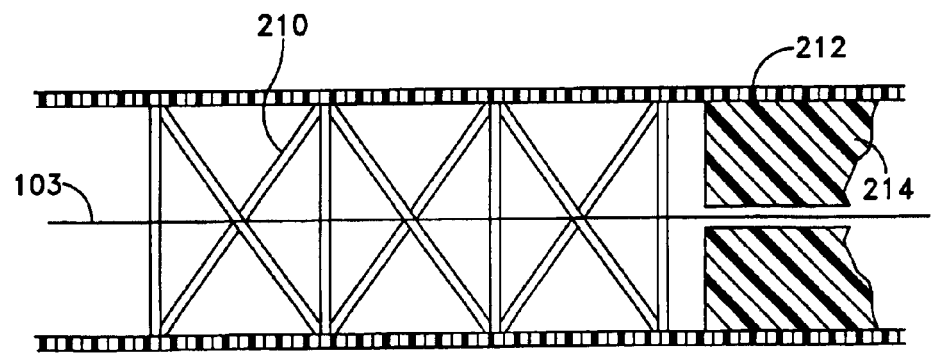
FIG. 38 is a diagrammatic sectional illustration of a step in the deployment of the stabilizing scaffold of FIG. 37.
Figure 46:
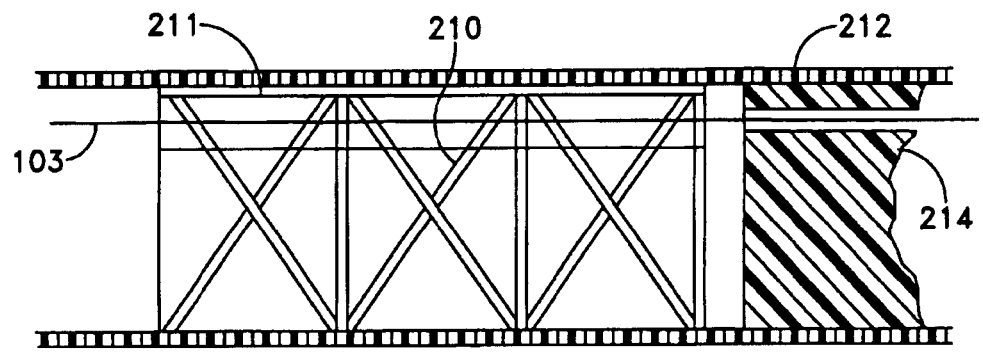
FIG. 46 is a schematic view showing the construction of FIGS. 40–45 being deployed in a coronary sinus.

In one preferred method for using the stabilizing scaffold 210 and the elongated body 157, 184 of FIGS. 40, 41, or FIGS. 42, 43, or FIGS. 44, 45, the stabilizing scaffold 210 may first be deployed using a scaffold-deploying catheter 212 and bumper 214 similar to that shown in FIG. 38, except modified so that guidewire 103 is off-center so as to extend through the stabilizing scaffold's guide 211, e.g., in the manner shown in FIG. 46. The stabilizing scaffold 210 is first deployed in the manner described above, and the guidewire 103 is used to load elongated body 157, 184 into position within the coronary sinus, including through the stabilizing scaffold's guide 211.

Figure 47:
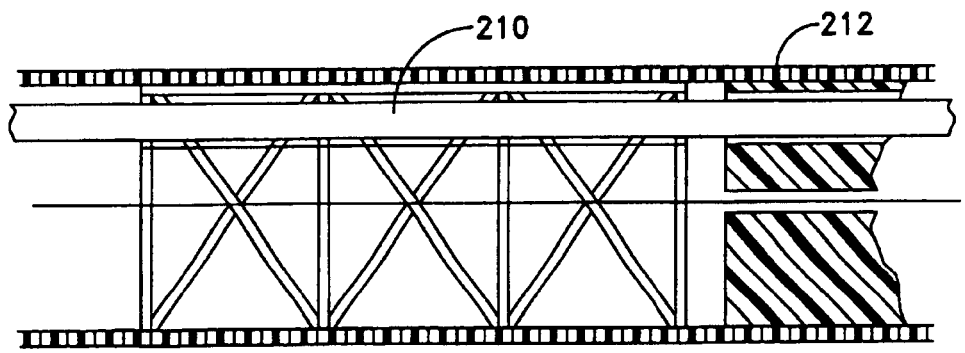
FIG. 47 is a schematic view of another form of the present invention.

In another construction, and looking now at FIG. 47, elongated body 157, 184 may be pre-loaded into the stabilizing scaffold's guide 211 when the stabilizing scaffold is loaded into scaffold-deploying catheter 212; with this construction, the stabilizing scaffold 210 and the elongated body 157, 184 are simultaneously deployed in the coronary sinus.

Figure 48:
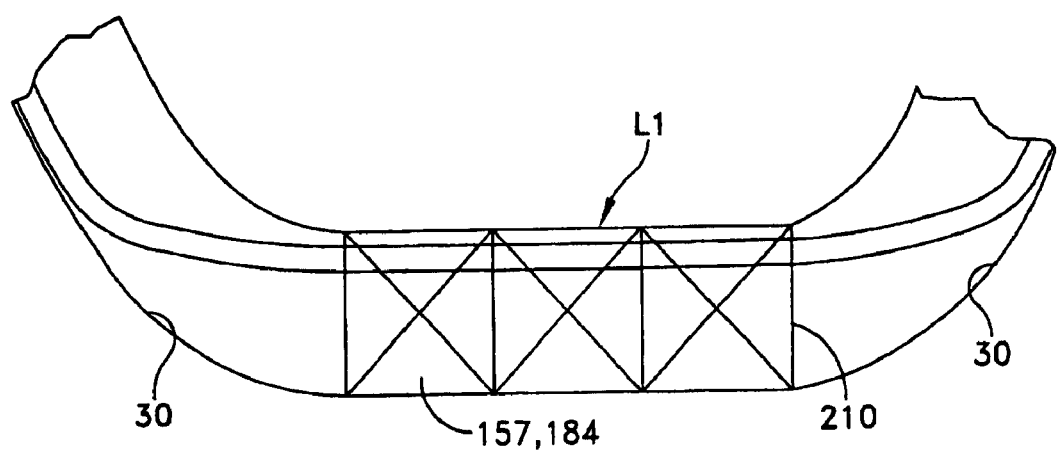
FIGS. 48–51 show alternative constructions for combining elongated bodies and stabilizing scaffolds.
Figure 49:
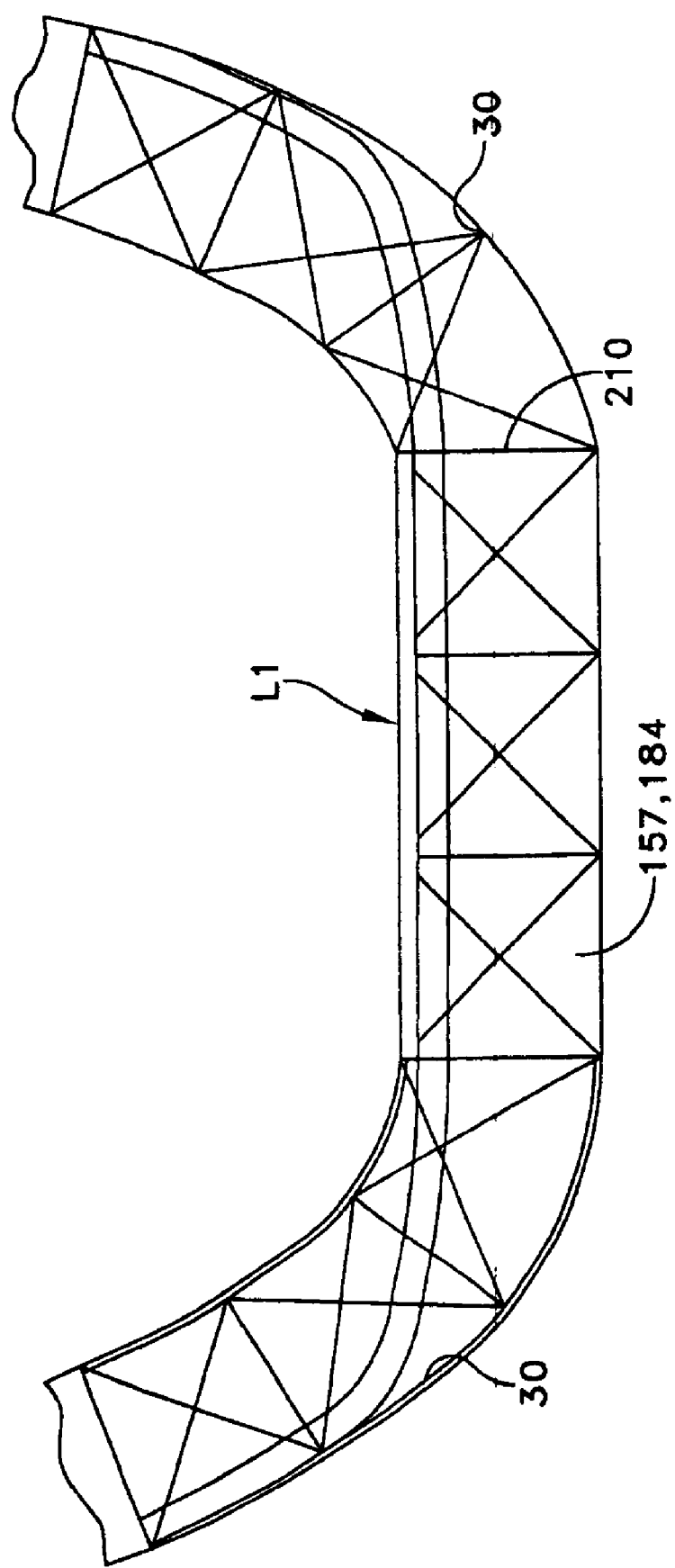
Figure 50:
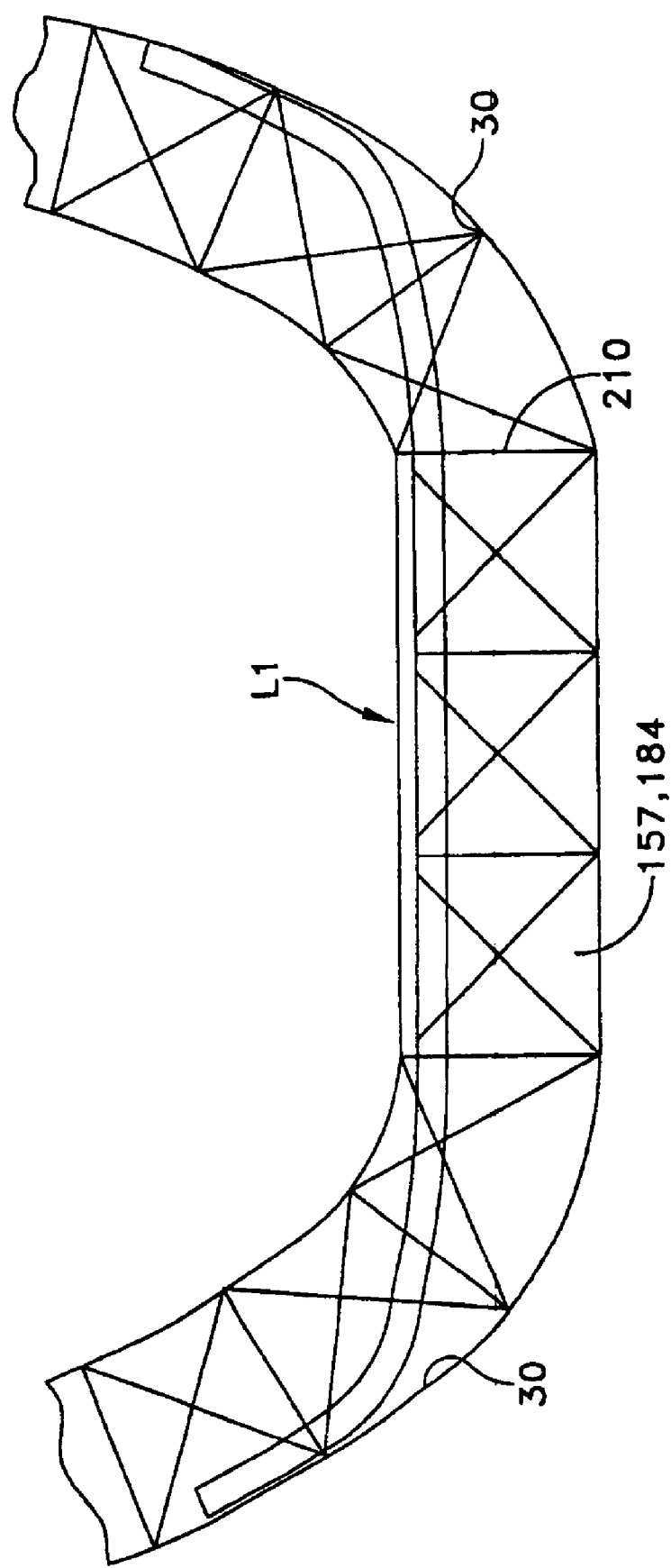

As shown in FIG. 48, the body 157, 184 may be formed as a portion of the stabilizing scaffold 210, with the stabilizing scaffold portion of the combination being located at the mid-portion of the body 157, 184, where the coronary sinus imposes the greatest load L1, which is the load of the therapeutically-displaced coronary sinus. Again, stabilizing scaffold 210 may terminate short of the ends of elongated body 157, 184 (FIG. 48), or stabilizing scaffold 210 may co-terminate with the ends of elongated body 157, 184 (FIG. 49), or stabilizing scaffold 210 may extend beyond the ends of elongated body 157, 184 (FIG. 50).

Figure 51:
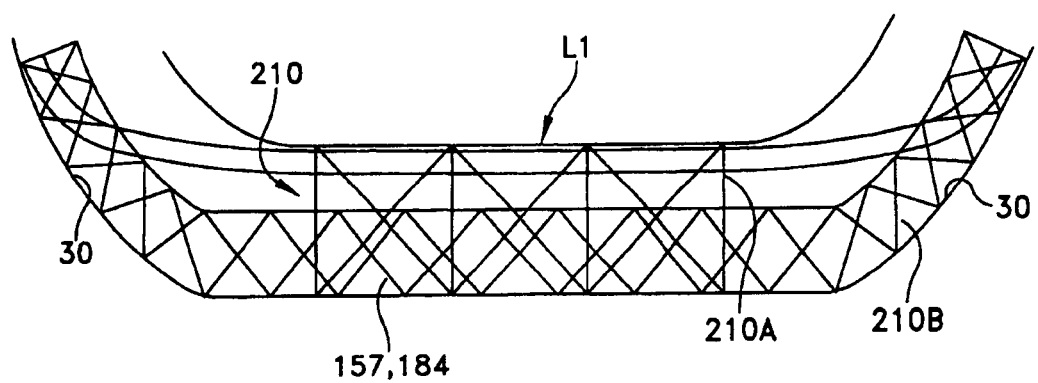
Figure 52:
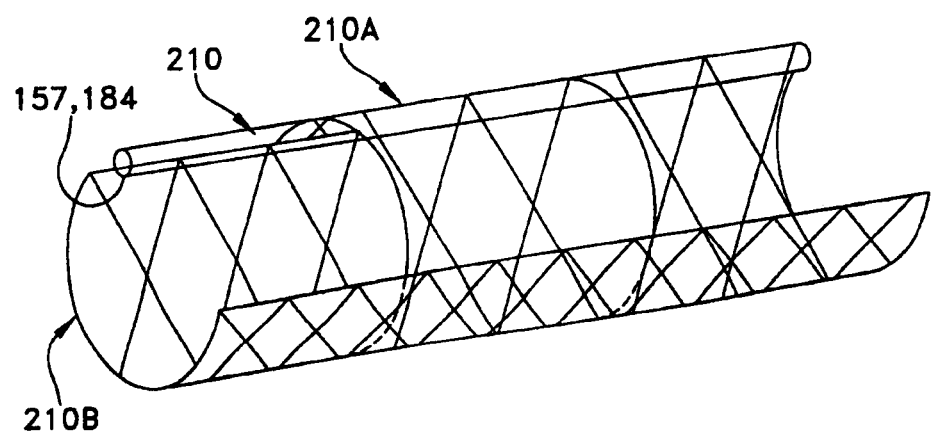
FIG. 52 is a diagrammatic perspective view of the combination of elongated body and stabilizing scaffold of FIG. 51.

In another embodiment shown in FIGS. 51 and 52, the combination of elongated body 157, 184 and stabilizing scaffold 210 includes two or more scaffold portions, such as portions 210A and 210B, portion 210A disposed in a mid-portion of the combination, and portion 210B extending through the portion 210A and extending end-wise therefrom, defining end portions having greater resiliency. The body 157, 184 is fixed to the generally cylindrically-shaped scaffold portion 210A located in the mid-portion of the body 157, 184, and to the half-cylindrical scaffold end portions 210B. The mid-portion 210A, which is the strongest portion of the combination of elongated body and stabilizing scaffold, is the portion resisting the greatest load L1.

Figure 53:
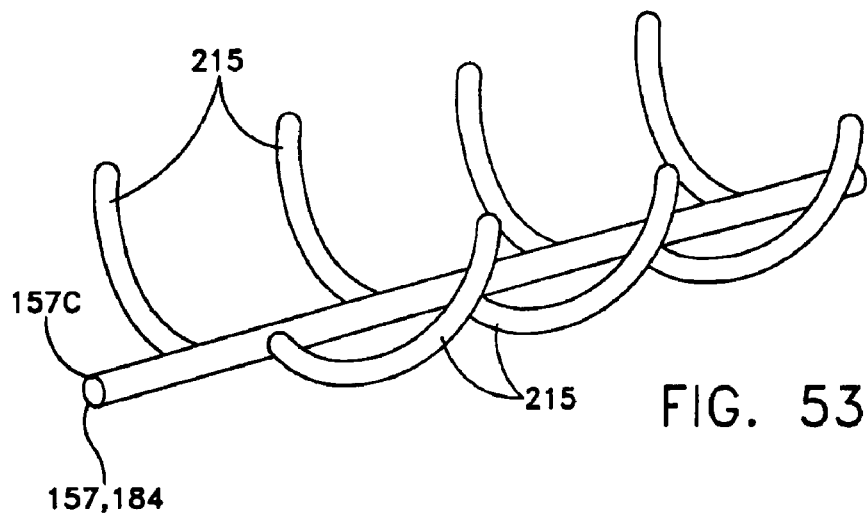
FIG. 53 is a perspective view of an elongated body having ribs extending therefrom.
Figure 54:
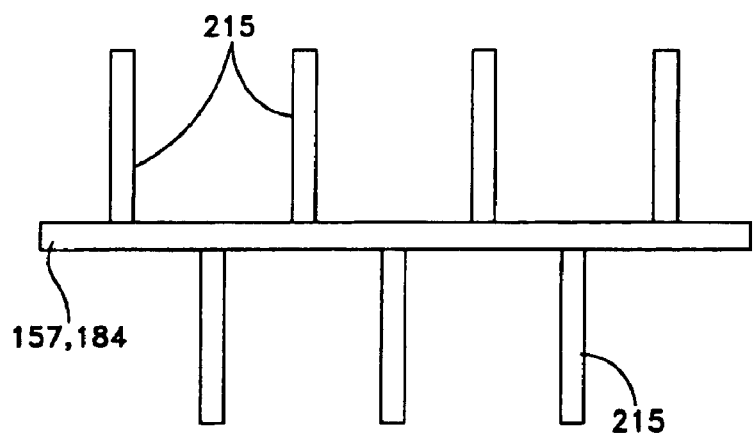
FIG. 54 is a top plan view of the elongated body and rib assembly of FIG. 53.

In FIGS. 53 and 54, there is shown an alternative embodiment in which an elongated body 157, 184 has fixed thereto a series of ribs 215 in two lines of ribs. As may be seen in FIG. 54, the lines of ribs 215 are preferably offset from each other, such that a rib on one side of the elongated body 157, 184 is not opposite a rib on the other side of the elongated body. This permits the ribs 215 to be flexed toward the opposite side without engaging a rib of the opposite side. The flexing of the ribs permits the ribs to be compressed for disposition in a catheter.

Figure 55:
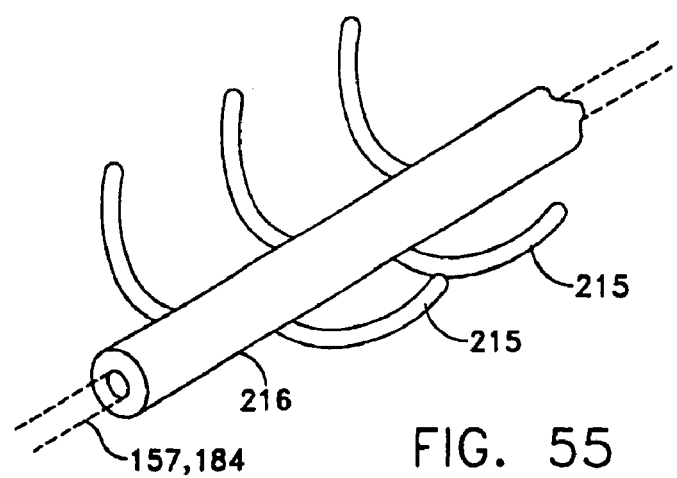
FIG. 55 is a schematic perspective view of another combination of elongated body and stabilizing scaffold.

In FIG. 55 there is shown an alternative construction similar to that of FIG. 54, but showing the ribs 215 connected to a spine 216, and with the spine 216 being cannulated so as to receive elongated body 157, 184 therein.

Figure 56:
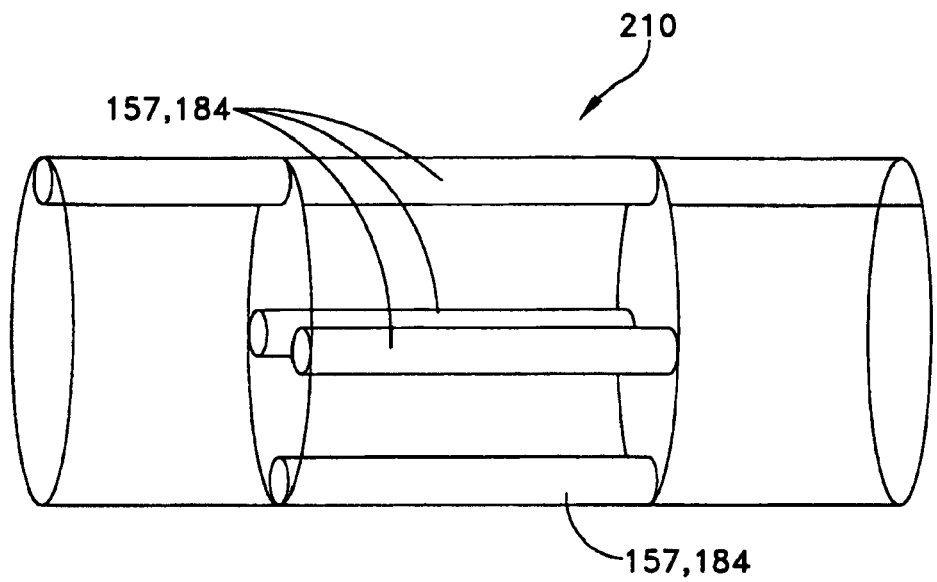
FIG. 56 is a diagrammatic perspective view of a combination of elongated body and stabilizing scaffold in which the structure of the stabilizing scaffold includes a plurality of elongated body components.

In FIG. 56 there is shown an alternative combination elongated body and scaffold assembly in which the stabilizing scaffold 210 includes elongated body portions 157, 184 in the form of rods integral with the scaffold. In the embodiment shown in FIG. 56, at least one body portion 157, 184 extends from end to end of the assembly, while other body portions 157, 184 extend only through a mid-portion of the assembly. Thus, the end portions of the assembly are less rigid than the mid-portion thereof.

Figure 57:
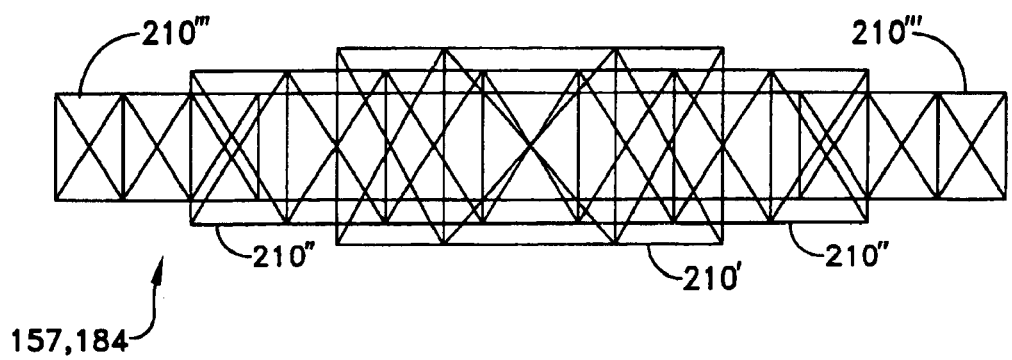
FIG. 57 is a diagrammatic side elevational view of an elongated body constructed entirely of stabilizing scaffold members.

Referring to FIG. 57, it will be seen that the body 157, 184 may comprise only stabilizing scaffolds, for example stabilizing scaffolds 210', 210'', and 210''' arranged telescopically, such that the mid-portion includes all three stabilizing scaffolds 210', 210'', and 210''', portions immediately outboard of the mid-portion include the stabilizing scaffolds 210'' and 210''', while end portions comprise only stabilizing scaffolds 210'''. Thus, the mid-portion of the body 157, 184 is the most resistant to movement, while the end portions are the least resistant, with zones at stabilizing scaffolds 210'' exercising less resistance than the mid-portion but greater than the end portions.

Figure 58:
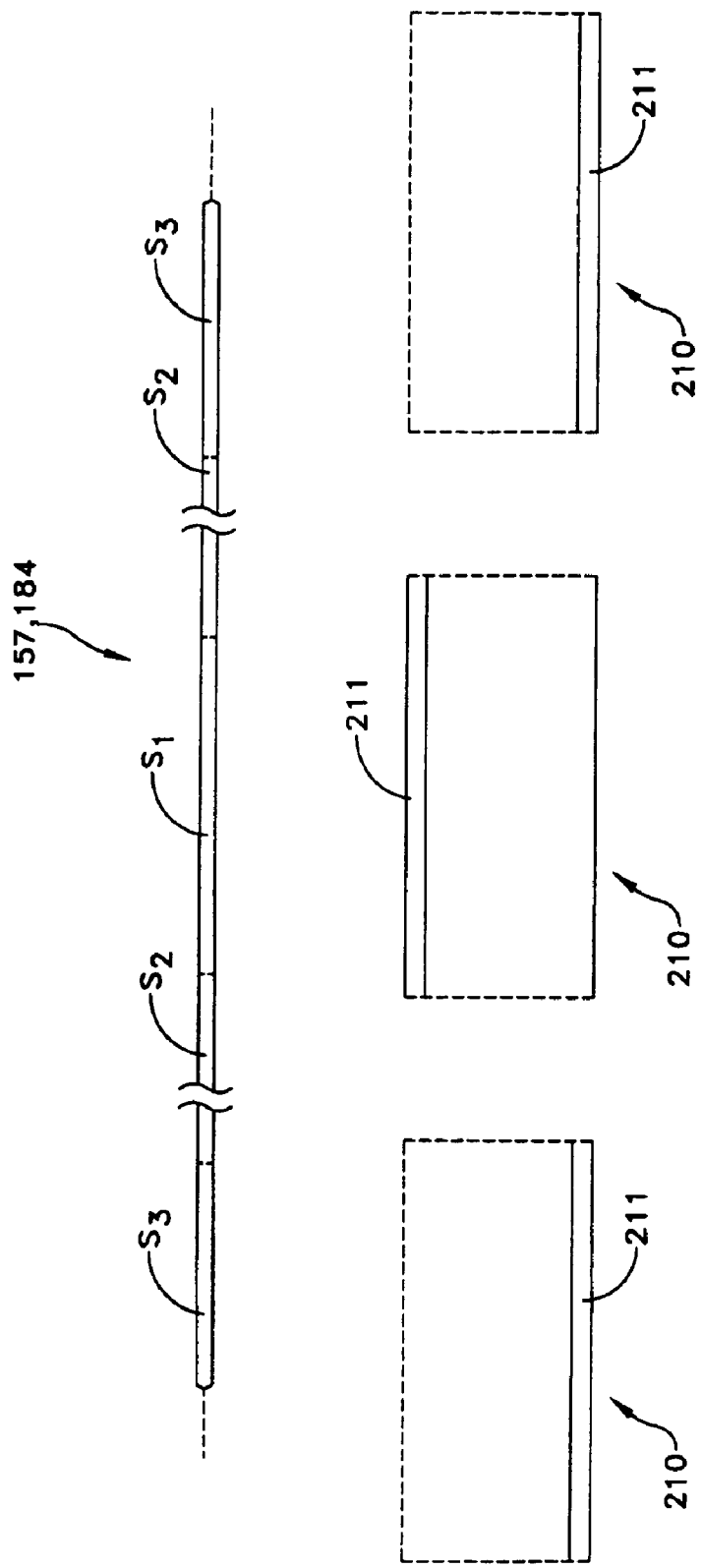
FIG. 58 is a schematic side view showing another combination of elongated body and stabilizing scaffolds formed in accordance with the present invention.
Figure 59:
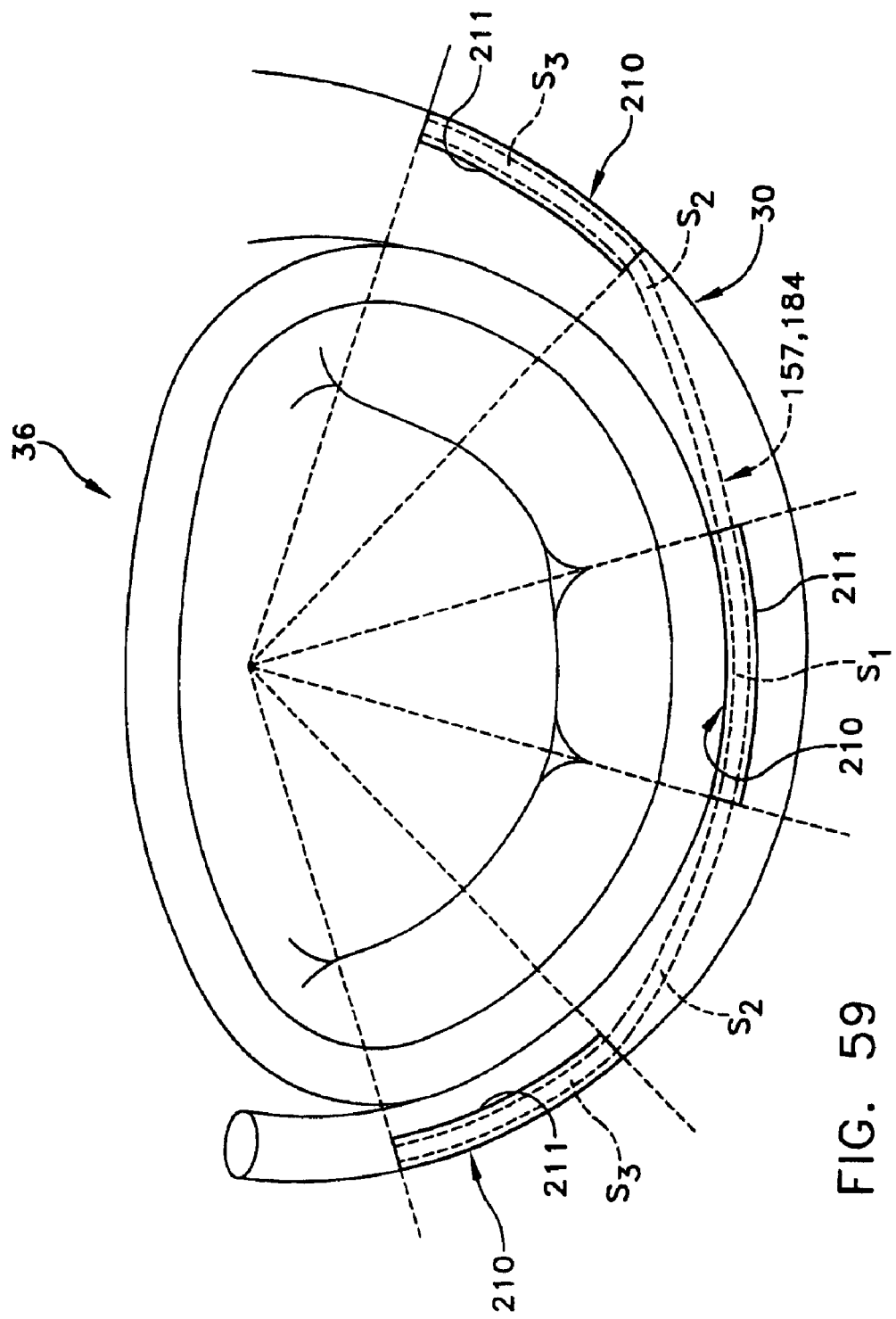
FIG. 59 is a schematic side view showing the stabilizing scaffolds of FIG. 57 deployed in the coronary sinus of a patient.
Figure 60:
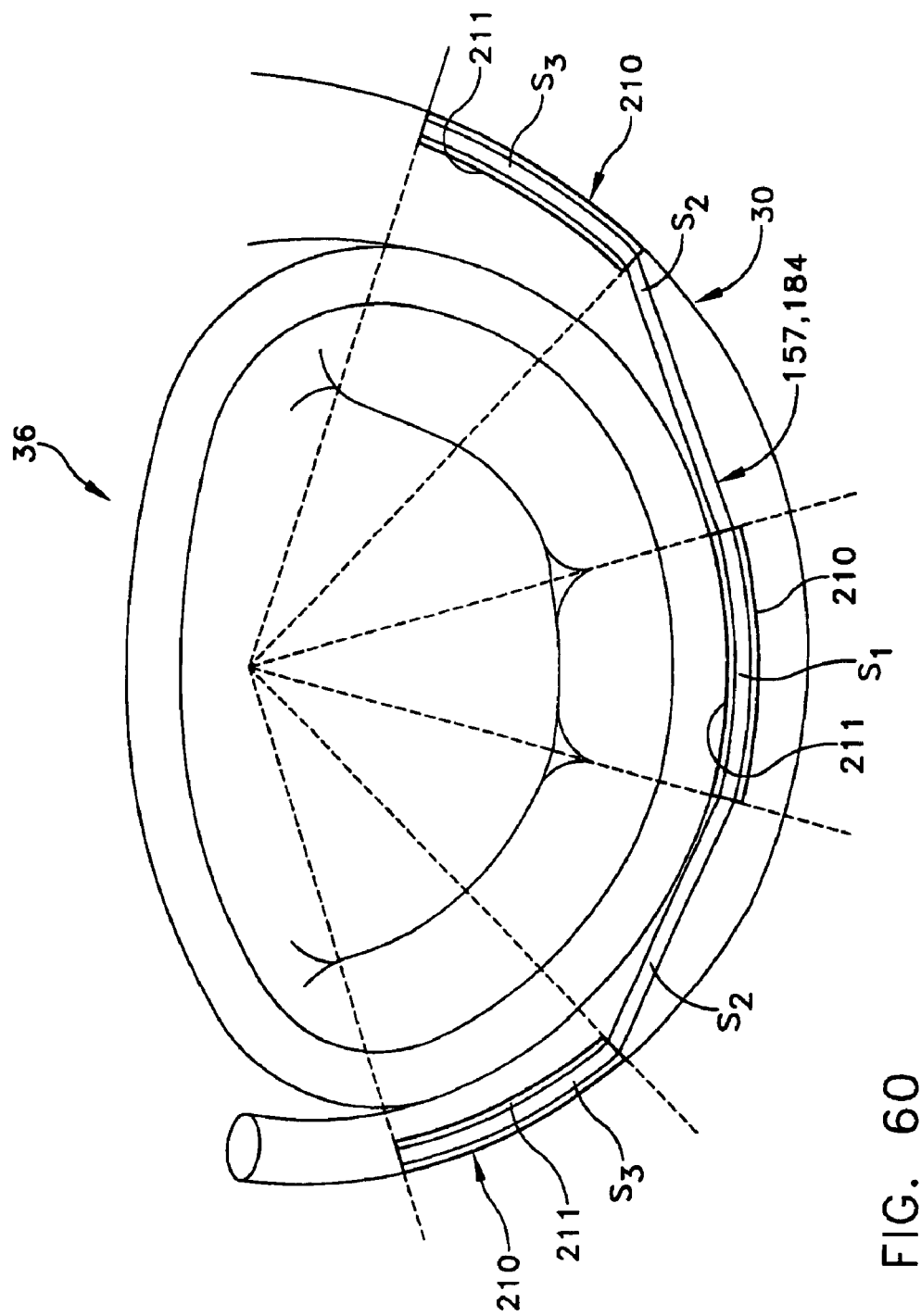
FIG. 60 is a schematic side view showing the combination of elongated body and stabilizing scaffolds of FIG. 57 deployed in the coronary sinus of a patient.

Looking next at FIGS. 58–60, there is shown an alternative combination of elongated body and scaffold assembly, wherein the elongated body comprises a 5-zone elongated body 157, 184 of the sort shown in FIGS. 23 and 24, and the scaffold comprises three supporting scaffolds, each of the sort shown in FIGS. 40–47, i.e., having a guide 211 for receiving the elongated body 157, 184. More particularly, the 5-zone elongated body 157, 184 comprises a plurality of segments $S_1$, $S_2$ and $S_3$, where segment $S_1$ is configured to have a selected degree of flexibility, segments $S_2$ are configured to have a lower degree of flexibility than segment $S_1$, and segments $S_3$ are configured to have a higher degree of flexibility than segment $S_1$. As a result of this construction, segment $S_1$ will carry the load of reconfiguring the mitral annulus, segments $S_2$ will transfer that load far outboard to segments $S_3$, and segments $S_3$ will dissipate that load outboard to the side walls of the coronary sinus. In a preferred form of the invention, segment $S_1$ is constructed so as to have a degree of flexibility which will support the remodeling of the mitral annulus yet permit the segment $S_1$ to roughly conform to the arc of curvature of the mitral annulus at the point of engagement; the segment $S_2$ is constructed so as to have a degree of flexibility sufficiently low so that substantially all of the load generated by the remodeling of the mitral annulus will be transferred to the segments $S_3$; and the segments $S_2$ have a length sufficiently long that posteriorly-directed forces on the walls of the coronary sinus (e.g., as shown by the arrows P in FIG. 7) will be applied in the area of the valve commissures. Supporting scaffolds 210 are positioned in coronary sinus 30 so that one scaffold 210 receives segment $S_1$, one scaffold 210 receives one segment $S_2$, and the one scaffold 210 receives the other segment $S_3$. Elongated body 157, 184 may be deployed at the same time as supporting scaffolds 210 or after supporting scaffolds 210 have been deployed. Preferably segments $S_3$ are able to slide in scaffold guides 211, particularly where elongated body 157, 184 is designed to effect tissue remodeling gradually, over a prolonged period of time. Among other things, such a construction has been formed to center itself naturally in the region around the posterior leaflet and conforms nicely to the curvature of the posterior leaflet. If desired, such a "5-zone" elongated body can be formed out of a single material, with different diameters being used to create the different body zones.

It should also be appreciated that scaffold 210 may have a stent-like configuration or may have rib-like configuration as shown in FIGS. 53 and 54.

Figure 61:
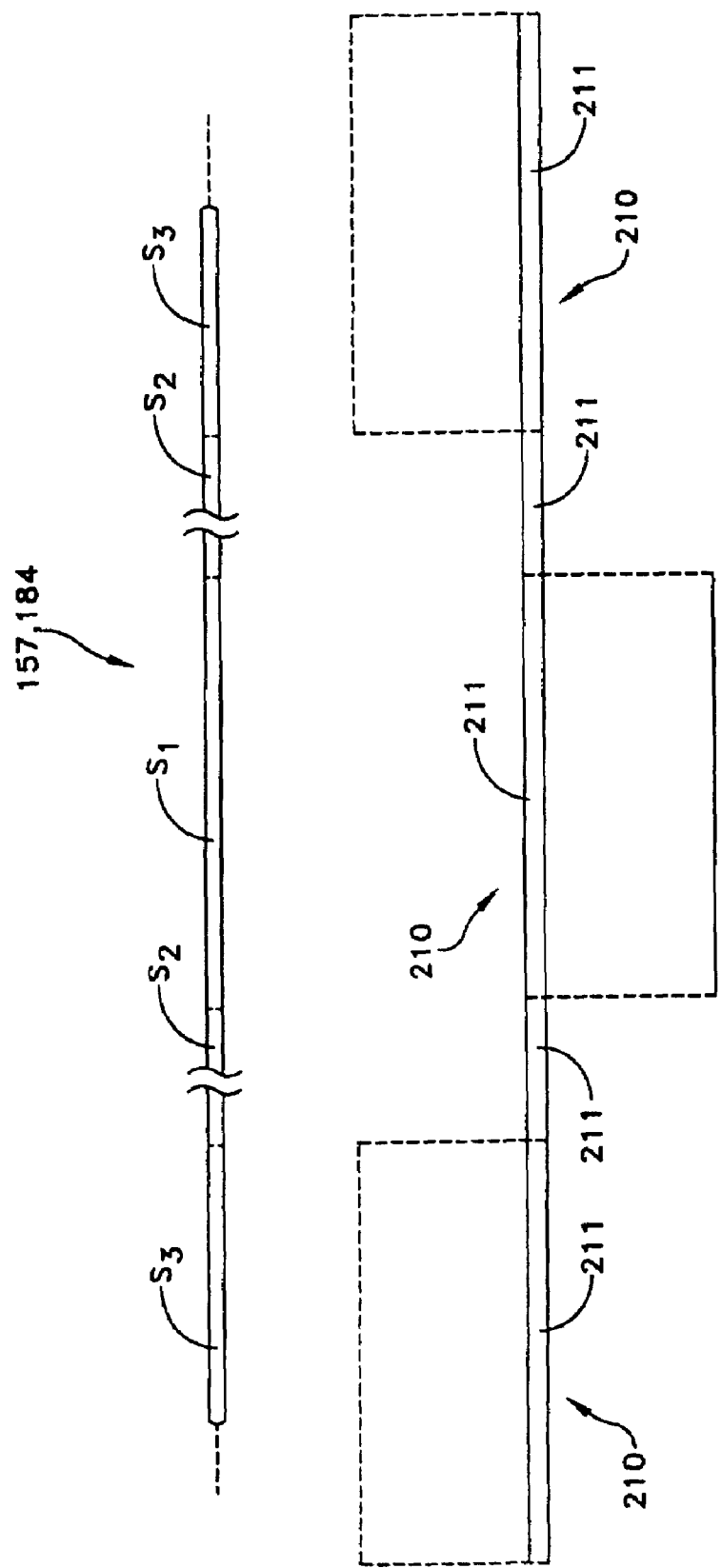
FIG. 61 is a schematic side view showing another combination of elongated body and stabilizing scaffolds formed in accordance with the present invention.
Figure 62:
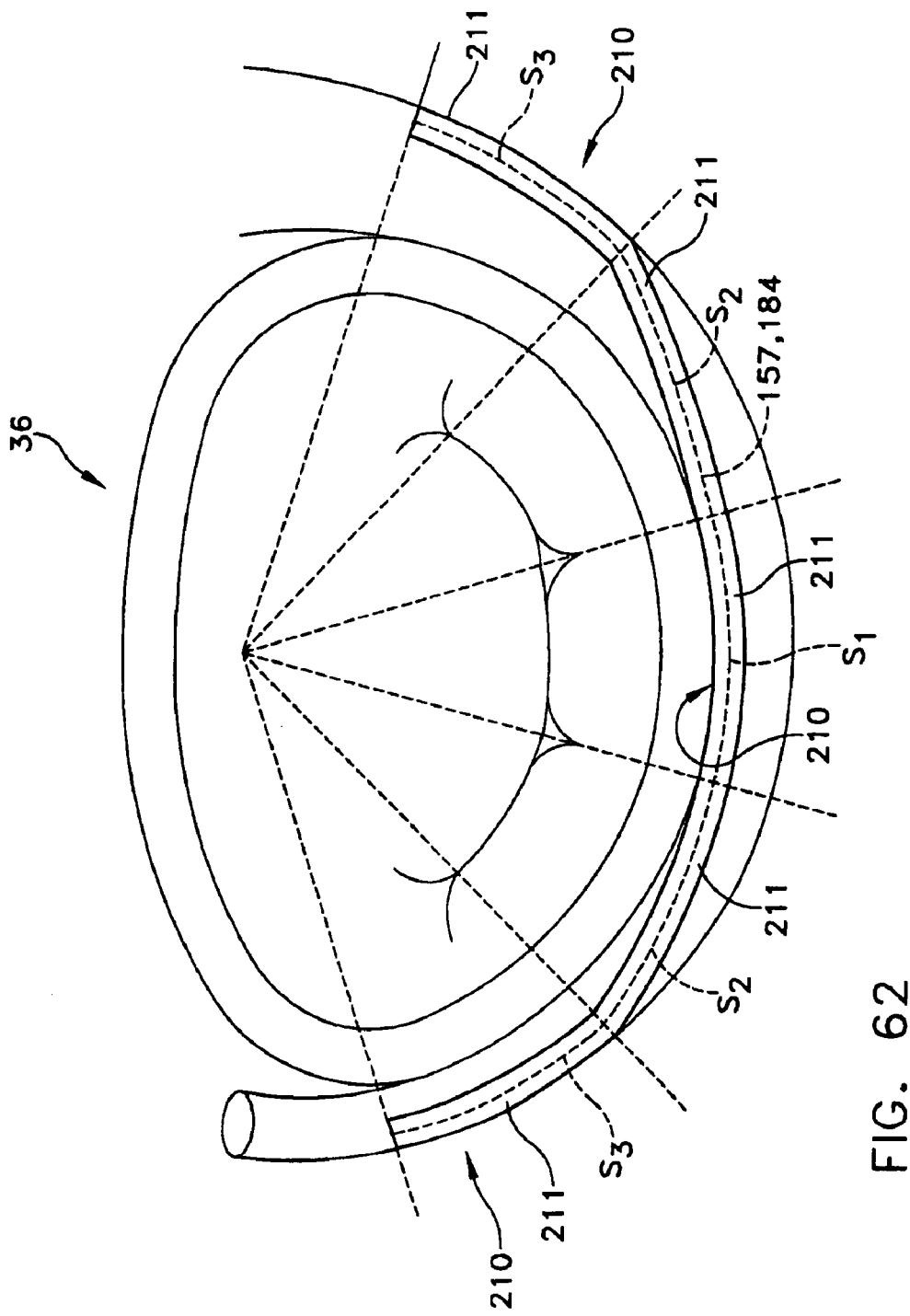
FIG. 62 is a schematic side view showing the stabilizing scaffolds of FIG. 60 deployed in the coronary sinus of a patient.
Figure 63:
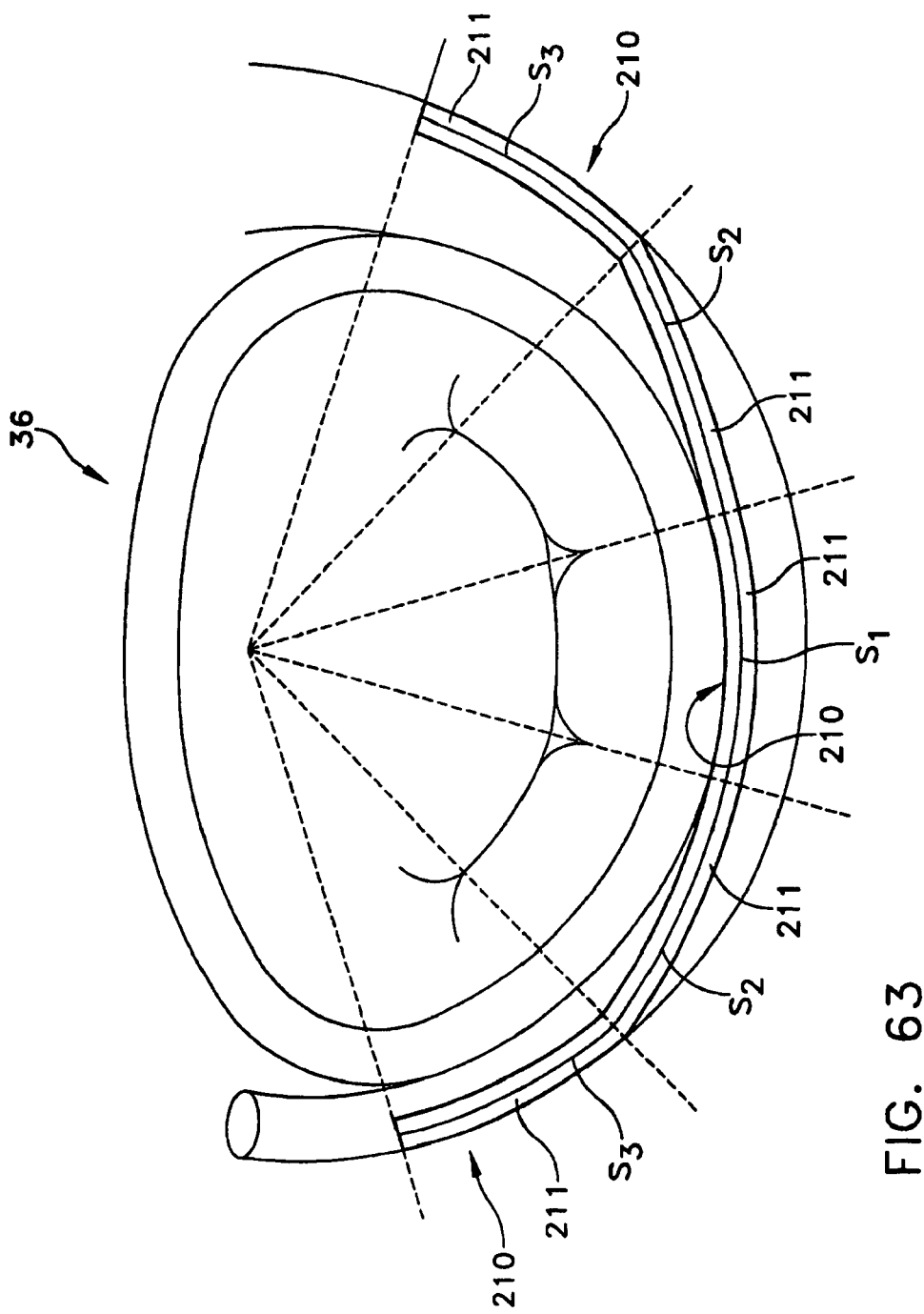
FIG. 63 is a schematic side view showing the combination of elongated body and stabilizing scaffolds of FIG. 60 deployed in the coronary sinus of a patient.

Looking next at FIGS. 61–63, there is shown a combination elongated body and scaffold assembly similar to that shown in FIGS. 58–60, except that the guide 211 extends between each of the scaffold zones so as to form a singular scaffold structure which has three zones engaging the walls of the coronary sinus.

There are thus provided varied stabilizing scaffold configurations for preventing migration of the substantially straight, substantially rigid elongated bodies, and combinations of bodies and stabilizing scaffolds for similarly preventing, or mitigating against, such migration.

It is to be understood that the present invention is by no means limited to the particular constructions herein disclosed and/or shown in the drawings, but also comprises any modifications or equivalents within the scope of the claims.

What is claimed is:

1. Apparatus for reducing mitral regurgitation, the apparatus comprising:
   an elongated bar adapted for insertion into a coronary sinus in the vicinity of the posterior leaflet of the mitral valve, said bar having a straight configuration in an unstressed state, said bar comprising five segments disposed end-to-end, said segments comprising:
   a central segment provided with a selected first degree of flexibility which provides rigidity sufficient to reconfigure the mitral annulus;
   a pair of intermediate segments, one disposed at each end of said central segment, said intermediate segments each being provided with a selected second degree of flexibility which provides more rigidity to said intermediate segments than the rigidity of said central segment; and a pair of outer segments, each disposed at the end of an intermediate segment remote from said central segment, said outer segments each being provided with a third degree of flexibility exceeding the flexibility of said central segment and said intermediate segments;

whereby upon the insertion of said bar into the coronary sinus, said central segment serves to reconfigure the mitral annulus, said intermediate segments serve to transfer the load of reconfiguring the mitral annulus to said outer segments, and said outer segments serve to dissipate the load to side walls of the coronary sinus.

2. The apparatus in accordance with claim 1 wherein said central segment is more rigid than anatomical tissue disposed between the coronary sinus and the mitral valve.

3. The apparatus in accordance with claim 2 wherein said central segment is of sufficient length to cause a portion of the coronary sinus to assume a straighter configuration.

4. The apparatus in accordance with claim 2 wherein said central segment is provided with a configuration straighter than the shape of the coronary sinus in the vicinity of the posterior leaflet of the mitral valve, and a length relative to the radius of curvature of the coronary sinus to import a straightening force to the wall of the coronary sinus.

5. The apparatus in accordance with claim 1 wherein said segments are formed of a single material, and said central segment is provided with a first diameter, said intermediate segments are each provided with a second diameter, and said outer segments are each provided with a third diameter.

6. The apparatus in accordance with claim 1 wherein said bar is of a circular cross-section.

7. The apparatus in accordance with claim 1 wherein said central segment is adapted to apply an anteriorly directed force to walls of the coronary sinus substantially adjacent to the posterior leaflet of the mitral valve, and the outer segments each apply a posteriorly directed force to the walls of the coronary sinus.

8. The apparatus in accordance with claim 1 wherein each of said segments comprises a zone in a bar of unitary construction.

9. The apparatus in accordance with claim 1 wherein each of said segments is connected to at least one other of said segments by a joint.

10. The apparatus in accordance with claim 1 wherein said bar comprises a superelastic material.

11. The apparatus in accordance with claim 1 wherein said bar is mounted to a push rod for advancing said bar within the coronary sinus.

12. The apparatus in accordance with claim 1 wherein said bar is selectable from a kit comprising a plurality of bars having different flexibility characteristics.

13. The apparatus in accordance with claim 1 further comprising a delivery catheter adapted to be positioned within the coronary sinus of the patient, said flexible delivery catheter being formed out of a flexible material so that said delivery catheter is adapted to substantially assume the configuration of the coronary sinus, said delivery catheter being adapted to receive said bar therein.

14. The apparatus in accordance with claim 13 further comprising a removable guidewire for positioning said delivery catheter in the coronary sinus.

15. A method for reducing mitral regurgitation, the method comprising the steps of:

providing a bar having a substantially straight configuration in an unstressed state, the bar comprising five segments disposed end-to-end, the segments comprising:

a central segment provided with a selected first degree of flexibility which provides rigidity sufficient to reconfigure the mitral annulus;

a pair of intermediate segments, one disposed at each end of the central segment, the intermediate segments being provided with a selected second degree of flexibility which provides more rigidity to the intermediate segments than the rigidity of the central segment; and a pair of outer segments, each disposed at the end of an intermediate segment remote from the central segment, the outer segments being provided with a third degree of flexibility exceeding the flexibility of the central segment and the intermediate segments; and inserting the bar into the coronary sinus of a patient in the vicinity of the posterior leaflet of the mitral valve, whereby upon the insertion of the bar into the coronary sinus, the central segment serves to reconfigure the mitral annulus, the intermediate segments serve to transfer the load of reconfiguring the mitral annulus to the outer segments, and the outer segments serve to dissipate the load to side walls of the coronary sinus, thereby to reduce mitral regurgitation.

16. A method according to claim 15 wherein the bar is inserted into the coronary sinus percutaneously.

17. A method according to claim 15 wherein the bar is inserted into the coronary sinus by introducing the bar into the patient's jugular vein, passing the bar down the superior vena cava, passing the bar through the right atrium and then passing the bar into the coronary sinus.

18. A method according to claim 15 wherein the bar is inserted into the coronary sinus by introducing the bar into the patient's left subclavian vein, passing the bar down the superior vena cava, passing the bar through the right atrium and then passing the bar into the coronary sinus.

19. A method according to claim 15 wherein the bar is inserted into the coronary sinus through an incision in the patient's heart.

20. A method according to claim 15 wherein the bar is guided into position by passing the bar through a pre-positioned delivery catheter.

21. A method according to claim 20 wherein the bar is mounted to a push rod for advancing the bar within the delivery catheter.

22. A method according to claim 20 further comprising providing a removable guidewire for positioning the delivery catheter in the coronary sinus.

23. A method according to claim 15 wherein the bar effects valve remodeling on a continuous basis over a prolonged period of time.

24. A method according to claim 15 wherein the bar is formed at least in part out of a superelastic material.

25. A method according to claim 15 wherein the bar is inserted under visualization.

26. A method according to claim 25 wherein visualization is achieved by using a procedure selected from the group consisting of fluoroscopy, echocardiography, intravascular ultrasound, angioscopy and real-time magnetic resonance imaging.

27. A method according to claim 15 including an additional step of assessing the efficacy of the procedure by observing the reduction of mitral regurgitation.

28. A method according to claim 15 further comprising a subsequent step of removing the bar from the coronary sinus.

* * * * *